(12) United States Patent
Bastian et al.

(10) Patent No.: US 7,652,015 B2
(45) Date of Patent: Jan. 26, 2010

(54) KINASE INHIBITORS

(75) Inventors: Jolie Anne Bastian, Indianapolis, IN (US); Jesus Andres Blas de Blas, Alcobendas (ES); Alfonso De Dios, Carmel, IN (US); Kevin John Hudziak, Indianapolis, IN (US); Tiechao Li, Fishers, IN (US); Beatriz López De Uralde-Garmendia, Alcobendas (ES); Mary Margaret Mader, Fishers, IN (US); Michael Ray Myers, Fishers, IN (US); Mark Andrew Pobanz, Westfield, IN (US); Chuan Shih, Carmel, IN (US); Boyu Zhong, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 43 days.

(21) Appl. No.: 12/088,526

(22) PCT Filed: Oct. 25, 2006

(86) PCT No.: PCT/US2006/041644

§ 371 (c)(1),
(2), (4) Date: Mar. 28, 2008

(87) PCT Pub. No.: WO2007/053394

PCT Pub. Date: May 10, 2007

(65) Prior Publication Data

US 2008/0269244 A1 Oct. 30, 2008

(30) Foreign Application Priority Data

Jun. 2, 2006 (EP) .................................. 06380151

(51) Int. Cl.
*A61K 31/4439* (2006.01)
*A61K 31/454* (2006.01)
*C07D 401/12* (2006.01)
*C07D 401/14* (2006.01)
*C07D 409/14* (2006.01)

(52) U.S. Cl. .................. 514/253.09; 514/318; 544/364; 546/194

(58) Field of Classification Search ...................... None
See application file for complete search history.

(56) References Cited

U.S. PATENT DOCUMENTS

2008/0306068 A1 * 12/2008 Li et al. .................... 514/236.5

FOREIGN PATENT DOCUMENTS

WO WO 99/32110 7/1999

OTHER PUBLICATIONS

Regan, J., et al., Pyrazole urea-based inhibitors of p39 MAP kinase: from lead compound to clinical candidate, Journal of Medicinal Chemistry, American Chemical Society, Washington US, vol. 45, No. 14, May 25, 2002.

* cited by examiner

*Primary Examiner*—Emily Bernhardt
(74) *Attorney, Agent, or Firm*—Tina M. Tucker; Tonya Combs

(57) ABSTRACT

The present invention provides kinase inhibitors of Formula (I). Wherein $R^1$, $R^2$, X and Z are as described herein, or a pharmaceutically acceptable salt thereof.

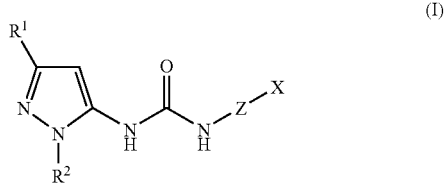

(I)

9 Claims, No Drawings

KINASE INHIBITORS

BACKGROUND OF THE INVENTION

The p38 kinase is a mitogen-activated protein (MAP) kinase that belongs to the serine/threonine kinase superfamily. This kinase is activated by extracellular stresses such as heat, UV light, and osmotic stress, as well as by inflammatory stimuli such as lipopolysaccharide. When activated, p38 kinase phosphorylates intracellular protein substrates that regulate the biosynthesis of the pro-inflammatory cytokines tumor necrosis factor α (TNFα) and interleukin-1β (IL-1β). These cytokines are implicated in the pathology of a number of chronic inflammatory disorders (Lee, et al., *Ann. N.Y. Acad. Sci.*, 696, 149-170 (1993); Muller-Ladner, *Curr. Opin. Rheumatol.*, 8, 210-220 (1996)), cardiovascular and central nervous system disorders (Salituro, et al., *Current Medicinal Chemistry*, 6, 807-823 (1999)), and autoimmune disorders (Pargellis, et al., *Nature Structural Biology*, 9(4), 268-272 (2002)). In addition, the phosphorylated form of mitogen-activated protein kinase-protein kinase 2 (or pMAPKAPK2) is also a kinase in the p38 MAPK pathway and can be directly activated by p38 MAPK. Mouse knockout studies of MAPKAPK2 show a reduction in cytokine production suggesting MAPKAPK2 can be a key regulator of the inflammatory response and can also be a potential target for anti-inflammatory therapy (WO 2005120509).

A number of urea compounds (for example in WO 9923091, WO 01012188, WO 04004720, WO 04037789, WO 99/32111, US 2004/0058961, EP 1609789, WO 03072569 and WO 0043384) have been identified as p38 kinase inhibitors or cytokine inhibitors. P38 kinase inhibitors or cytokine inhibitors may be costly to produce and may have bioavailability and absorption problems that limit the in vivo effects and therapeutic use. Therefore a need exists for new small molecule cytokine suppressive drugs, i.e., compounds that are capable of inhibiting p38 kinase with improved potency and greater bioavailability.

The present invention provides new inhibitors of p38 kinase useful for the treatment of conditions resulting from excessive cytokine production.

BRIEF SUMMARY OF THE INVENTION

The present invention provides compounds of Formula I:

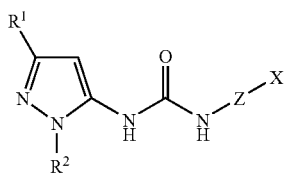

where:

Z is selected from the group consisting of

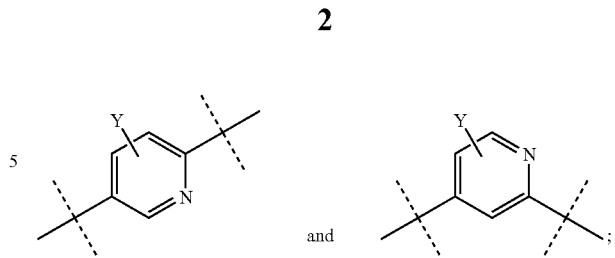

X is selected from the group consisting of

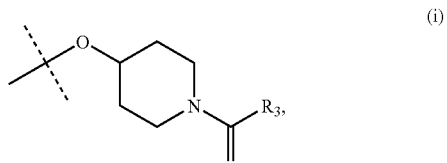

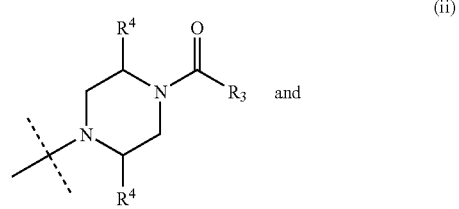

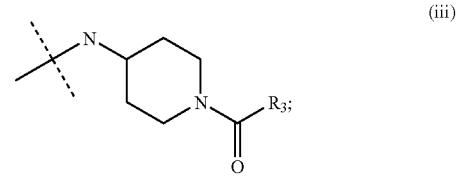

$R^1$ is $C_1$-$C_7$ alkyl optionally substituted with one to six substituents selected from the group consisting of halo and $C_1$-$C_4$ alkylhalo; $C_3$-$C_6$ cycloalkyl optionally substituted with one or two substituents selected from the group consisting of $C_1$-$C_4$ alkyl and trifluoromethyl; or trimethylsilyl;

$R^2$ is phenyl optionally substituted with $C_1$-$C_4$ alkyl, or pyridinyl optionally substituted with $C_1$-$C_4$ alkyl;

Y is hydrogen, $C_1$-$C_4$ alkyl, halo, or $C_1$-$C_4$ alkylhalo;

$R^3$ is $C_1$-$C_7$ alkyl optionally substituted with $C_3$-$C_6$ cycloalkyl; $C_1$-$C_4$ alkoxy; $C_1$-$C_4$ alkylhalo; $C_3$-$C_6$ cycloalkyl optionally substituted with one to four substituents selected from the group of $C_1$-$C_4$ alkyl and trifluoromethyl; or pyridyl, phenyl or thienyl each optionally substituted with a first substituent selected from the group consisting of: halo, cyano, $C_1$-$C_4$ alkyl, $C_1$-$C_4$ alkylhalo and $C_1$-$C_4$ alkoxy, and optionally further substituted with a second substituent selected from the group of $C_1$-$C_4$ alkyl and halo; and $R^4$ is hydrogen or $C_1$-$C_4$ alkyl; or a pharmaceutically acceptable salt thereof.

The present invention also provides a method of inhibiting p38 kinase in a mammal comprising administering to a mammal in need of such treatment an effective amount of a compound of Formula I or a pharmaceutically acceptable salt thereof.

The present invention also provides a method of suppressing the production of tumor necrosis factor α (TNFα) in a mammal comprising administering to a mammal in need of such treatment an effective amount of a compound of Formula I or a pharmaceutically acceptable salt thereof.

The present invention also provides a method of suppressing the production of interleukin-1β (IL-1β) in a mammal comprising administering to a mammal in need of such treatment an effective amount of a compound of Formula I or a pharmaceutically acceptable salt thereof.

The present invention further provides a method of treating conditions resulting from excessive cytokine production in a mammal comprising administering to a mammal in need of such treatment a cytokine-suppressing amount of a compound of Formula I or a pharmaceutically acceptable salt thereof.

The present invention also provides a method of inhibiting the growth of a susceptible neoplasm in a mammal comprising administering to a mammal in need of such treatment a p38 inhibiting amount of a compound of Formula I or a pharmaceutically acceptable salt thereof.

The present invention also provides a method of inhibiting metastasis in a mammal comprising administering to a mammal in need of such treatment a p38 inhibiting amount of a compound of Formula I or a pharmaceutically acceptable salt thereof.

The present invention also provides a method of treating rheumatoid arthritis in a mammal comprising administering to a mammal in need of such treatment a p38 inhibiting amount of a compound of Formula I a pharmaceutically acceptable salt thereof.

The present invention also provides a pharmaceutical formulation comprising a compound of Formula I or a pharmaceutically acceptable salt thereof, in combination with a pharmaceutically acceptable excipient, carrier, or diluent.

This invention also provides the use of a compound of Formula I or a pharmaceutically acceptable salt thereof for the manufacture of a medicament for the inhibition of p38 kinase. Additionally, this invention provides a compound of Formula I or a pharmaceutically acceptable salt thereof for use in the inhibition of p38 kinase in mammals. Furthermore, this invention provides a pharmaceutical composition adapted for the inhibition of p38 kinase comprising a compound of Formula I or a pharmaceutically acceptable salt thereof in combination with one or more pharmaceutically acceptable excipients, carriers, or diluents thereof.

This invention also provides the use of a compound of Formula I or a pharmaceutically acceptable salt thereof for the manufacture of a medicament for the suppression of the production of tumor necrosis factor α (TNFα). Additionally, this invention provides a compound of Formula I or a pharmaceutically acceptable salt thereof for use in the suppression of the production of tumor necrosis factor α (TNFα) in mammals. Furthermore, this invention provides a pharmaceutical composition adapted for the suppression of the production of tumor necrosis factor α (TNFα) comprising a compound of Formula I or a pharmaceutically acceptable salt thereof in combination with one or more pharmaceutically acceptable excipients, carriers, or diluents.

This invention also provides the use of a compound of Formula I or a pharmaceutically acceptable salt thereof for the manufacture of a medicament for the suppression of the production of interleukin-1β (IL-1β). Additionally, this invention provides a compound of Formula I or a pharmaceutically acceptable salt thereof for use in the suppression of the production of interleukin-1β (IL-1β) in mammals. Furthermore, this invention provides a pharmaceutical composition adapted for the suppression of the production of interleukin-1β (IL-1β) comprising a compound of Formula I, or a pharmaceutically acceptable salt thereof, in combination with one or more pharmaceutically acceptable excipients, carriers, or diluents.

This invention also provides the use of a compound of Formula I or a pharmaceutically acceptable salt thereof for the manufacture of a medicament for the treatment of conditions resulting from excessive cytokine production. Additionally, this invention provides a compound of Formula I or a pharmaceutically acceptable salt thereof for use in the treatment of conditions resulting from excessive cytokine production in mammals. Furthermore, this invention provides a pharmaceutical composition adapted for the treatment of conditions resulting from excessive cytokine production comprising a compound of Formula I or a pharmaceutically acceptable salt thereof in combination with one or more pharmaceutically acceptable excipients, carriers, or diluents.

This invention also provides the use of a compound of Formula I or a pharmaceutically acceptable salt thereof for the manufacture of a medicament for the inhibition of growth of a susceptible neoplasm. Additionally, this invention provides a compound of Formula I or a pharmaceutically acceptable salt thereof for use in the inhibition of growth of a susceptible neoplasm in mammals. Furthermore, this invention provides a pharmaceutical composition adapted for the inhibition of growth of a susceptible neoplasm comprising a compound of Formula I or a pharmaceutically acceptable salt thereof in combination with one or more pharmaceutically acceptable excipients, carriers, or diluents.

This invention also provides the use of a compound of Formula I or a pharmaceutically acceptable salt thereof for the manufacture of a medicament for the inhibition of metastasis. Additionally, this invention provides a compound of Formula I or a pharmaceutically acceptable salt thereof for use in the inhibition of metastasis in mammals. Furthermore, this invention provides a pharmaceutical composition adapted for the inhibition of metastasis comprising a compound of Formula I or a pharmaceutically acceptable salt thereof in combination with one or more pharmaceutically acceptable excipients, carriers, or diluents.

This invention also provides the use of a compound of Formula I or a pharmaceutically acceptable salt thereof for the manufacture of a medicament for the treatment of rheumatoid arthritis. Additionally, this invention provides a compound of Formula I or a pharmaceutically acceptable salt thereof for use in the treatment of rheumatoid arthritis in mammals. Furthermore, this invention provides a pharmaceutical composition adapted for the treatment of rheumatoid arthritis comprising a compound of Formula I or a pharmaceutically acceptable salt thereof in combination with one or more pharmaceutically acceptable excipients, carriers, or diluents.

DETAILED DESCRIPTION OF THE INVENTION

The term "p38 kinase" is taken to mean the p38β and/or p38β kinase isoforms.

The term "suppressing the production of TNFα (IL-1β, cytokine)" is taken to mean decreasing of excessive in vivo levels of TNFα, IL-1β, or another cytokine in a mammal to normal or sub-normal levels. This may be accomplished by inhibition of the in vivo release of TNFα, IL-1β, or another cytokine by all cells, including macrophages; by down regulation, at the genomic level, of excessive in vivo levels of TNFα, IL-1β, or another cytokine in a mammal to normal or sub-normal levels; by inhibition of the synthesis of TNFα, IL-1β, or another cytokine as a posttranslational event; or by a down regulation of TNFα, IL-1β, or another cytokine at the translational level.

The skilled artisan will appreciate that certain compounds of Formula I contain at least one chiral center. The present invention contemplates all individual enantiomers or diastereomers, as well as mixtures of enantiomers and diastereomers of said compounds including racemates. It is preferred that compounds of Formula I containing at least one chiral center exist as single enantiomers or diastereomers. The single enantiomers or diastereomers may be prepared beginning with chiral reagents or by steroselective or stereospecific synthetic techniques. Alternatively, the single enantiomers or diastereomers may be isolated from mixtures by standard chiral chromatographic or crystallization techniques.

It will be understood by the skilled reader that the compounds of the present invention are capable of forming acid addition salts. In all cases, the pharmaceutically acceptable salts of all of the compounds are included in the names of them. Compounds of the present invention are amines, and accordingly will react with any of a number of inorganic and organic acids to form pharmaceutically acceptable acid addition salts. The term "pharmaceutically acceptable salt" as used herein, refers to salts of the compounds of Formula I which are substantially non-toxic to living organisms. Typical pharmaceutically acceptable salts include those salts prepared by reaction of the compounds of the present invention with a pharmaceutically acceptable organic or inorganic acids. Such salts include the pharmaceutically acceptable salts listed in *Journal of Pharmaceutical Science*, 66, 2-19 (1977), which are known to the skilled artisan. Mesylate salts of compounds of Formula I are most preferred.

Compounds of Formula I are inhibitors of p38 kinase. Thus, the present invention also provides a method of inhibiting p38 kinase in a mammal that comprises administering to a mammal in need of said treatment a p38 kinase-inhibiting amount of a compound of Formula I. It is preferred that the mammal to be treated by the administration of the compounds of Formula I is human.

As inhibitors of p38 kinase, compounds of the present invention are useful for suppressing the production of the pro-inflammatory cytokines tumor necrosis factor α (TNFα) and interleukin-1β (IL-1β), and therefore for the treatment of disorders resulting from excessive cytokine production. The present compounds are therefore believed to be useful in treating inflammatory disorders, including eczema, atopic dermatitis, rheumatoid arthritis, osteoarthritis, inflammatory bowel disease, and toxic shock syndrome. Compounds of the present invention are also believed to be useful in the treatment of cardiovascular disorders, such as acute myocardial infarction, chronic heart failure, atherosclerosis, viral myocarditis, cardiac allograft rejection, and sepsis-associated cardiac dysfunction. Furthermore, compounds of the present invention are also believed to be useful for the treatment of central nervous system disorders, such as meningococcal meningitis, Alzheimer's disease, Parkinson's disease, and multiple sclerosis. WO 99/32111, WO 9923091, WO 04004720, WO 03072569.

Most solid tumors increase in mass through the proliferation of malignant cells and stromal cells, including endothelial cells. In order for a tumor to grow larger than 2-3 millimeters in diameter, it must form a vasculature, a process known as angiogenesis. Suppression of tumor-induced angiogenesis by angiostatin and endostatin has been reported to result in antitumor activity (O'Reilly, et al., *Cell*, 88, 277-285 (1997)). The selective p38 kinase inhibitor SB22025 has been shown to inhibit angiogenesis (J. R. Jackson, et al., *J. Pharmacol. Exp. Therapeutics*, 284, 687 (1998)). Because angiogenesis is a critical component of the mass expansion of most solid tumors, the development of new p38 kinase inhibitors for the inhibition of this process represents a promising approach for antitumor therapy. This approach to antitumor therapy may lack the toxic side effects or drug resistance-inducing properties of conventional chemotherapy (Judah Folkman, *Endogenous Inhibitors of Angiogenesis*, The Harvey Lectures, Series 92, pages 65-82, Wiley-Liss Inc., (1998)).

As inhibitors of p38 kinase, compounds of the present invention, therefore, are also useful in inhibiting growth of susceptible neoplasms. Schultz, R. M. *Potential of p38 MAP kinase inhibitors in the treatment of cancer*. In: E. Jucker (ed.), *Progress in Drug Research*, 60, 59-92, (2003). A susceptible neoplasm is defined to be a neoplasm that depends upon p38 kinase for its survival, growth, or metastasis.

Susceptible neoplasms include tumors of the brain, genitourinary tract, lymphatic system, stomach, larynx, and lung (U.S. Pat. No. 5,717,100). Preferably, the term "susceptible neoplasms" as used in the present application includes human cancers including non-small cell lung carcinoma (A. Greenberg, et al., *Am. J. Respir. Cell Mol. Biol.*, 26, 558 (2002)), breast carcinoma (J. Chen, et al., *J. Biol. Chem.*, 276, 47901 (2001); B. Salh, et al., *Int. J. Cancer*, 98, 148 (2002); and S. Xiong, et al., *Cancer Res.*, 61, 1727 (2001)), gastric carcinoma (Y. D. Jung, et al., *Proc. Am. Assoc. Cancer Res.*, 43, 9 (2002)), colorectal carcinomas (S. Xiong, et al., *Cancer Res.*, 61, 1727 (2001)), and malignant melanoma (C. Denkert, et al., *Clin. Exp. Metastasis*, 19, 79 (2002)).

Inhibition of angiogenesis by suppression of TNFα has also been taught to be useful in the inhibition or prevention of metastasis (U.S. Pat. No. 6,414,150; U.S. Pat. No. 6,335,336). Furthermore, suppression of TNFα is indicated for the treatment and prevention of cachexia, a wasting syndrome experienced by about half of all cancer patients (T. Yoneda, et al., *J. Clin. Invest.*, 87, 977 (1991)).

Furthermore, inhibition of p38 kinase may be effective in the treatment of certain viral conditions such as influenza (K. Kujime, et al., *J. Immunology.*, 164, 3222-3228 (2000)), rhinovirus (S. Griego, et al. *J. Immunolog*, 165, 5211-5220 (2000)), and HIV (L. Shapiro, et al., *Proc. Natl. Acad. Sci. USA*, 95, 7422-7426, (1998)).

As used herein the term "$C_1$-$C_7$ alkyl" refers to a straight or branched, monovalent, saturated aliphatic chain of one to seven carbon atoms and includes, but is not limited to, methyl, ethyl, propyl, isopropyl, butyl, isobutyl, tert-butyl, pentyl, hexyl, and heptyl. The term "$C_1$-$C_7$ alkyl" includes within its definition the terms "$C_1$-$C_4$ alkyl".

As used herein the term "$C_1$-$C_4$ alkoxy" refers to a straight or branched alkyl chain having from one to four carbon atoms attached to an oxygen atom. Typical $C_1$-$C_4$ alkoxy groups include methoxy, ethoxy, propoxy, isopropoxy, butoxy, tert-butoxy and the like.

As used herein the term "halo" refers to a chlorine, bromine, iodine or fluorine atom, unless otherwise specified herein.

As used herein the term "$C_1$-$C_4$ alkyhalo" refers to a $C_1$-$C_4$ alkyl substituted with up to five halo atoms. Typical $C_1$-$C_4$ alkylhalo groups include methylhalo, trifluoromethyl, ethylhalo, bisfluoromethyl ethyl, propylhalo, isopropylhalo, butylhalo, tert-butylhalo and the like.

As used herein the term "$C_3$-$C_6$ cycloalkyl" means a fully saturated ring comprising carbon and hydrogen atoms and includes cyclopropyl and cyclobutyl.

Certain classes of compounds of Formula I are preferred $p3^8$ kinase inhibitors. The following paragraphs describe such preferred classes:

a) Z is

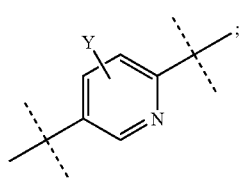

b) X is

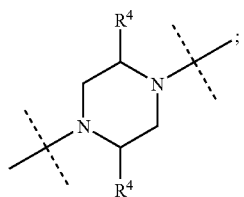

c) R⁴ is hydrogen;
d) Y is methyl;
e) $R^1$ is $C_1$-$C_7$ alkyl;
f) $R^1$ is tert-butyl;
g) $R^2$ is phenyl or pyridinyl, each optionally substituted with methyl;
h) $R^2$ is 4-tolyl;
i) $R^3$ is phenyl or thienyl each optionally substituted with a first substituent selected from the group consisting of: halo, cyano, $C_1$-$C_4$ alkyl, $C_1$-$C_4$ alkylhalo and $C_1$-$C_4$ alkoxy, and optionally further substituted with a second substituent selected from the group of $C_1$-$C_4$ alkyl and halo;
j) $R^3$ is phenyl substituted with a first substituent selected from the group consisting of halo, and further substituted with a second substituent selected from the group of $C_1$-$C_4$ alkyl and halo;
k) The compound of Formula I is a free base;
l) The compound of Formula I is a salt;
m) The compound of Formula I is the mesylate salt.

Preferred embodiments of the invention include all combinations of paragraphs a)-m). Other preferred compounds of Formula I are those where X is as described in paragraph b); $R^1$ is as described in paragraph e); $R^2$ is as described in paragraph g); and $R^4$ is as described in paragraph c).

It is also preferred that X is as described in paragraph b); $R^1$ is as described in paragraph f); $R^2$ is as described in paragraph h); $R^3$ is as described in paragraph i); and $R^4$ is as described in paragraph c).

It is particularly preferred that X is as described in paragraph b); $R^2$ is phenyl substituted in the 4-position with $C_1$-$C_4$ alkyl.

It is most preferred that X is as described in paragraph b).

The following compound is also most especially preferred:

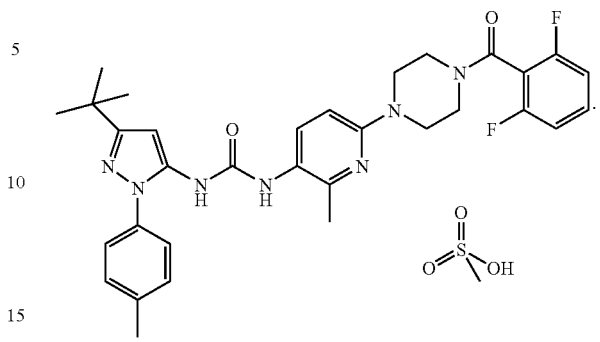

The compounds of the present invention may be prepared by a variety of procedures, some of which are illustrated in the Schemes below. It will be recognized by one of skill in the art that the individual steps in the following schemes may be varied to provide the compounds of Formula I. The particular order of steps required to produce the compounds of Formula I is dependent upon the particular compound being synthesized, the starting compound, and the relative liability of the substituted moieties. Some substituents have been eliminated in the following schemes for the sake of clarity and are not intended to limit the teaching of the schemes in any way.

Compounds of Formula I and intermediates thereof may be prepared as illustrated in the following scheme wherein $R^1$, $R^2$, and X are as previously defined:

SCHEME 1

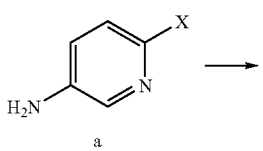

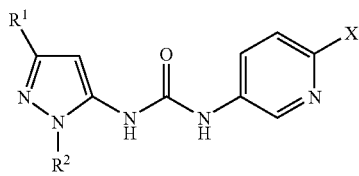

Formula I

Amine (a) is reacted with an appropriate isocyanate or carbamate, such as pyrazolyl-2,2,2-trichloroethyl carbamate, to provide compounds of Formula I. For example, a solution of the amine (1 equiv.), trichloroethyl carbamate (1 equiv.) and a suitable base such as diisopropylethylamine (2 equiv.), or potassium carbonate, in a suitable solvent, such as acetonitrile or dimethylsulfoxide (DMSO) is heated. The desired compound may then be isolated and, if necessary and desired, purified using techniques well known in the art, such as chromatography, to provide the compound of Formula I.

The requisite amines are prepared as illustrated below in Scheme 2 wherein X is as previously defined:

SCHEME 2

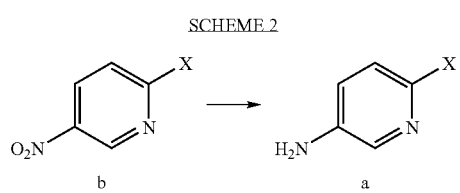

The nitro moiety (b) is reduced under standard reducing conditions, for example with hydrogen in the presence of a palladium catalyst, or sodium borohydride in the presence of nickel(II) chloride hexahydrate in a suitable solvent such as lower alkanols, or ethyl acetate, to provide the corresponding amine (a). Such reduction steps are well known and appreciated in the art. See Larock, R., "*Comprehensive Organic Transformations*," 412, VCH Publishing, Inc., New York, 1989.

The requisite nitro compounds are prepared as illustrated in Scheme 3 below, wherein Hal is Cl or F, and X' is C(O)R³ or a suitable protecting group PG:

Scheme 3

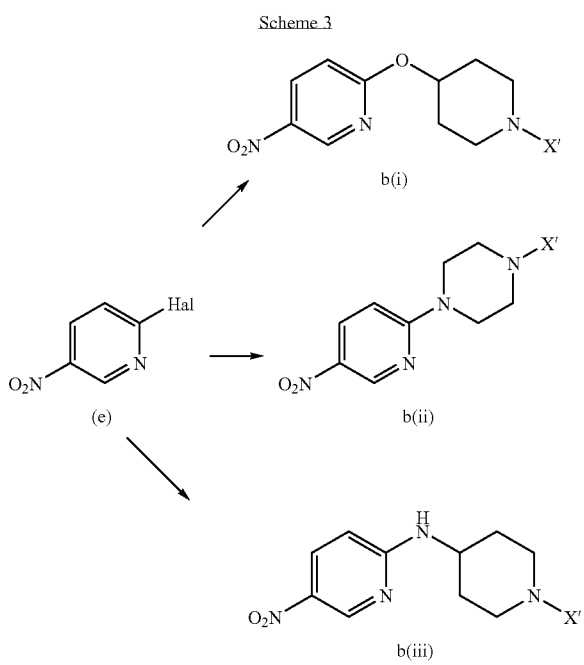

2-halo-4-nitro-pyridine (e) in a suitable organic solvent, such as THF is reacted with an appropriate 4-hydroxy piperidine and sodium hydride or triphenylphosphine to provide the corresponding substituted piperidine b(i). Alternatively, 2-halo-4-nitro-pyridine (e) is reacted an appropriate piperazine and a base such as potassium carbonate, sodium tert-butoxide, or triethylamine in a polar solvent, such as acetonitrile, N,N-dimethylformamide (DMF), or butanol to provide the corresponding substituted piperazine b(ii).

The amine of formula b(iii) is prepared by reacting a 2-halo-4-nitro-pyridine (e) in a suitable solvent, such as ethanol, with an appropriate aminopiperidine in the presence of a suitable base such as sodium carbonate.

The skilled artisan will appreciate that the procedures described above may be utilized in formation of pyridyl isomers contemplated in the present invention.

The required pyrazolyl carbamates may be prepared as described in the following scheme, where R¹ and R² are as previously defined:

SCHEME 4

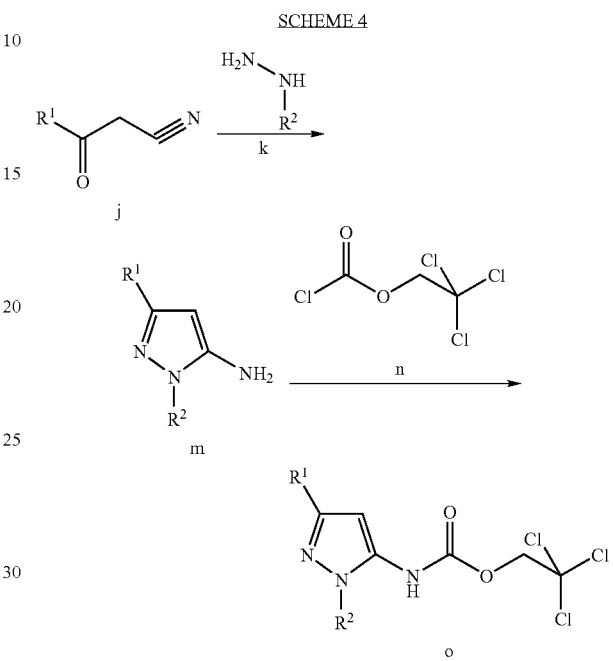

3-aminopyrazoles (m) are formed through conditions well known in the art; Larock, R., "*Comprehensive Organic Transformations*," 79, VCH Publishing, Inc., New York, 1989. For example, an α-cyanoketone (j) and a suitable hydrazine or hydrazine salt (k) in a suitable organic solvent, such as ethanol, are reacted at an elevated temperature. The resulting pyrazole (m) may be purified using standard techniques, such as chromatography on a silica gel column.

2,2,2-Trichloroethyl chloroformate (n) is reacted with an appropriately substituted 3-aminopyrazole (m) and a base, for example sodium carbonate, potassium carbonate or pyridine, in a suitable solvent, e.g., THF or water/ethyl acetate, to provide the corresponding 2,2,2-trichloroethyl carbamate (o). The skilled artisan will appreciate that the corresponding carbamate may be prepared by reacting the 3-aminopyrazole with other active carbonates.

Compounds of Formula I(i) may be prepared as demonstrated in Scheme 5 below wherein R¹, R², R³, and PG are as previously defined, Z is O, N, or a bond, and R⁵ is C or N:

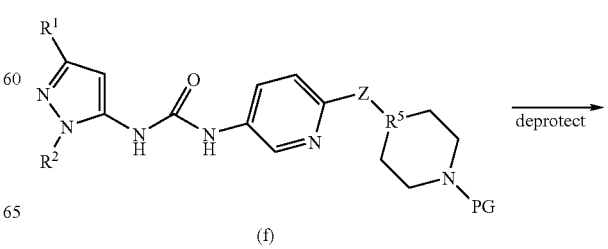

-continued

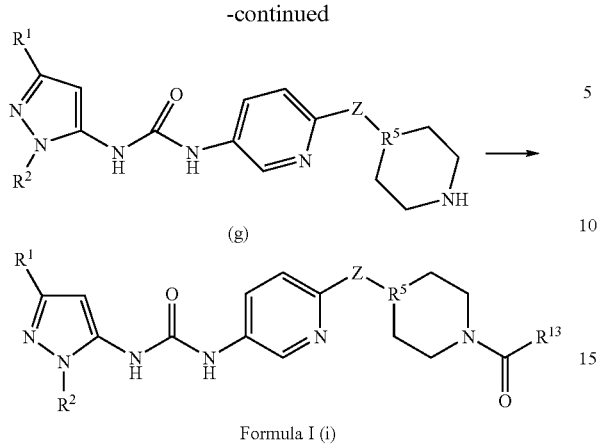

(g)

Formula I (i)

The compound of Formula (f) is deprotected under conditions well known in the art. For example, when the protecting group is tert-butoxy carbonyl, a compound of Formula (f) is dissolved in a suitable organic solvent or solvent mixture, such as dichloromethane, and treated with an acid, such as hydrochloric acid in dioxane or trifluoroacetic acid. Deprotection of N-protected-piperidine substituted urea (i) provides the substituted piperidine (g), which is reacted with a substituted carboxylic acid under standard coupling conditions for organic acids and organic amines in the presence of a coupling agent, such as N-(3-dimethylaminopropyl)-N'-ethylcarbodiimide hydrochloride (EDCI) or dicyclohexylcarbodiimide (DCC), a catalytic amount of 4-dimethylaminopyridine (DMAP) and 1-hydroxybenzotriazole (HOBt) or O-(7-azabenzotriazole-1-yl)-N,N,N',N'-tetramethyluronium hexafluorophosphate (HATU), or triethylamine in a suitable solvent, such as methylene chloride or acetonitrile, to provide Formula I (i). The skilled artisan will appreciate that examples of Formula I(i) may be prepared by beginning with other protected piperidines, including different N-protecting groups, such as formyl, which may require other deprotection procedures to form intermediate (g).

A suitable amino protecting group "Pg", such as a tert-butoxycarbonyl (BOC) moiety, may be utilized if necessary or desired. Techniques for the introduction of these groups are well known to the skilled artisan. The skilled artisan will appreciate that the protecting groups may be removed at any convenient point in the synthesis of the compounds of the present invention. Methods for introducing and removing nitrogen and oxygen protecting groups are well known in the art; see, for example, Greene and Wuts, *Protective Groups in Organic Synthesis*, 3$^{rd}$ Ed., John Wiley and Sons, New York, (1999).

The skilled artisan will also appreciate that not all of the substituents in the compounds of Formula I will tolerate certain reaction conditions employed to synthesize the compounds. These moieties may be introduced at a convenient point in the synthesis, or may be protected and then deprotected as necessary or desired.

The abbreviations, symbols and terms used in the examples and assays have the following meanings: n-BuOH=n-butanol, DCC=dicyclohexylcarbodiimide, DIEA=N,N-di-isopropylethylamine, DMSO=dimethylsulfoxide, DMF=N,N-dimethylformamide, h=hour(s), HOBt=1-hydroxybenzotriazole, LDA=lithium diisopropylamide, EDCI=1-(3-dimethylaminopropyl)-3-ethylcarbodiimide hydrochloride, EtOAc=ethyl acetate, EtOH ethanol, Et$_2$O=diethyl ether, MeOH=methanol, NaBH(OAc)$_3$=sodium triacetoxyborohydride, TBAF=tetrabutyl ammonium fluoride, Tf$_2$O=trifluoromethanesuflonic anhydride, and THF=tetrahydrofuran.

PREPARATIONS

Preparation 1

2-Chloro-4-methyl-5-nitro-pyridine

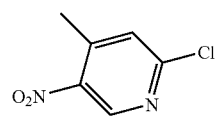

Dissolve 4-methyl-5-nitro-pyridin-2-ylamine (3.0 mmol, 0.5 g) in 0.5 mL of sulfuric acid. Add 7.6 mL of water and cool the solution down to 0° C. Add sodium nitrite (4.5 mmol, 0.3 g) and stir the mixture for two hours, allowing to reach room temperature. Dilute with water and add aq. sodium hydroxide solution 10% until basic pH. Extract in ethyl acetate and wash combined organic layers with saturated aq. sodium chloride solution. Dry over sodium sulfate, filter, and concentrate under reduced pressure to give 4-methyl-5-nitro-pyridin-2-ol. MS(ES): m/z=155 [M+H].

Add phosphorus oxychloride (0.6 mmol, 0.05 mL) and phosphorus pentachloride (0.6 mmol, 0.12 g) over 4-methyl-5-nitro-pyridin-2-ol (1.9 mmol, 0.3 g). Stir at 120° C. for 1.5 hours. Cool down, add ice-water and extract in CH$_2$Cl$_2$. Wash combined organic layers with saturated aq. sodium chloride solution. Dry over sodium sulfate, filter, and concentrate under reduced pressure to give 2-chloro-4-methyl-5-nitro-pyridine.

Preparation 2

2,3-Dichloro-5-nitro-pyridine

Place 5-nitro-pyridin-2-ol (20 g, 143 mmol) in concentrated HCl (100 mL). Heat to 50° C. and then dropwise add potassium chlorate (6.13 g, 50 mmol) dissolved in water (100 mL). Stir at 50° C. for 30 min. Cool the reaction in an ice bath. Filter off the solid and wash with water. Dry thoroughly to yield 21.13 g (85%) of 3-chloro-5-nitro-pyridin-2-ol. MS(ES): m/z=173 [M+H].

Place phosphorus oxychloride (11.28 mL, 121 mmol) in a round-bottom flask and cool to 0° C. Add quinoline (7.15 mL, 60.5 mmol) followed by 3-chloro-5-nitro-pyridin-2-ol (21.13 g, 121 mmol) in portions. Heat reaction to 120° C. for 2 hours. Pour reaction onto ice and triturate with water. Filter off the solid and wash with water. Dry thoroughly to yield 19.95 g (86%) of the title compound: $^1$H NMR δ$_H$ (400 MHz, DMSO) 9.20 (s, 1H), 8.97 (s, 1H).

Preparation 3

4-(5-Amino-6-methyl-pyridin-2-yl)-piperazine-1-carboxylic acid tert-butyl ester

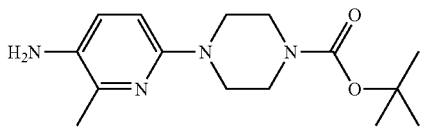

Mechanically stir mixture of 6-chloro-2-methyl-3-nitro-pyridine (Asymchem, 25.00 g, 144.9 mmol), tert-butyl 1-piperazinecarboxylate (29.68 g, 159.4 mmol), and triethylamine (23.2 mL, 167 mmol) in n-BuOH (250 mL) at 50° C. under nitrogen for 4 hours, at 65° C. for 2 hours, then at room temperature overnight. Add additional tert-butyl 1-piperazinecarboxylate (1.5 g), and heat the reaction at 65° C. for 4 hours. Cool the resulting slurry to 30° C. then add hexanes (75 mL). Cool the slurry to room temperature over 1 hour, then add water (150 mL). Allow the slurry to stand for 45 min then filter. Wash the cake with water (4×100 mL) then hexanes (100 mL) and air-dry overnight to yield 4-(6-methyl-5-nitro-pyridin-2-yl)-piperazine-1-carboxylic acid tert-butyl ester as bright yellow crystals (46.30 g, 99% yield, MS(ES): m/z=267 [M+H−$C_4H_8$]).

Mix a slurry of 4-(6-methyl-5-nitro-pyridin-2-yl)-piperazine-1-carboxylic acid tert-butyl ester (46.00 g, 142.7 mmol) in THF (750 mL) at room temperature with Pd/C (5% Aldrich, 3.04 g, 1.43 mmol) then place under a hydrogen atmosphere (Parr shaker, 40-45 psi) for 6 hours. Add MeOH (250 mL), and subject the slurry to an atmosphere of hydrogen for 4 hours at room temperature. Add additional catalyst (3.04 g), then place the mixture under hydrogen for 7 hours. Filter the mixture through a pad of Celite 521®, washing with THF and MeOH then concentrate under reduced pressure to provide the title compound a pale pink solid. (41.58 g, 99% yield, MS(ES+): m/z=293 [M+H]).

Prepare the following compounds in a manner substantially analogous to the procedures described above.

TABLE

| Preparation | Compound | MS(ES): m/z [M + H] |
|---|---|---|
| Preparation 4 | 4-(5-Amino-pyridin-2-yl)-piperazine-1-carboxylic acid tert-butyl ester | 293 |
| Preparation 5 | 4-(5-Amino-3-methyl-pyridin-2-yl)-piperazine-1-carboxylic acid tert-butyl ester | 293.2 |

Preparation 6

4-(5-amino-pyridin-2-yl)-piperazine-1-carboxylic acid tert-butyl ester

Place 2-chloro-5-nitro-pyridine (1.0 g, 6.31 mmol), piperazine-1-carboxylic acid tert-butyl ester (1.76 g, 9.45 mmol), and triethylamine (1.76 mL, 12.6 mmol) in n-butanol (20 mL). Heat to 120° C. for 17 hours. Cool to room temperature and add ethyl acetate and water. Separate organic layer and wash with water and saturated aq. sodium chloride. Collect organic layer, dry over $Mg_2SO_4$, filter, and concentrate under reduced pressure. Subject residue to silica gel chromatography eluting with 20% EtOAc:hexane to yield 1.14 g (58%) of 4-(5-nitro-pyridin-2-yl)-piperazine-1-carboxylic acid tert-butyl ester. MS(ES): m/z=309 [M+H].

Place 4-(5-nitro-pyridin-2-yl)-piperazine-1-carboxylic acid tert-butyl ester (1.14 g, 3.70 mmol) in 1:1 EtOAc:MeOH (20 mL). Add 10% Pd on carbon using EtOAc (5 mL). Purge the reaction and then add hydrogen. Repeat the purge/fill cycle twice and place the reaction under a balloon of hydrogen and stir at room temperature for 20 hours. Filter the reaction through a pad of Celite® and wash the filter cake with EtOAc. Collect the filtrate and concentrate under reduced pressure to yield 1.01 g (98%) of the title compound. MS(ES): m/z=279 [M+H].

Prepare the following compounds in a manner substantially analogous to the procedures described above.

TABLE

| Preparation | Compound | MS(ES): m/z [M + H] |
|---|---|---|
| Preparation 7 | 4-(5-amino-3-methyl-pyridin-2-yl)-piperazine-1-carboxylic acid tert-butyl ester | 293.4 |

Preparation 8

4-(5-amino-3-chloro-pyridin-2-yl)-piperazine-1-carboxylic acid tert-butyl ester Place 2,3-dichloro-5-nitro-pyridine (2.0 g, 10.36 mmol), piperazine-1-carboxylic acid tert-butyl ester (2.12 g, 11.40 mmol), and potassium carbonate (1.72 g, 12.43 mmol) in DMF (20 mL). Heat to 80° C. for 2.5 days. Cool to room temperature and add ethyl acetate and water. Separate organic layer and wash with water and saturated aq. sodium chloride. Collect organic layer, dry over $Mg_2SO_4$, filter, and concentrate under reduced pressure. Subject residue to silica gel chromatography eluting with 20% EtOAc:hexane to yield 3.29 g (93%) of 4-(3-chloro-5-nitro-pyridin-2-yl)-piperazine-1-carboxylic acid tert-butyl ester. MS(ES): m/z=341 [M+H].

Place 4-(3-chloro-5-nitro-pyridin-2-yl)-piperazine-1-carboxylic acid tert-butyl ester (3.09 g, 9.01 mmol) in methanol (50 mL). Add nickel(II) chloride hexahydrate (10.7 g, 45.1 mmol) and cool the reaction to 0° C. Add sodium borohydride (5.11 g, 135.15 mmol) in portions and stir at 0° C. for 2 hours. Add $CH_2Cl_2$ and filter through a pad of Celite®. Wash filter cake with $CH_2Cl_2$ and collect filtrate. Add saturated aq. sodium bicarbonate solution to the filtrate and separate organic layer. Extract aqueous layer with $CH_2Cl_2$ (2×30 mL). Combine organic extracts, dry over $Mg_2SO_4$, filter, and concentrate under reduced pressure. Subject residue to silica gel chromatography eluting with 0-70% EtOAc:hexane to yield 1.77 g (63%) of the title compound. MS(ES): m/z=311.2 [M−H].

Preparation 9 rac-[(trans)-4-(5-Amino-3-methyl-pyridin-2-yl)-2,5-dimethyl-piperazin-1-yl]-cyclopropyl-methanone

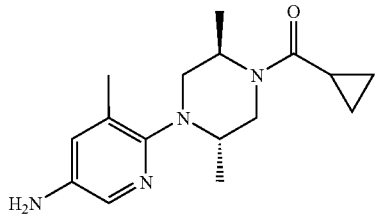

Dissolve trans-2,5-dimethylpiperazine (500 mg, 4.37 mmol, 1.0 equiv) in 15 mL of anhydrous dichloromethane. Add di-tert-butyl dicarbonate (953 mg, 4.37 mmol, 1.0 equiv) dissolved in 5 mL of dichloromethane. Stir at room temperature for 20 hours. Filter white solid to yield 430 mg of N—BOC-trans-2,5-dimethylpiperazine (50% yield). $^1$H NMR (methanol-d4) d ppm 4.11 (m, 1H); 3.55 (dd, J=13.6, 1.7 Hz, 1H), 3.23 (dd, J=13.6, 4.0 Hz, 1H), 3.12 (m, 1H), 3.00 (dd, J=12.7, 2.9 Hz, 1H), 2.49 (m, 1H), 1.46 (s, 9H), 1.24 (d, J=7.6, 3H), 1.15 (d, J=6.8 Hz, 3H).

Dissolve 2-chloro-3-methyl-5-nitropyridine (310 mg, 1.82 mmol, 1.0 equiv) and N—BOC-trans-2,5-dimethylpiperazine (397 mg, 2.0 mmol, 1.1 equiv) in 5 mL of anhydrous DMF, add potassium carbonate (251 mg, 1.82 mmol, 1.0 equiv) and stir the mixture for 20 hours at 80° C. Pour the solution in a 1:1 v/v mixture of EtOAc and iced water. Extract the aqueous phase with EtOAc (2×20 mL) and wash the combined organic layers with water (3×20 mL) and saturated aq. sodium chloride (30 mL). Dry the organic solution over sodium sulfate and concentrate under reduced pressure to obtained a crude rac-(trans)-2,5-dimethyl-4-(3-methyl-5-nitro-pyridin-2-yl)-piperazine-1-carboxylic acid tert-butyl ester. MS(ES+): m/z=251.2 (M+H).

Add HCl 4 M in dioxane (4.2 mL) to rac-(trans)-2,5-dimethyl-4-(3-methyl-5-nitro-pyridin-2-yl)-piperazine-1-carboxylic acid tert-butyl ester (0.15 g, 0.43 mmol) at room temperature and stir. After one hour concentrate under reduced pressure to give 0.138 g of rac-(trans)-2,5-dimethyl-1-(3-methyl-5-nitro-pyridin-2-yl)-piperazine di-hydrochloric salt as a white solid. (quantitative). MS(ES): m/z=251.2 [M+H].

Add cyclopropyl carboxylic acid (56 □L, 0.7 mmol) to a solution of EDCI (0.147 g, 0.77 mmol), HOBt (0.10 g, 0.77 mmol), rac-(trans)-2,5-dimethyl-1-(3-methyl-5-nitro-pyridin-2-yl)-piperazine di-hydrochloric salt (0.16 g, 0.64 mmol) in CH$_2$Cl$_2$ (5 mL) follow by DIEA (0.22 mL, 1.28 mmol) at room temperature under N$_2$ atmosphere. After one hour, concentrate to give a residue. Subject residue to silica gel chromatography eluting with hexane:AcOEt 50-70% to give 0.114 g rac-cyclopropyl-[(trans)-2,5-dimethyl-4-(3-methyl-5-nitro-pyridin-2-yl)-piperazin-1-yl]-methanone (56% yield). MS(ES): m/z=319.1 [M+H].

Add NH$_4$COOH (0.23 g, 3.5 mmol) to rac-cyclopropyl-[(trans)-2,5-dimethyl-4-(3-methyl-5-nitro-pyridin-2-yl)-piperazin-1-yl]-methanone (0.114 g, 0.35 mmol) and Pd/C 10% (0.043 g) in EtOH (5 mL) under N$_2$ atmosphere and heat at 80° C. After 2 hours let reaction mixture cool down and filter through Celite®. Concentrate under reduced pressure to give 0.1 g the title compound (quantitative). MS(ES): m/z=289.3 [M+H].

Preparation 10

1-[4-(5-Amino-4-methyl-pyridin-2-yl)-piperazin-1-yl]-2,2-dimethyl-propan-1-one

Stir a solution of 2-chloro-4-methyl-5-nitro-pyridine (0.85 mmol, 0.15 g), 2,2-dimethyl-1-piperazin-1-yl-propan-1-one hydrochloride (0.94 mmol, 0.16 g) and triethylamine (2.12 mmol, 0.3 mL) in a sealed tube at 80° C. overnight. Cool down the mixture to room temperature, add CH$_2$Cl$_2$ and wash with saturated aq. sodium chloride. Dry over sodium sulfate, filter, and concentrate under reduced pressure to give 2,2-dimethyl—[4-(4-methyl-5-nitro-pyridin-2-yl)-piperazin-1-yl]-propane-1-one. Subject residue to silica gel chromatography eluting with hexanes/ethyl acetate in a gradient (from 30% up to 60%). MS(ES): m/z=307 [M+H].

Add ammonium formate (1.55 mmol, 0.1 g) and palladium (Carbon) 10% (0.031 mmol) over a solution of 2,2-dimethyl-1-[4-(4-methyl-5-nitro-pyridin-2-yl)-piperazin-1-yl]-propan-1-one (0.31 mmol, 0.09 g) in 2 mL of ethanol. Stir the solution for an hour at 90° C. Cool down and filter through a pad of Celite®, and concentrate under reduced pressure. Residue can be used without further purification. MS(ES): m/z=277 [M+H].

Prepare the following compound in a manner substantially analogous to the second procedure described above.

TABLE

| Preparation | Compound | MS(ES): m/z [M + H] |
|---|---|---|
| Preparation 11 | [4-(5-Amino-4-methyl-pyridin-2-yl)-piperazin-1-yl]-(1-methyl-cyclopropyl)-methanone | 275 |

Preparation 12

1-[4-(5-Amino-4-chloro-pyridin-2-yl)-piperazin-1-yl]-2,2-dimethyl-propan-1-one

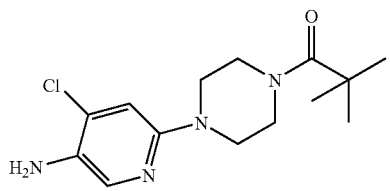

Step A: Stir a solution of 2,4-dichloro-pyridine (6.7 mmol, 1 g), N-Boc piperazine (8.1 mmol, 1.5 g), sodium tert butoxide (9.5 mmol, 0.9 g), palladium (II) acetate (0.7 mmol, 0.15 g) and 2-(di-tbutylphosphino)biphenyl (0.7 mmol, 0.2 g) dissolved in toluene under nitrogen at 100° C. for 4 hours. Cool down to room temperature and add water. Extract in ethyl acetate washing the organic layer with water and saturated aq. sodium chloride. Dry organic layer over sodium sulfate, filter, and concentrate under reduced pressure to give 4-(4-chloro-pyridin-2-yl)-piperazine-1-carboxylic acid tert-butyl ester as a residue. Subject residue to silica gel chromatography eluting with hexanes/ethyl acetate in gradient (from 10% to 50%). MS(ES): m/z=298 [M+H].

Step B: Treat a room temperature solution of 4-(4-chloro-pyridin-2-yl)-piperazine-1-carboxylic acid tert-butyl ester (0.6 g, 1.9 mmol) in $CH_2CL_2$ (4 mL) with HCl (4 N solution in dioxane, 1.5 mL, 5.9 mmol) resulting in a slight exotherm. Stir the mixture for 3 hours, add additional HCl (4 N solution in dioxane, 1.5 mL, 5.9 mmol), and stir overnight. Concentrate under reduced pressure to afford 1-(4-chloro-pyridin-2-yl)-piperazine hydrochloride, then titurate with $Et_2O$ (0.43 g). LCMS ES+(m/z) 198 [M+H]).

Step C: Stir 1-(4-chloro-pyridin-2-yl)-piperazine hydrochloride (2.2 mmol, 0.4 g), triethylamine (7.6 mmol, 1.1 mL) in 13 mL of $CH_2Cl_2$ and pivaloyl chloride (2.2 mmol, 0.3 mL) overnight at room temperature. Add $CH_2Cl_2$ and wash with saturated aq. sodium chloride and water. Dry over sodium sulfate, filter, and concentrate under reduced pressure to give 1-[4-(4-chloro-pyridin-2-yl)-piperazin-1-yl]-2,2-dimethyl-propan-1-one. MS(ES): m/z=282 [M+H].

Step D: Dissolve 1-[4-(4-chloro-pyridin-2-yl)-piperazin-1-yl]-2,2-dimethyl-propan-1-one (1.6 mmol, 0.4 g) in sulfuric acid (2.3 mL) and cool the solution down to 0° C. Add potassium nitrate (1.6 mmol, 0.2 g) and stir the mixture allowing to reach room temperature overnight. Dilute the mixture with water and add sodium hydroxide 10% until basic pH. Extract in ethyl acetate. Dry over sodium sulfate, filter, and concentrate under reduced pressure to give a residue of 1-[4-(4-chloro-5-nitro-pyridin-2-yl)-piperazin-1-yl]-2,2-dimethyl-propan-1-one. Subject residue to silica gel chromatography eluting with a mixture hexanes/ethyl acetate as (from 30% up to 60%). MS(ES): m/z=327 [M+H].

Step E: Add (4.5 mmol, 0.8 g) of sodium dithionite, over 1-[4-(4-chloro-5-nitro-pyridin-2-yl)-piperazin-1-yl]-2,2-dimethyl-propan-1-one (0.9 mmol, 0.3 g) in 22 mL of 1:1 mixture of tetrahydrofuran and water and 4 mL of ammonia. Stir the solution for 2 hours at room temperature. Concentrate under reduce pressure and extract the residue in ethyl acetate. Dry over sodium sulfate, filter, and concentrate under reduced pressure to give a residue that is used without further purification. MS(ES): m/z=297 [M+H].

Prepare the following compound using procedures substantially analogous Steps C-E described above.

TABLE

| Preparation | Compound | MS(ES): m/z [M + H] |
|---|---|---|
| Preparation 13 | 1-[4-(5-Amino-3-trifluoromethyl-pyridin-2-yl)-piperazin-1-yl]-2,2-dimethyl-propan-1-one | 331 |

Preparation 14

[4-(5-Amino-6-methyl-pyridin-2-yl)-piperazine-1-yl] (2,6-difluoro-phenyl)-methanone

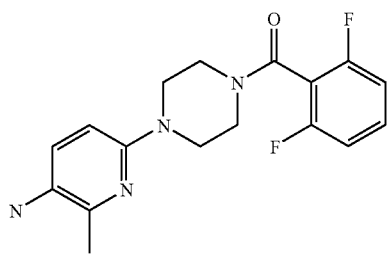

Charge acetic acid (5 L) to a 22 L flask. Place the reaction in an ice-water bath. Add piperazine (355.00 g, 2.0 equiv; 4.06 moles) in portions with stirring, and increase temperature to ~40° C. Add another 5 L of acetic acid. Stir until mixture becomes a solution. Adjust cooling bath to ~13° C. Add 2,6-difluorobenzoyl chloride (355.00 g, 1.00 equiv; 2.01 moles; 253.39 mL) drop wise over a 2 hours period, while maintaining reaction temperature at approximately 13-15° C. Stir overnight. Concentrate under reduced pressure and dissolve residue in 2 L of ice water. Cool flask in an ice water bath. Add 5 N NaOH to adjust pH to 7.5 while maintaining the reaction temperature below 30° C. Filter at ~10° C. Extract product from filtrate with dichloromethane (4×2 L). Remove solvent under reduced pressure. Dissolve the solid in 1.5 L of methanol at room temperature and filter. Concentrate the methanol solution, then solvent exchange with toluene 2.0 L, afforded pure product. Filter to obtain (2,6-difluorophenyl)-piperazin-1-yl-methanone. Concentrate filtrate and filter again to obtain additional product (total 400 g).

Charge (2,6-difluoro-phenyl)-piperazin-1-yl-methanone (1.07 equiv, 1.55 moles, 350.00 g), methanol (37.06 moles, 1.50 L, 1.19 kg), triethylamine (1.79 moles, 250.00 mL, 181.50 g), 6-chloro-2-methyl-3-nitro-pyridine (1.00 equiv, 1.45 moles, 250.00 g) to a 5 L flask with over head stirrer. Stir the reaction mixture at room temperature for 0.5 hours. Slowly heat to 60° C., and continue to stir at 60° C. overnight. Add water (750 mL) drop wise while maintaining the temperature at 60° C. Allow mixture to cool to room temperature. Filter and wash cake with 2:1 methanol/water 150 mL, then twice with MTBE. Dry under reduced pressure at 45° C. to obtain (2,6-difluoro-phenyl)-[4-(6-methyl-5-nitro-pyridin-2-yl)-piperazin-1-yl]-methanone as a yellow solid (535 g).

Charge (2,6-difluoro-phenyl)-[4-(6-methyl-5-nitro-pyridin-2-yl)-piperazin-1-yl]-methanone (1.00 equiv, 1.44 moles, 520.00 g), methanol (197.66 moles, 8.00 L, 6.33 kg), and THF wetted 5% palladium on carbon (75.00 g) to a three gallon autoclave. Hydrogenate the reaction at 50 psi at room temperature while maintaining a temperature below 30° C. After 0.5 hours, cool to 26° C., and maintain for 2 hours. Filter and concentrate under reduced pressure. Filter to obtain solids, rinse with methanol then heptanes. An additional filtration yields a second batch of [4-(5-amino-6-methyl-pyridin-2-yl)-piperazin-1-yl]-(2,6-difluoro-phenyl)-methanone. Dry under reduced pressure at 45° C. (445 g).

Preparation 15

[4-(5-Amino-3-methyl-pyridin-2-yl)-piperazin-1-yl]-(2,6-difluoro-phenol)-methanone Treat a slurry of 2-chloro-3-methyl-5-nitro-pyridine (27.00 g, 0.156 mol) and piperazine-1-carboxylic acid tert-butyl ester (32.03 g, 0.172 mol) in anhydrous DMF (270 mL) with $K_2CO_3$ (34.55 g, 0.250 mol), then heat the reaction mixture at 80° C. under $N_2$ overnight. Pour the resulting reaction mixture into 1/1 EtOAc/$H_2O$ (3,000 mL), separate the layers, then extract the aqueous layer with EtOAc (1,000 mL). Wash the combined organics with saturated aq. sodium chloride (3×1,000 mL each), dry over $MgSO_4$, filter, then concentrate under reduced pressure to give a yellow solid. Slurry the yellow solid in hexanes/EtOAc, then recover the resulting solid by vacuum filtration. Wash with hexanes and vacuum filter to give (42.84 g) of 4-(3-methyl-5-nitro-pyridin-2-yl)-piperazine-1-carboxylic acid tert-butyl ester as a yellow solid. Concentrate the filtrate under reduced pressure to give a yellow solid. Slurry the yellow solid in hexanes, then recover the resulting solid by vacuum filtration, washing with hexane and drying under vacuum filtration to give an additional (5.38 g) of 4-(3-methyl-5-nitro-pyridin-2-yl)-piperazine-1-carboxylic acid tert-butyl ester compound as a yellow solid (48.22 g, 95.9% yield). $^1$H NMR (400 MHz, CDCl$_3$) δ 8.96 (d, 1H), 8.14 (d, 1H), 3.57 (m, 4H), 3.41 (m, 4H), 2.36 (s, 3H), 1.48 (s, 9H); TOF-MS [ES+, M+H] Obs. m/z 323.1723, Calc. m/z 323.1719; Anal. Calcd. For C$_{15}$H$_{22}$N$_4$O$_4$: C, 55.88; H, 6.87; N, 17.37. Found C, 55.94; H, 6.87; N, 17.14.

Add a solution of HCl 4M in dioxane (4 equiv) to a solution of 4-(3-Methyl-5-nitro-pyridin-2-yl)-piperazine-1-carboxylic acid tert-butyl ester (7.77 g, 24.13 mmol) in DCM (73 mL). Stir mixture at room temperature overnight. Add 2 more equiv of the HCl in dioxane solution. After no starting material is detected by LCMS, filter solid and dry under reduced pressure to obtain 6.91 g of 1-(3-methyl-5-nitro-pyridin-2-yl)-piperazine hydrochloride as a yellowish solid (97% yield). ES+(m/z): 259 [M+1].

Add triethylamine drop wise (3 equiv) to a suspension of 1-(3-methyl-5-nitro-pyridin-2-yl)-piperazine; hydrochloride (6.91 g, 24.13 mmol) in DCM (120 mL). Add 2,6-difluorobenzoylchloride (1 equiv.) Stir the mixture at room temperature overnight. Add additional 2,6-difluorobenzoylchloride (1.6 mL) and triethylamine (1.5 equiv.) to run reaction to completion. Allow the reaction to stand overnight. Dilute with DCM and extract several times with water. Dry the organic layer over Na$_2$S$_2$O$_4$, filter, and remove solvent under reduced pressure. Wash solid several times with hexane to obtain. 8.08 g of (2,6-difluoro-phenyl)-[4-(3-methyl-5-nitro-pyridin-2-yl)-piperazin-1-yl]-methanone (93% yield). ES+(m/z): 363 [M+1]

Add Na$_2$S$_2$O$_4$ (10 equiv.) and aqueous ammonia (3 mL/mmol, 32%) to a solution of (2,6-difluoro-phenyl)-[4-(3-methyl-5-nitro-pyridin-2-yl)-piperazin-1-yl]-methanone (3 g, 8.29 mmol) in THF/H$_2$O (166 mL, 1:1). Stir for 30 min., then separate layers. Extract the aqueous layer with DCM, EtOAc and isopropyl alcohol/EtOAc. Combine organic layers and dry over Na$_2$SO$_4$, filter and remove solvent under reduced pressure. Subject crude to a Varian™ SCX column and wash the column with MeOH and then flush off the product with 2 M NH$_3$ in MeOH to obtain 1.2 g of [4-(5-amino-3-methyl-pyridin-2-yl)-piperazin-1-yl]-(2,6-difluoro-phenyl)-methanone (44% yield). ES+(m/z): 333 [M+1]

Preparation 16

4-(5-Amino-6-methyl-pyridin-2-yloxy)-piperidine-1-carboxylic acid tert-butyl ester

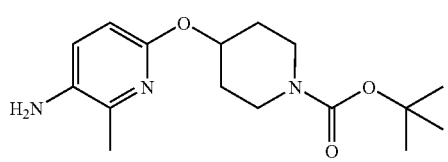

Add diisopropyl azodicarboxylate (3.0 mL, 15.5 mmol) dropwise to a cold mixture of 6-methyl-5-nitro-pyridin-2-ol (1.54 g, 10.0 mmol), 4-hydroxy-piperidine-1-carboxylic acid tert-butyl ester (2.05 g, 10.0 mmol), and triphenylphosphine (4.02 g, 15.3 mmol) in THF (25 mL) at 0° C. After addition is complete, remove cooling bath and stir the reaction mixture at 22° C. overnight. Concentrate under reduced pressure. Subject residue to silica gel chromatography eluting with hexanes and ethyl acetate to provide 4-(6-Methyl-5-nitro-pyridin-2-yloxy)-piperidine-1-carboxylic acid tert-butyl ester as a colorless oil (2.69 g, 80% yield). MS(ES): m/z=338.2 [M+H].

Stir a mixture of 4-(6-methyl-5-nitro-pyridin-2-yloxy)-piperidine-1-carboxylic acid tert-butyl ester (2.69 g, 8.0 mmol) and 10% palladium on carbon (1.0 g) in ethanol (60 mL) at 22° C. under hydrogen for 2 hours. Filter off the palladium catalyst. Concentrate the filtrate to give a colorless oil. Subject residue to silica gel chromatography eluting with hexanes and ethyl acetate to give the title compound. (2.19 g, 89% yield). MS(ES): m/z=308.2 [M+H].

Prepare the following compound using a procedure substantially analogous to that described above.

TABLE

| Preparation | Compound | MS(ES): m/z [M + H-BOC] |
| --- | --- | --- |
| Preparation 17 | 4-(5-Amino-3-methyl-pyridin-2-yloxy)-piperidine-1-carboxylic acid tert-butyl ester | 208.2 |

Preparation 18

4-(5-Amino-pyridin-2-yloxy)-piperidine-1-carboxylic acid tert-butyl ester

Add a suspension of pre-washed NaH (0.1 g, 2.48 mmol, 60% dispersion in mineral oil) in THF (2 mL) to an ice cold solution of 4-hydroxy-piperidine-1-carboxylic acid tert-butyl ester (0.5 g, 2.48 mmol) in dry THF (3 mL). Allow mixture to stir for 20 minutes, then add 2-chloro-5-nitro-pyridine (0.36 g, 2.26 mmol) in portions. After addition is completed, remove cooling bath and stir the reaction mixture at 22° C. overnight. Cool reaction mixture with ice bath and add a saturated aq. sodium bicarbonate solution (5 mL). Distribute the reaction mixture between ethyl acetate (25 mL) and distilled water (25 mL). Isolate the aqueous phase and extract with ethyl acetate (3×35 mL). Dry the combined organic phases over sodium sulfate and concentrate under reduced pressure. Subject residue to silica gel chromatography eluting with hexanes and ethyl acetate to give 4-(5-Nitro-pyridin-2-yloxy)-piperidine-1-carboxylic acid tert-butyl ester as a white solid (0.55 g, 75% yield). MS(ES): m/z=324.2 [M+H].

Stir a mixture of 4-(5-Nitro-pyridin-2-yloxy)-piperidine-1-carboxylic acid tert-butyl ester (2.7 g, 8.35 mmol) and 10% palladium on carbon (0.5 g) in ethanol (100 mL) at room temperature under hydrogen for 4 hours. Filter to remove palladium catalyst. Concentrate the filtrate and subject the resultant colorless oil to silica gel chromatography eluting with hexanes and ethyl acetate to give the title compound as a white solid (2.11 g, 86% (ES+(m/z) 194.2 [M+H—BOC]).

Preparation 19

[4-(5-Amino-3-methyl-pyridin-2-yloxy)-piperidin-1-yl]-(2-fluoro-phenyl)-methanone

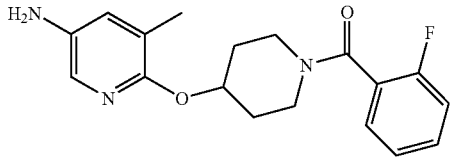

Add a suspension of pre-washed NaH (1.27 g, 31.87 mmol, 60% dispersion in mineral oil) in THF (20 mL) to an ice cold solution of 4-hydroxy-piperidine-1-carboxylic acid tert-butyl ester (6.41 g, 31.87 mmol) in dry THF (80 mL). Allow the mixture to stir for 20 minutes, then add 2-chloro-3-methyl-5-nitro pyridine (5 g, 28.97 mmol) in portions. After addition is completed, remove cooling bath and stir the reaction mixture at 22° C. overnight. Cool the reaction mixture with an ice bath and add a saturated aq. sodium bicarbonate solution (50 mL). Distribute the reaction mixture between ethyl acetate (350 mL) and distilled water (150 mL). Isolate the aqueous phase and extract with ethyl acetate (1×100 mL). Combine organic layers and wash with saturated aq. sodium chloride solution (2×150 mL). Dry the combined organic phases over sodium sulfate and concentrate. Subject residue to silica gel chromatography eluting with hexanes and ethyl acetate to give 4-(3-methyl-5-nitro-pyridin-2-yloxy)-piperidine-1-carboxylic acid tert-butyl ester as a white solid (6.5 g, 67% yield). MS(ES): m/z=360.3 [M+Na].

Add trifluoroacetic acid (150 mL) to a cold solution of 4-(3-methyl-5-nitro-pyridin-2-yloxy)-piperidine-1-carboxylic acid tert-butyl ester (10.12 g, 30 mmol) in dichloromethane (450 mL). Stir the reaction mixture at 22° C. for 60 min. After removal of solvent, treat the residue with 1 N sodium hydroxide (150 mL) and extract with dichloromethane and ethyl acetate. Dry the combined organic phases over sodium sulfate. Removal of solvent provides 3-methyl-5-nitro-2-(piperidin-4-yloxy)-pyridine as a yellow solid (6.9 g, 97% yield). MS(ES): m/z=238.2 [M+H].

Add 2-fluoro-benzoyl chloride (1.74 g, 11.0 mmol) dropwise to a solution of 3-methyl-5-nitro-2-(piperidin-4-yloxy)-pyridine in dichloromethane (50 mL) and triethylamine (1.21 g, 12 mmol) and stir under $N_2$ at room temperature for 2 hours. Wash the reaction mixture with distilled water (3×20 mL) followed by saturated aq. sodium chloride solution (1×20 mL). Dry the organic phase over sodium sulfate and concentrate to give (2-fluoro-phenyl)-[4-(3-methyl-5-nitro-pyridin-2-yloxy)-piperidin-1-yl]-methanone as a yellow solid.

Stir a mixture of (2-fluoro-phenyl)-[4-(3-methyl-5-nitro-pyridin-2-yloxy)-piperidin-1-yl]-methanone (3.58 g, 10 mmol) and 10% palladium on carbon (358 mg) in ethanol (100 mL) at 22° C. under hydrogen overnight. Filter to remove catalyst. Concentrate filtrate to provide a colorless oil. Subject oil to silica gel chromatography eluting with hexanes and ethyl acetate (1:1), followed by 70% ethyl acetate/hexanes to give a yellow solid (2.27 g, 50% yield). MS(ES): m/z=330.2 [M+H].

Preparation 20

4-(4-Amino-pyridin-2-yloxy)-piperidine-1-carboxylic acid tert-butyl ester

Add 100 mL of toluene to a nitrogen purged mixture of 2-chloro-4-nitro-pyridine (4.32 g, 27.2 mmol), tert-butyl 4-hydroxypiperidine carboxylate (11.0 g, 54.5 mmol), cesium carbonate (13.3 g, 40.8 mmol), palladium acetate (122 mg, 0.544 mmol) and 2-(di-tert-butylphosphino)-1,1'-binapthyl (271 mg, 0.68 mmol). Stir the resulting mixture overnight at room temperature, then partition between water and ethyl acetate. Extract the aqueous layer with additional ethyl acetate, and dry the combined organic layer over sodium sulfate and concentrate under reduced pressure. Subject residue to silica gel chromatography eluting with a gradient of 0 to 20% ethyl acetate in hexanes to afford 4-(4-nitro-pyridin-2-yloxy)-piperidine-1-carboxylic acid tert-butyl ester as a white waxy solid (5.37 g, 61%; LCMS ES+(m/z) 268 [M-tBu]$^+$).

Subject a slurry of 4-(4-nitro-pyridin-2-yloxy)-piperidine-1-carboxylic acid tert-butyl ester (3.0 g, 9.28 mmol) and 5% Pd/C (151 mg) in EtOAc (150 mL) to an atmosphere of hydrogen at 60 psi (Parr shaker) overnight at ambient temperature. Filter the reaction mixture through a pad of Celite® and concentrate under reduced pressure to provide the title compound as a white solid (2.6 g, 95% yield). LCMS ES+ (m/z) 294 [M+H].

Preparation 21

[4-(4-Amino-pyridin-2-yloxy)-piperidin-1-yl]-(2,6-difluoro-phenyl)-methanone

Add 2-Chloro-4-nitropyridine, 3 g (18.9 mmol), 4-hydroxy-piperidine-1-carboxylic acid tert-butyl ester, 7.6 g (37.8 mmol), [1,1']binaphthalenyl-2-yl-di-tert-butyl-phosphane, 188 mg (0.47 mmol), paladium acetate, 85 mg (0.38 mmol) and cesium carbonate, 9.2 g (28.4 mmol) to a 500 mL flask and purge with $N_2$ for 10 min. Then add dry toluene (500 mL) and stir at room temperature under $N_2$ atmosphere overnight. Partition the reaction between water and EtOAc (500 mL each). Separate the organic layer. Dry over MgSO$_4$, filtrate and evaporate solvents. Subject residue to silica gel chromatography eluting with a mixture of EtOAc:Hexanes in a gradient from 5 to 20% EtOAc in 10 column volumes to obtain 1.2 g (34% yield) of 4-(4-nitro-pyridin-2-yloxy)-piperidine-1-carboxylic acid tert-butyl ester title compound as a white solid (ES+(m/z)=324 [M+H].

Add 8 mL of a 4 M solution of HCl in Et$_{20}$ to 1.2 g of 4-(4-Nitro-pyridin-2-yloxy)-piperidine-1-carboxylic acid tert-butyl ester and stir the suspension for 4 hours. Evaporate the solvent and triturate the remaining solid with Et$_2$O to afford 1.1 g of 4-nitro-2-(piperidin-4-yloxy)-pyridine dihydrochloride as a pale yellow solid (100% yield) (ES+(Q/z) =224 [M+H].

Add triethylamine (2.57 mL, 18.5 mmol) to a suspension of 1.1 g (3.7 mmol) of 4-nitro-2-(piperidin-4-yloxy)-pyridine dihydrochloride in dry dichloromethane (50 mL). Then add 2,6-difluorobenzoyl chloride, 0.512 mL (4.07 mmol). Stir the mixture at room temperature overnight. Add water (50 mL) and separate organic layer. Dry with MgSO$_4$ and filter. Evaporate solvents to obtain 1.22 g (91% yield) of (2,6-difluorophenyl)-[4-(4-nitro-pyridin-2-yloxy)-piperidin-1-yl]-methanone as a yellow solid (ES+(m/z)=364 [M+H].

Add powered iron (419 mg, 7.5 mmol) to a solution of 1.1 g (3.0 mmol) of (2,6-difluoro-phenyl)-[4-(4-nitro-pyridin-2-yloxy)-piperidin-1-yl]-methanone, in glacial acetic acid (10 mL) and stir at 80° C. After 15 min, allow the mixture to reach room temperature and filter through Celite®. Wash the Celite® pad with Et₂O and EtOAc. Wash the resulting organic layer with water, a saturated aqueous NaHCO₃ solution and a saturated aqueous sodium chloride solution. Separate organic layer, dry over MgSO₄ and evaporate solvents to afford 831 mg (83% yield) of title compound as a white solid. (ES+(m/z)=334 [M+H].

Preparation 22

4-(5-Amino-pyridin-2-ylamino)-piperidine-1-carboxylic acid tert-butyl ester

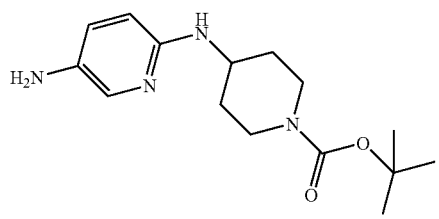

Dissolve N-Boc-4-aminopiperidine (0.9 g, 4.8 mmol) in dry ethanol and add solid sodium carbonate (0.8 g, 7.9 mmol) at 0° C., followed by 2-chloro-5-nitro-pyridine (0.6 g, 3.9 mmol). Stir the solution at room temperature overnight, then heat the solution at 9° C. for 6 hours. Stir at room temperature overnight. Evaporate the solvent under reduced pressure and partition the crude mixture between EtOH and water. Extract with EtOAc and wash the organic layer with saturated aq. sodium chloride solution. Combine organic layers and dry over MgSO₄. Filter and evaporate the solvent in order to obtain 4-(5-Nitro-pyridin-2-ylamino)-piperidine-1-carboxylic acid tert-butyl ester.

Add SnCl₂.H₂O (11.8 mmol, 2.7 g) over a solution of 4-(5-nitro-pyridin-2-ylamino)-piperidine-1-carboxylic acid tert-butyl ester (2.4 mmol, 0.8 g) in 20 mL of ethyl acetate. Stir the solution at room temperature overnight. Add aqueous NaHCO₃ solution until the solution pH is basic and extract with ethyl acetate. Filter the suspension through a pad of Celite®. Combine the organic layers and wash with saturated aq. sodium chloride, dry over sodium sulfate, filter, and concentrate under reduced pressure to give the title compound. MS(ES): m/z=293 [M+H].

Preparation 23

Methyl 1-methylcyclohexane carboxylate

Treat a solution of 1-methylcyclohexane carboxylic acid (7.11 g, 50.0 mmol) in MeOH (10 mL) and Et₂O (40 mL) dropwise with trimethylsilyldiazomethane (2.0 M/hexanes; 26 mL, 52 mmol). Stir the reaction mixture at room temperature overnight, then concentrate under reduced pressure to yield the title compound as a clear, pale yellow oil (7.811 g, 50 mmol; 100%). MS(ES): m/z=156 [M+H].

Preparation 24

3-Hydroxy-2,2-dimethyl-propionic acid benzyl ester

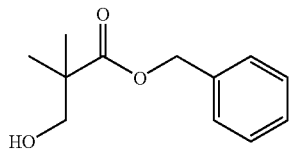

Add potassium hydroxide (486.7 mmol, 32.1 g) over a solution of 2,3-dihydroxy-2-methyl-propionic acid (423.2 mmol, 50 g) in 300 mL of DMF. Stir the solution for 1 hour at 100° C., then add benzyl bromide. Stir the solution overnight. Cool the mixture and dilute with ethyl acetate. Wash organic layer with water. Wash aqueous layer with ethyl acetate several times. Combine organic layers and dry over sodium sulfate, filter and concentrate under reduced pressure.

¹H NMR (CDCl₃, 300 MHz): δ ppm: 7.36-7.32 (m, 5H), 5.1 (s, 2H), 3.5 (s, 2H), 1.21 (s, 6H).

Preparation 25

1-Fluoromethyl-cyclopropanecarboxylic acid ethyl ester

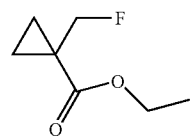

Add AgF (4.5 eq, 4.56 g) to a solution of 1-Fluoro-cyclobutanecarboxylic acid ethyl ester (1.6 g, 8 mmol) in acetonitrile (22 mL) and water (274 mL). Heat the mixture at 80° C. in a sealed tube for 20 hours while vigorously stirring. Allow the mixture to cool and filter through Celite®. Remove the solvent under reduced pressure to give the title compound as an oil (0.81 g, 61% yield) that is used without any further purification. MS(ES): m/z=147.1 [M+H].

Preparation 26

1-Trifluoromethyl-cyclonropanecarboxylic acid methyl ester

Add 2 M diazomethane solution in hexanes (14.2 mL, 28.45 mmol) to a solution of 1-trifluoromethylcyclopropane-1-carboxylic acid (3.65 g, 23.7 mmol) in methanol-hexanes (2.5 mL-22.5 mL). Concentrate under reduced pressure and distill the residue to give the title compound as a yellow oil (2.93 g, 73% yield). MS(ES): m/z=169.1 [M+H].

Preparation 27

3-Oxo-3-(1-trifluoromethyl-cyclopropyl)-propionitrile

Add 2 M LDA solution in THF (19.15 mL, 38.3 mmol) to a dry ice-acetone cooled solution of 1-trifluoromethyl-cyclopropane-1-carboxylic acid methyl ester (2.93 g, 17.4 mmol) and acetonitrile (1.43 g mL, 34.8 mmol) in THF (30 mL). Stir reaction mixture at −70° C. for 1.5 hours and then allow to warm to 22° C. for 2 hours. Concentrate, add hexanes, and filter to give a yellow solid. Wash with hexanes and treat with diethyl ether (250 mL) then 2 N HCl (150 mL). Extract aq. layer with diethyl ether (4×100 mL). Dry the combined organic phases over sodium sulfate. Removal of solvent provides 3-Oxo-3-(1-trifluoromethyl-cyclopropyl)-propionitrile (2.99 g, 97% yield). MS (ES−): m/z=176.1 [M+H].

Prepare the following compound using a procedure substantially analogous to that described above.

TABLE

| Preparation | Compound |
|---|---|
| Preparation 28 | 4,4,5,5,5-Pentafluoro-3-oxo-pentane nitrile |
| Preparation 29 | 5,5,5-Trifluoro-4-methyl-3-oxo-4-trifluoromethyl-pentanenitrile |

Preparation 30

5-(1-Methyl-cyclopropyl)-2-(6-methyl-pyridin-3-yl)-2H-pyrazol-3-ylamine

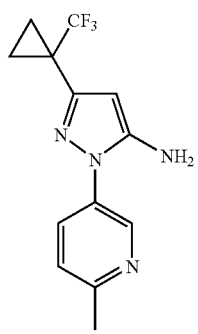

Heat a mixture of 3-Oxo-3-(1-trifluoromethyl-cyclopropyl)-propionitrile (2.66 g, 15.0 mmol), N-benzhydrylidene-N'-(6-methyl-pyridin-3-yl)-hydrazine (TL, 2002, 43, 2171-2173) (4.31 g, 15.0 mmol), and p-tolylsulfonic acid (14.29 g, 75.0 mmol) in ethanol (85 mL) at 90° C. in a sealed tube for 18 hours. After removal of the solvent, subject residue to silica gel chromatography eluting with 0-5% methanol in dichloromethane to give a brown solid (2.29 g, 54% yield). MS(ES+): m/z=283.2 [M+H].

Preparation 31

5-Pentafluoroethyl-2-p-tolyl-2H-pyrazol-3-ylamine

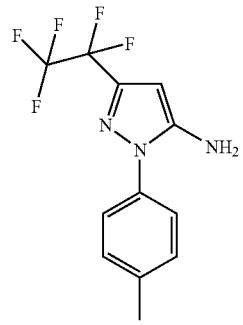

Heat a mixture of 4,4,5,5,5-pentafluoro-3-oxo-pentanenitrile (4.0 g, 21.4 mmol) and p-tolyl-hydrazine (10 g, 64.1 mmol) in ethanol (20 mL) to 95° C. in a sealed tube apparatus for 15 hours. After cooling to room temperature, remove the solvent under reduced pressure to give a yellow solid. Distribute the solid between dichloromethane (250 mL), distilled water (150 mL) and a saturated aq. sodium bicarbonate solution (50 mL). Isolate the aqueous phase and extract with dichloromethane (100 mL). Dry the combined organic phases over sodium sulfate and concentrate to give a dark gold oil. Subject oil to silica gel chromatography eluting with ethyl acetate and hexanes to give a light brown solid (3.24 g, 52% yield). MS(ES+): m/z=292.1 [M+H].

Prepare the following compound using a procedure substantially analogous to that described above.

TABLE

| Preparation | Compound | MS(ES+): m/z [M + H] |
|---|---|---|
| Preparation 32 | 2-p-Tolyl-5-(1-trifluoromethyl-cyclopropyl)-2H-pyrazol-3-ylamine | 282.3 |
| Preparation 33 | 2-p-Tolyl-5-(2,2,2-trifluoro-1-methyl-1-trifluoromethyl-ethyl)-2H-pyrazol-3-ylamine | 338.3 |

Preparation 34

[5-(1-Methyl-cyclopropyl)-2-(6-methyl-pyridin-3-yl)-2H-pyrazol-3-yl]-carbamic acid 2,2,2-trichloroethyl ester Add a solution of 2,2,2-trichloroethylchloroformate (1.80 g, 8.5 mmol) in THF (10 mL) dropwise to an ice-salt cooled solution of 5-(1-trifluoromethyl-cyclopropyl)-2-p-tolyl-2H-pyrazol-3-ylamine (2.29 g, 8.1 mmol) and pyridine (0.9 mL, 11 mmol) in THF (30 mL) at −15° C. Stir at −15° C. for 0.5 hours and then 22° C. for 1 hour, then distribute the reaction mixture between dichloromethane (50 mL) and a saturated aq. sodium bicarbonate solution (50 mL). Isolate the aqueous phase and extract twice with dichloromethane (25 mL each). Dry the combined organic phases over sodium sulfate and concentrate. Subject residue to silica gel chromatography eluting with hexanes and ethyl acetate to give a white solid (2.46 g, 66% yield). MS(ES+): m/z=457.2 [M+H].

Prepare the following compounds using a procedure substantially analogous to that described Above.

TABLE

| Preparation | Compound | MS(ES): m/z [M + H] |
|---|---|---|
| Preparation 35 | (5-Pentafluoroethyl-2-p-tolyl-2H-pyrazol-3-yl)-carbamic acid 2,2,2-trichloro-ethyl ester | 466.1 [M + H] |
| Preparation 36 | [2-p-Tolyl-5-(1-trifluoromethyl-cyclopropyl)-2H-pyrazol-3-yl]-carbamic acid 2,2,2-trichloro-ethyl ester | 458.2 [M + H] |
| Preparation 37 | [2-p-Tolyl-5-(2,2,2-trifluoro-1-methyl-1-trifluoromethyl-ethyl)-2H-pyrazol-3-yl]-carbamic acid 2,2,2-trichloro-ethyl ester | 512.2 [M + H] |

Preparation 38

5-tert-butyl-2-p-tolyl-2H-pyrazol-3-yl)-carbamic acid, 2,2,2-trichloro-ethyl ester

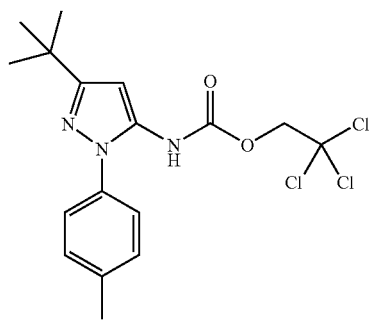

Add a saturated solution of Na$_2$CO$_3$ (2.4 L) to a solution of 5-tert-butyl-2-p-tolyl-2H-pyrazol-3-ylamine (400 g, 1.74 mol) in THF (8 L) and cool the mixture to 0° C. Then dropwise add 2,2,2-trichloroethyl chloroformate (406.77 g, 1.92 mol) and stir the mixture at 0° C. for 2 hours. Extract the reaction mixture with ethyl acetate (3×6.5 L), dry over anhydrous magnesium sulfate and concentrate. Dissolve the solid in a minimal amount of ethyl acetate and add an excess of hexanes to precipitate. Collect the solid by filtration and dry to obtain the title compound as an off white solid (586 g, 83% yield). $^1$H NMR (400 MHz, CDCl$_3$) δ 7.34 (d, 2H), 7.29 (d, 2H), 6.78 (bs, 1H), 6.41 (bs, 1H), 4.81 (s, 2H), 2.41 (s, 3H), 1.34 (s, 9H). MS(ES+): m/z=406.1[M+H].

Preparation 39

[5-(1-methyl-cyclopropyl)-2-p-tolyl-2H-pyrazol-3-yl]-carbamic acid 2,2,2-trichloroethyl ester

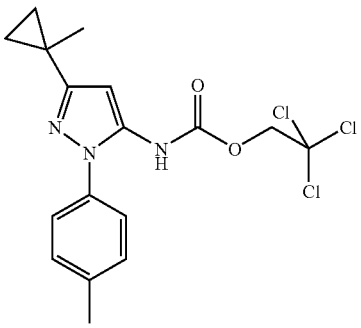

Combine lithium diisopropylamide (LDA, 2.0 M/heptanes; Aldrich; 2.2 eq, 88 mmol, 44 mL) with THF (1.5 mL/mmol; 60 mL) and cool to −78° C. Combine methyl 1-methylcyclopropane carboxylate (TCI US; 4.56 g, 40 mmol) and CH$_3$CN (4.20 mL, 80 mmol) in THF (10 mL) and add slowly with stirring. Stir the mixture at −65 to −78° C. for 1 hour, then remove the bath and warm the mixture to room temperature. Concentrate the reaction mixture to a slurry under reduced pressure. Add hexanes (150 mL) to form a precipitate from the slurry. Collect the solid by vacuum filtration and wash with hexanes (2×50 mL). Replace the catch flask with a clean one, and dissolve the solid on the frit in 50 mL 2.5 M HCl and collect in the flask. Rinse with 20 mL 2.5 M HCl followed by 200 mL Et$_2$O. Separate the layers in the filtrate and extract the acidic phase with Et$_2$O (150 mL). Combine the Et$_2$O organic phases, dry with MgSO$_4$, filter and concentrate under reduced pressure to yield 3-(1-Methylcyclopropyl)-3-oxo-propionitrile as a clear amber oil (3.58 g, 29.1 mmol, 73%). Use without purification in reaction with tolylhydrazine hydrochloride (5.23 g, 33.0 mmol) and ethanol (2 mL/mmol) at reflux for 20 hr. Cool the reaction mixture to room temperature and concentrate under reduced pressure. Dilute the residue with ethyl acetate (250 mL) and wash with water (2×60 mL), saturated aq. NaHCO$_3$ (60 mL) and saturated aq. sodium chloride (60 mL). Dry the organic phase with MgSO$_4$, filter and concentrate by rotary evaporation. Subject residue to silica gel chromatography eluting with a gradient of ethyl acetate and hexane to provide 5-(1-methyl-cyclopropyl)-2-p-tolyl-2H-pyrazol-3-ylamine (4.2238 g, 18.5 mmol, 46%). LCMS (ES+): m/z=228.2 [M+H].

Treat a cooled (0° C.) solution of the 5-(1-methyl-cyclopropyl)-2-p-tolyl-2H-pyrazol-3-ylamine (5.68 g, 25 mmol) and pyridine (2.2 mL, 27.5 mmol) in THF (3 mL/mmol) with 2,2,2-trichloroethyl chloroformate (3.7 mL, 27.5 mmol). Maintain the reaction temperature at 0° C., and after 2 hours, add small portions of chloroformate (0.3 mL) and pyridine (0.2 mL). One hour later, dilute the reaction with water (150 mL) and extract with EtOAc (3×100 mL). Wash the combined organic phases with water (100 mL), saturated aq. NaHCO$_3$ (50 mL), and saturated aq. sodium chloride (50 mL). Recrystallize the crude syrup from ethyl acetate/hexanes to provide the title compound as a white solid (8.18 g, 20.3 mmol; 81%). LCMS (ES+): m/z=402.2/404.2 [M+H].

Alternatively, add dropwise 2,2,2-trichloroethyl chloroformate (3.0 mL, 23 mmol) to a solution of 5-(1-methyl-cyclopropyl)-2-p-tolyl-2H-pyrazol-3-ylamine (4.75 g, 21 mmol)

in tetrahydrofuran (105 mL) and saturated aqueous sodium carbonate (32 mL) at 0° C. Stir at this temperature for 2 hours. Pour the mixture into water and separate phases. Extract the aqueous with ethyl acetate.

Work-Up A: Combine the organic layers and wash with aqueous sodium chloride, dry over sodium sulfate, filter, and concentrate under reduced pressure to give a yellow solid. Dissolve the solid in the minimum amount of ethyl acetate and add hexanes until cloudy while stirring. Crystallize the title compound and filter as a white solid. $^1$H NMR (DMSO): 9.89 (br s, 1H), 7.31 (d, J=8 Hz, 2H), 7.23 (d, J=8 Hz, 2H), 6.12 (s, 1H), 4.82 (s, 2H), 2.31 (s, 3H), 1.37 (s, 3H), 0.89 (q, J=4 Hz, 2H), 0.71 (q, J=4 Hz, 2H).

Work-Up B: Exchange the ethyl acetate solvent for isopropyl alcohol (91.56 moles). Stir the slurry at <0° C. for 2 hours, filter, wash with cold isopropyl alcohol (13.08 moles), and dry at 40° C. under reduced pressure overnight to afford the title compound, as a white crystalline solid.

Prepare the following compound using procedures substantially analogous to those described above.

TABLE

| Preparation | Compound | MS(ES+): m/z [M + H]) |
|---|---|---|
| Preparation 40 | [5-(1-Methyl-cyclohexyl)-2-p-tolyl-2H-pyrazol-3-yl]-carbamic acid 2,2,2-trichloro-ethyl ester | 442.2/444.2 |

Preparation 41

[5-(1-Fluoromethyl-cyclopropyl)-2-p-tolyl-2H-pyrazol-3-yl]-carbamic acid 2,2,2-trichloro-ethyl ester Prepare a solution of LDA from diisopropylamine (1.7 mL, 2.2 eq, 12.1 mmol) and n-BuLi (1.6 M in hexanes, 7.5 mL, 2.2 eq, 12.1 mmol), in THF 12 mL at −78° C. for 30 min under N$_2$. Add a solution of 1-fluoromethyl-cyclopropanecarboxylic acid ethyl ester (0.81 g, 5.5 mmol) in 7 mL of THF. Stir mixture and allow to warm from −78° C. to room temperature, and continue stirring at room temperature for 5 hours. Add 10 mL of a saturated aqueous NH$_4$Cl solution. Add AcOEt and separate the organic layer, wash with saturated aq. sodium chloride solution. Dry over Na$_2$SO$_4$ and remove solvents to give a brown oil (0.42 g, 54% yield). Dissolve oil in 10 mL of EtOH and add p-tolylhydrozine (0.47 g, 1 eq, 3 mmol). Heat the mixture in a sealed tube at 90° C. overnight. Allow mixture to cool down and remove solvent under reduced pressure to obtain a residue. Subject residue to silica gel chromatography eluting with hexane/AcOEt 15-80% to give 0.336 g of 5-(1-fluoromethyl-cyclopropyl)-2-p-tolyl-2H-pyrazol-3-ylamine as an oil. MS (ES+): m/z=246.1 [M+H].

Slowly add ClCO$_2$CH$_2$CCl$_3$ (1.00 equiv; 717.49 μmoles; 152.01 mg) to a solution of 5-(1-fluoromethyl-cyclopropyl)-2-p-tolyl-2H-pyrazol-3-ylamine (176 mg, 0.71 mmoles) and pyridine in 4 mL of THF under nitrogen at 0° C. Stir the mixture from 0° C. to room temperature for 5 hours. Filter the insoluble and remove solvent from filtrate under reduced pressure give an oil. Subject oil to chromatorgraphy (hex/AcOEt 20-80%) to give 110 mg of title compound as a yellow oil. MS (ES+): m/z=420.0 [M+H].

Preparation 42

(2-p-tolyl-5-trimethylsilanyl-2H-pyrazol-3-yl)-carbamic acid 2,2,2-trichloro-ethyl ester Place trimethylsilyl-diazomethane (2 M in THF) (25 mL, 50 mmol) in THF (50 mL). Cool the reaction to −78° C. and add lithium diisopropylamide (2 M in THF) (25 mL, 50 mmol) over 30 min. Add methyl propiolate (4.45 mL, 50 mmol) and stir at −78° C. for 2 hours. Warm to room temperature and stir for 18 hours. Add ethyl acetate, water, and 1 N HCl. Separate organic layer and extract aqueous with ethyl acetate (2×25 mL). Combine organic extracts, dry over Mg$_2$SO$_4$, filter, and concentrate under reduced pressure. Subject residue to silica gel chromatography eluting with 0-60% EtOAc:hexane to yield 3.59 g (36%) of 5-trimethylsilanyl-2H-pyrazole-3-carboxylic acid methyl ester.

Place 5-trimethylsilanyl-2H-pyrazole-3-carboxylic acid methyl ester (1.60 g, 8.07 mmol) and 4-methylphenyl-1-boronic acid (1.64 g, 12.1 mmol) in CH$_2$Cl$_2$ (30 mL). Add 4 Å molecular sieves (1.50 g) followed by copper (II) acetate (1.61 g, 8.88 mmol). Then add triethylamine (8 mL) and stir at room temperature for 2.5 days. Filter reaction through a pad of Celite® and wash with CH$_2$Cl$_2$. Collect the filtrate and add saturated aqueous ammonium chloride. Separate organic layer and extract aqueous layer with CH$_2$Cl$_2$ (2×20 mL). Combine organic extracts, dry over Mg$_2$SO$_4$, filter, and concentrate under reduced pressure. Subject residue to silica gel chromatography eluting with 0-30% EtOAc:hexane to yield 655 mg (29%) of 2-p-tolyl-5-trimethylsilanyl-2H-pyrazole-3-carboxylic acid methyl ester. MS(ES+): m/z=289.3 [M+H]).

Place 2-p-tolyl-5-trimethylsilanyl-2H-pyrazole-3-carboxylic acid methyl ester (665 mg, 2.30 mmol) in methanol (25 mL). Add 1 N NaOH (10 mL, 10 mmol) and heat to 50° C. for 4 hours. Cool to room temperature and concentrate under reduced pressure. Add saturated aq. sodium bicarbonate solution and CH$_2$Cl$_2$. Separate organic layer and extract aqueous layer with CH$_2$Cl$_2$ (2×25 mL). Combine organic extracts, dry over Mg$_2$SO$_4$, filter, and concentrate under reduced pressure to yield 620 mg (98%) of 2-p-tolyl-5-trimethylsilanyl-2H-pyrazole-3-carboxylic acid. MS(ES+): m/z=275.3 [M+H].

Place 2-p-tolyl-5-trimethylsilanyl-2H-pyrazole-3-carboxylic acid (620 mg, 2.26 mmol) in tert-butanol (5 mL) and toluene (5 mL). Add triethylamine (0.378 mL, 2.71 mmol), followed by diphenyl phosphoryl azide (0.586 mL, 2.71 mmol) and heat to 60° C. for 1 hour. Then heat to 100° C. for 19 hours. Concentrate reaction under reduced pressure. Subject residue to silica gel chromatography eluting with 0-30% EtOAc:hexane to yield 504 mg (65%) of (2-p-tolyl-5-trimethylsilanyl-2H-pyrazol-3-yl)-carbamic acid tert-butyl ester. MS(ES+): m/z=346.4 [M+H].

Place (2-p-tolyl-5-trimethylsilanyl-2H-pyrazol-3-yl)-carbamic acid tert-butyl ester (504 mg, 1.46 mmol) in THF (10 mL). Add 4 M HCl in dioxane (4 mL, 16 mmol) and heat to 60° C. for 3 hours. Cool the reaction to room temperature and load onto a Varian™ SCX column. Wash the column with MeOH and then flush off the product with 2 M NH$_3$ in MeOH. Collect filtrate and concentrate under reduced pressure to yield 175 mg (49%) of 2-p-tolyl-5-trimethylsilanyl-2H-pyrazol-3-ylamine.

Place 2-p-tolyl-5-trimethylsilanyl-2H-pyrazol-3-ylamine (170 mg, 0.693 mmol) in ethyl acetate (10 mL). Add potassium carbonate (191 mg, 1.38 mmol) and water (2 mL). Stir the reaction and add trichloroethyl chloroformate (0.114 mL, 0.831 mmol). Stir at room temperature for 18 hours. Add water and ethyl acetate. Separate organic layer and wash with saturated aq. sodium chloride. Collect organic layer, dry over Mg$_2$SO$_4$, filter, and concentrate under reduced pressure. Subject residue to silica gel chromatography eluting with 0-30% EtOAc:hexane to yield 280 mg (96%) of the title compound. MS(ES+): m/z=420.2 [M+H].

Preparation 43

[5-(2-Fluoro-1-fluoromethyl-1-methyl-ethyl)-2-tolyl-2H-pyrazol-3-yl]-carbamic acid 2,2,2-trichloro-ethyl ester Add H$_2$SO$_4$ (4.5 g) to a suspension of 3-hydroxy-2-hydroxymethyl-2-methyl-propionic acid (100 g) in MeOH (1 L, HPLC grade solvent) and stir at room temperature through the week-end (ca. 70 h). Remove the solvent and partition the residue between EtOAc (1 L) and H$_2$O (100 mL). Re-extract the aqueous layer with EtOAc, and dry the combined organic layers over MgSO$_4$. Filter and concentrate under reduced pressure to yield 3-hydroxy-2-hydroxymethyl-2-methyl-propionic acid methyl ester. $^1$H NMR (CDCl$_3$, 300 MHz): δ ppm 3.9 (d, 2H, J=11.1. Hz), 3.76 (s, 3H), 3.71 (d, 2H, J=1-1. Hz), 2.8 (bs, 2H), 1.1 (s, 3H).

Add Tf$_2$O (80 mL) dropwise to a cold (−78° C.) solution of 3-hydroxy-2-hydroxymethyl-2-methyl-propionic acid methyl ester (32.5 g) in CH$_2$Cl$_2$ (400 mL) and 2,6-lutidine (80 mL). The reaction is allowed to reach room temperature and stir until only product spot detected by TLC analysis (ca. 2 h). Dilute with CH$_2$Cl$_2$ (400 mL) and wash with HCl (3% aqueous solution). Dry the organic layer over MgSO$_4$, filter and concentrate. Subject residue to silica gel chromatography eluting with hexanes/ethyl acetate 5%, to give 2-methyl-2,3-bis-trifluoromethanesulfonyloxy-propionic acid methyl ester as a colorless oil.

$^1$H NMR (CDCl$_3$, 300 MHz): 6 ppm 4.7 (d, 2H, J=10.3 Hz), 4.5 (d, 2H, J=10.3 Hz), 3.8 (s, 3H), 1.4 (s, 3H).

Add TBAF 1 M (132 mmol, 132 mL) over a solution of 2-methyl-2,3-bis-trifluoromethanesulfonyloxy-propionic acid methyl ester (65.9 mmol, 26.3 g) in 500 mL of anhydrous THF cooled down to 0° C. Stir overnight. Concentrate under reduced pressure and add CH$_2$Cl$_2$. Wash organic layer with saturated aq. sodium chloride. Combine organic layers and dry over sodium sulfate, filter, and concentrate under reduced pressure to give 3-fluoro-2-fluoromethyl-2-methyl-propionic acid methyl ester $^1$H NMR (CDCl$_3$, 300 MHz): δ ppm: 4.7-4.4 (m, 4H), 3.5 (s, 3H), 0.98 (t, 3H, J=1.7 Hz).

Add LDA 2.0 M (62.0 mmol, 31 mL) followed by anhydrous acetonitrile (56.4 mmol, 2.9 mL) over a solution of 3-fluoro-2-fluoromethyl-2-methyl-propionic acid methyl ester (28.2 mmol, 4.3 g) in 100 mL of anhydrous THF cooled down to −78° C. Stir for two hours at −78° C. and allow the solution to warm to room temperature overnight. Concentrate under reduced pressure and add CH$_2$Cl$_2$. Wash organic layer with saturated aq. sodium chloride and aq. 10% HCl. Combine organic layers and dry over sodium sulfate, filter, and concentrate under reduced pressure to give a residue. Strip-tolylhydrazine hydrochloride (15.5 mmol, 2.5 g) and residue obtained (15.5 mmol, 2.5 g) in 31 mL of ethanol at 90° C. overnight. Concentrate, and dissolve the residue in water. Add 10% sodium hydroxide solution, and extract in ethyl acetate. Combine organic layers and dry over sodium sulfate, filter, and concentrate under reduced pressure to give a 5-(2-fluoro-1-fluoromethyl-1-methyl-ethyl)-2-p-tolyl-2H-pyrazol-3ylamine. Subject residue to silica gel chromatography eluting with hexanes/ethyl acetate (from 15% to 50%). MS(ES+): m/z=266 [M+H].

Add 2,2,2-trichloroethyl chloroformate (8.1 mmol, 1.1 mL) and aq. sodium carbonate solution (4.8 mL) over a solution of 5-(2-fluoro-1-fluoromethyl-1-methyl-ethyl)-2-p-tolyl-2H-pyrazol-3-ylamine (7.3 mmol, 1.9 g) in 37 mL of THF. Stir for 24 hours. Pour the solution over water and extract in ethyl acetate. Combine organic layers and wash with saturated aq. sodium chloride solution. Dry over sodium sulfate, filter, and concentrate under reduced pressure to give the title compound. MS(ES+): m/z=440 [M+H].

Prepare the following compound using procedures substantially analogous to those described above.

TABLE

| Preparation | Compound | MS(ES+): m/z [M + H]) |
| --- | --- | --- |
| Preparation 44 | [5-(2-Fluoro-1,1-dimethyl-ethyl)-2-p-tolyl-2H-pyrazol-3-yl]-carbamic acid 2,2,2-trichloro-ethyl ester | 424 |

Preparation 45

4-(5-{3-[5-(1-Methyl-cyclopropyl)-2-p-tolyl-2H-pyrazol-3-yl]-ureido}-pyridin-2-yl)-piperazine-1-carboxylic acid tert-butyl ester

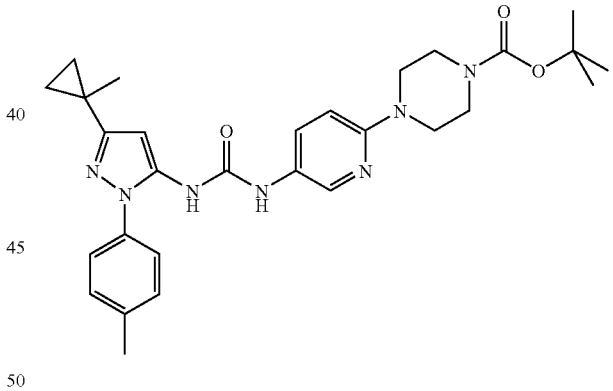

Heat a solution of 4-(5-amino-pyridin-2-yl)-piperazine-1-carboxylic acid tert-butyl ester (Preparation 4, 1.05 equiv, 0.5845 g), [5-(1-methyl-cyclopropyl)-2-p-tolyl-2H-pyrazol-3-yl]-carbamic acid 2,2,2-trichloroethyl ester (Preparation 39, 1.0 equiv, 0.8054 g) and diisopropylethylamine (2 equiv, 0.7 mL) in DMSO (0.25 M, 8 mL) to 60° C. for 6 hours. Cool the resulting mixture to ambient temperature, and add water (20 mL). Extract with EtOAc (2×25 mL), then wash the combined organic phases with water (10 mL) and saturated aq. sodium chloride solution (10 mL). Dry over MgSO$_4$, then subject residue to silica gel chromatography eluting with a gradient 2 M ammonia-methanol in dichloromethane. LCMS (ES+): m/z=532.3 [M+H].

Prepare the following compounds using a procedure substantially analogous to that described above.

TABLE

| Preparation | Compound | MS(ES+): m/z [M + H]) |
|---|---|---|
| Preparation 46 | 4-(3-Methyl-5-{3-[5-(1-methyl-cyclopropyl)-2-p-tolyl-2H-pyrazol-3-yl]-ureido}-pyridin-2-yl)-piperazine-1-carboxylic acid tert-butyl ester | 546 |
| Preparation 47 | 4-(6-Methyl-5-{3-[5-(1-methyl-cyclopropyl)-2-p-tolyl-2H-pyrazol-3-yl]-ureido}-pyridin-2-yl)-piperazine-1-carboxylic acid tert-butyl ester | 546 |
| Preparation 48 | 4-(3-Methyl-5-{3-[5-(1-methyl-cyclohexyl)-2-p-tolyl-2H-pyrazol-3-yl]-ureido}-pyridin-2-yl)-piperazine-1-carboxylic acid tert-butyl ester | 588.3 |

Preparation 49

4-{5-[3-(5-tert-Butyl-2-p-tolyl-2H-pyrazol-3-yl)-ureido]-6-methyl-pyridin-2-yl}-piperazine-1-carboxylic acid tert-butyl ester Heat a solution of 4-(5-amino-6-methyl-pyridin-2-yl)-piperazine-1-carboxylic acid tert-butyl ester (Preparation 3, 41.20 g, 140.9 mmol), (5-tert-butyl-2-p-tolyl-2H-pyrazol-3-yl)-carbamic acid, 2,2,2-trichloro-ethyl ester (Preparation 38, 57.03 g, 140.9 mmol), and DIEA (36.8 mL, 211.4 mmol) in DMSO (500 mL) at 60-65° C. for 2.5 hours. Add additional DMSO (100 mL) during the last 30 min to the thick slurry. Cool the slurry to room temperature and allow to stand overnight. Add diethyl ether (600 mL) and stir the slurry for 1 hour at room temperature. Filter and wash with diethyl ether (5×300 mL) then air-dry to afford a white solid (68.70 g, 89% yield uncorrected for DMSO—contains ca. 85 mol % of DMSO. LCMS(ES+): m/z=548 [M+H].

Preparation 50

1-[5-(1-Methyl-cyclopropyl)-2-p-tolyl-2H-pyrazol-3-yl]-3-(2-methyl-6-piperazin-1-yl-pyridin-3-yl)-urea

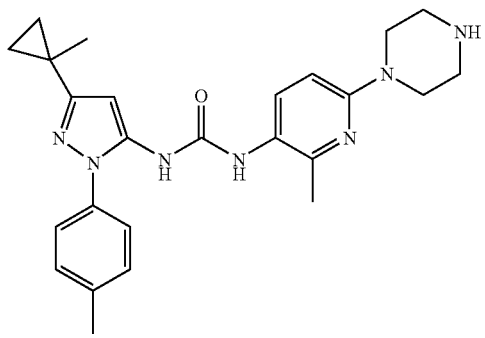

Bubble gaseous hydrochloric acid through a solution of 4-(6-methyl-5-{3-[5-(1-methyl-cyclopropyl)-2-p-tolyl-2H-pyrazol-3-yl]-ureido}-pyridin-2-yl)-piperazine-1-carboxylic acid tert-butyl ester (assume 2.74 mmol) in 1:1 ethyl acetate:dichloromethane (200 mL) for 3 min to ensure saturation. Allow the mixture to stand for 30 min then concentrate under reduced pressure to a white solid. Dissolve the solid in MeOH and load onto a 20 g Varian SCX column, rinsing with additional MeOH. Elute the free base with 1:1 2 M ammonia in MeOH:dichloromethane. Concentrate the solution under reduced pressure to give a white solid (1.21 g, 99% over 2 steps). LCMS(ES+): m/z=446 [M+H].

Prepare the following compound using procedures substantially analogous to those described above.

TABLE

| Preparation | Compound | MS(ES+): m/z [M + H]) |
|---|---|---|
| Preparation 51 | 1[5-(1-Methyl-cyclopropyl)-2-p-tolyl-2H-pyrazol-3-yl]-3-(5-methyl-6-piperazin-1-yl-pyridin-3-yl)-urea | 446 |

Preparation 52

1-(5-tert-butyl-2-p-tolyl-2H-pyrazol-3-yl)-3-(6-piperazin-1-yl-pyridin-3-yl)-urea Place 4-(5-amino-pyridin-2-yl)-piperazine-1-carboxylic acid tert-butyl ester (200 mg, 0.718 mmol), diisopropylethylamine (0.125 mL, 0.718 mmol), and (5-tert-butyl-2-p-tolyl-2H-pyrazol-3-yl)-carbamic acid, 2,2,2-trichloro-ethyl ester (Preparation 38, 291 mg, 0.718 mmol) in DMSO (5 mL) and heat to 75° C. for 17 hours. Cool to room temperature and add EtOAc and water. Separate organic layer and wash with saturated aq. sodium chloride (2×20 mL). Collect organic layer, dry over Mg$_2$SO$_4$, filter, and concentrate under reduced pressure. Subject residue to silica gel chromatography eluting with 0-70% EtOAc:hexane to yield 328 mg (85%) of 4-{5-[3-(5-tert-butyl-2-p-tolyl-2H-pyrazol-3-yl)-ureido]-pyridin-2-yl}-piperazine-1-carboxylic acid tert-butyl ester. MS(ES+): m/z=534.4 [M+H]).

Place 4-{5-[3-(5-tert-butyl-2-p-tolyl-2H-pyrazol-3-yl)-ureido]-pyridin-2-yl}-piperazine-1-carboxylic acid tert-butyl ester (565 mg, 1.06 mmol) in THF (10 mL). Add 4 M HCl in dioxane (2.65 mL, 10.6 mmol) and heat to 60° C. for 3 hours. Cool the reaction to room temperature and load onto a Varian™ SCX column. Wash the column with MeOH and then flush off the product with 2 M NH$_3$ in MeOH.

Collect filtrate and concentrate under reduced pressure to yield 411 mg (89%) of the title compound. MS(ES+): m/z=434.2 [M+H])

Prepare the following compounds using procedures substantially analogous to those described above.

TABLE

| Preparation | Compound | MS(ES+): m/z [M + H]) |
|---|---|---|
| Preparation 53 | 1-(5-tert-butyl-2-p-tolyl-2H-pyrazol-3-yl)-3-(5-methyl-6-piperazin-1-yl-pyridin-3-yl)-urea | 448.5 |
| Preparation 54 | 1-(5-tert-butyl-2-p-tolyl-2H-pyrazol-3-yl)-3-(5-chloro-6-piperazin-1-yl-pyridin-3-yl)-urea hydrochloride (no purification) | 468.4 |
| Preparation 55 | 1-(6-piperazin-1-yl-pyridin-3-yl)-3-(2-p-tolyl-5-trimethylsilanyl-2H-pyrazol-3-yl)-urea | 450.4 |

Preparation 56

1-(5-tert-Butyl-2-p-tolyl-2H-pyrazol-3-yl)-3-(2-methyl-6-piperazin-1-yl-pyridin-3-yl)-urea Treat a 22° C. solution of 4-{5-[3-(5-tert-butyl-2-p-tolyl-2H-pyrazol-3-yl)-ureido]-6-methyl-pyridin-2-yl}-piperazine-1-carboxylic acid tert-butyl ester (Preparation 49; 63.20 g, 115.4 mmol) in MeOH (600 mL) with HCl (4 N solution in dioxane, 300 mL, 1200 mmol). Stir the mixture for 4 hours then concentrate under reduced pressure (room temperature, ca. 10 torr, 3 days) to afford 1-(5-tert-butyl-2-p-tolyl-2H-pyrazol-3-yl)-3-(2-methyl-6-piperazin-1-yl-pyridin-3-yl)-urea dihydrochloride as an off-white powder (62.2 g—contains ca. 45 mol % of dioxane. LCMS(ES+): m/z=448 [M+H].

Load a solution of 1-(5-tert-butyl-2-p-tolyl-2H-pyrazol-3-yl)-3-(2-methyl-6-piperazin-1-yl-pyridin-3-yl)-urea dihydrochloride (10 g, 19.2 mmol) in MeOH onto a 70 g Varian SCX column, rinsing with MeOH (ca. 300 mL). Elute the free base with 1:1 2 M ammonia in MeOH:dichloromethane (150 mL). Concentrate under reduced pressure to give a white solid (6.24 g). LCMS(ES+): m/z=448 [M+H].

Prepare the following compounds using procedures substantially analogous to those described above.

TABLE

| Preparation | Compound | MS(ES+): m/z [M + H]) |
|---|---|---|
| Preparation 57 | 1-[5-(1-Methyl-cyclopropyl)-2-p-tolyl-2H-pyrazol-3-yl]-3-(6-piperazin-1-yl-pyridin-3-yl)-urea | 432.2 |
| Preparation 58 | 1-[5-(1-Methyl-cyclohexyl)-2-p-tolyl-2H-pyrazol-3-yl]-3-(5-methyl-6-piperazin-1-yl-pyridin-3-yl)-urea | 488.5 |

Preparation 59

1-(5-tert-Butyl-2-p-tolyl-2H-pyrazol-3-yl)-3-[2-methyl-6-(piperidin-4-yloxy)-pyridin-3-yl]-urea

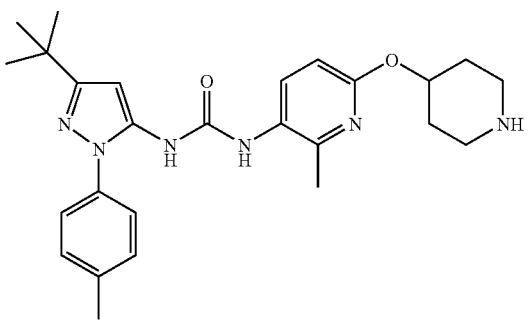

Bubble nitrogen gas through a solution of 1-5-tert-butyl-2-p-tolyl-2H-pyrazol-3-yl)-carbamic acid, 2,2,2-trichloroethyl ester (Preparation 38, 608 mg, 1.5 mmol) and 4-(5-amino-6-methyl-pyridin-2-yloxy)-piperidine-1-carboxylic acid tert-butyl ester (453 mg, 1.5 mmol) in DMSO (3 mL) for 5 min. Next add N,N-diisopropylethylamine (500 □L, 3.0 mmol). Stir at 60° C. overnight, then distribute the reaction mixture between ethyl acetate (25 mL) and saturated aq. sodium bicarbonate solution (50 mL). Isolate the aqueous phase and extract twice with ethyl acetate (25 mL each). Dry the combined organic phases over sodium sulfate and concentrate. Subject residue to silica gel chromatography eluting with hexanes and ethyl acetate to give 4-{5-[3-(5-tert-butyl-2-p-tolyl-2H-pyrazol-3-yl)-ureido]-6-methyl-pyridin-2-yloxy}-piperidine-1-carboxylic acid tert-butyl ester as a brown solid (746 mg, 88% yield). MS(ES+): m/z=563.3 [M+H].

Add trifluoroacetic acid (10 mL) to a cold solution of 4-{5-[3-(5-tert-butyl-2-p-tolyl-2H-pyrazol-3-yl)-ureido]-6-methyl-pyridin-2-yloxy}-piperidine-1-carboxylic acid tert-butyl ester (746 mg, 1.33 mmol) in dichloromethane (20 mL). Stir the reaction mixture at 22° C. for 25 min. After removal of solvent, treat the residue with 1 N sodium hydroxide (20 mL) and extract three times with dichloromethane (20 mL each). Dry the combined organic phases over sodium sulfate. Removal of solvent provides a white solid (605 mg, 98% yield). MS(ES+): m/z=463.2 [M+H].

Prepare the following compounds using procedures substantially analogous to those described above.

TABLE

| Preparation | Compound | MS(ES+): m/z [M + H]) |
|---|---|---|
| Preparation 60 | 1-(5-tert-Butyl-2-methyl-2H-pyrazol-3-yl)-3-[6-(piperidin-4-yloxy)-pyridin-3-yl]-urea | 373.3 |
| Preparation 61 | 1-[5-tert-Butyl-2-(6-methyl-pyridin-3-yl)-2H-pyrazol-3-yl]-3-(2-methyl-6-piperazin-1-yl-pyridin-3-yl)-urea | 449.2 |
| Preparation 62 | 1-(2-Methyl-6-piperazin-1-yl-pyridin-3-yl)-3-[2-(6-methyl-pyridin-3-yl)-5-(1-trifluoromethyl-cyclopropyl)-2H-pyrazol-3-yl]-urea | 501.3 |
| Preparation 63 | 1-(5-tert-Butyl-2-p-tolyl-2H-pyrazol-3-yl)-3-[6-(piperidin-4-yloxy)-pyridin-3-yl]-urea | 449.2 |
| Preparation 64 | 1-(5-tert-Butyl-2-p-tolyl-2H-pyrazol-3-yl)-3-[5-methyl-6-(piperidin-4-yloxy)-pyridin-3-yl]-urea | 463.2 |
| Preparation 65 | 1-(5-tert-Butyl-2-p-tolyl-2H-pyrazol-3-yl)-3-[5-chloro-6-(piperidin-4-yloxy)-pyridin-3-yl]-urea | 483.3 |
| Preparation 66 | 1-(2-Methyl-6-piperazin-1-yl-pyridin-3-yl)-3-(5-pentafluoroethyl-2-p-tolyl-2H-pyrazol-3-yl)-urea | 510.4 |
| Preparation 67 | 1-(2-Methyl-6-piperazin-1-yl-pyridin-3-yl)-3-[2-p-tolyl-5-(1-trifluoromethyl-cyclopropyl)-2H-pyrazol-3-yl]-urea | 510.4 |

Preparation 68

1-[5-(2-Fluoro-1-fluoromethyl-1-meth-ethyl)-2-p-tolyl-2H-pyrazol-3-yl]-3-(2-methyl-6-piperazin-1-yl-pyridin-3-yl)-urea hydrochloride Add [5-(2-fluoro-1-fluoromethyl-1-methyl-ethyl)-2-p-tolyl-2H-pyrazol-3-yl]-carbamic acid 2,2,2-trichloro-ethyl ester (2.7 mmol, 1.2 g) and DIEA (2.9 mmol, 0.5 mL) over a solution of 4-(5-amino-6-methyl-pyridin-2-yl)-piperazine-1-carboxylic acid tert-butyl ester (2.9 mmol, 0.9 g) in 4 mL of DMSO and stir at 85° C. overnight. Cool down, add water and extract with $CH_2Cl_2$. Combine the organic layers and wash with saturated aq. sodium chloride solution. Dry over sodium sulfate, filter, and concentrate under reduced pressure to give 4-(5-{3-[5-(2-fluoro-1-fluoromethyl-1-methyl-ethyl)-2-p-tolyl-2H-pyrazol-3-yl]-ureido}-6-methyl-pyridin-2-yl)-piperazine-1-carboxylic acid tert-butyl ester. Subject residue to silica gel chromatography eluting with hexanes/ethyl acetate in gradient (from 10 to 50%). MS(ES+): m/z=584 [M+H]).

Stir 4-(5-{3-[5-(2-fluoro-1-fluoromethyl-1-methyl-ethyl)-2-p-tolyl-2H-pyrazol-3-yl]-ureido}-6-methyl-pyridin-2-yl)-piperazine-1-carboxylic acid tert-butyl ester (1.5 mmol, 0.9 g) dissolve in 5 mL of $CH_2Cl_2$ and hydrogen chloride 4.0 M in dioxane (7.35 mmol, 1.8 mL) at room temperature overnight. Concentrate, then triturate the white solid formed with diethyl ether. MS(ES+): m/z=484 [M+H])

Prepare the following compound using procedures substantially analogous to those described above.

TABLE

| Preparation | Compound | MS(ES+): m/z [M + H] |
|---|---|---|
| Preparation 69 | 1-[5-(2-Fluoro-1,1-dimethyl-ethyl)-2-p-tolyl-2H-pyrazol-3-yl]-3-(2-methyl-6-piperazin-1-yl-pyridin-3-yl)-urea hydrochloride | 466 |

Preparation 70

1-(5-tert-Butyl-2-p-tolyl-2H-pyrazol-3-yl)-3-[6-(piperidin-4-ylamino)-pyridin-3-yl]-urea Add (5-tert-butyl-2-p-tolyl-2H-pyrazol-3-yl)-carbamic acid, 2,2,2-trichloro-ethyl ester (Preparation 38, 2.0 mmol, 0.8 g) over a solution of 4-(5-amino-pyridin-2-ylamino)-piperidine-1-carboxylic acid tert-butyl ester (2.0 mmol, 0.6 g) and potassium carbonate (2.20 mmol, 0.3 g) in acetonitrile (25 mL). Stir the solution for 12 hours at room temperature. Add water and extract with $CH_2Cl_2$. Combine the organic layers and wash with saturated aq. sodium chloride, dry over sodium sulfate, filter, and concentrate under reduced pressure to give a residue. Subject residue to silica gel chromatography eluting with $CH_2Cl_2$: MeOH in gradient (from 0.5 to 20%) to yield 4-{5-[3-(5-tert-butyl-2-p-tolyl-2H-pyrazol-3-yl)-ureido]-pyridin-2-ylamino}-piperidine-1-carboxylic acid tert-butyl ester. MS(ES+): m/z=548 [M+H])

Treat a 22° C. solution of 4-{5-[3-(5-tert-butyl-2-p-tolyl-2H-pyrazol-3-yl)-ureido]-pyridin-2-ylamino}-piperidine-1-carboxylic acid tert-butyl ester (1.1 mmol, 0.6 g) in $Et_2O$ (5 mL) with HCl (2.0 M solution in diethyl ether, 5 mL, 10 mmol). Stir the solution overnight at room temperature. Concentrate under reduced pressure to give a residue, then subject residue to SCX cartridge eluting with ammonia 2.0 N in methanol. Obtain the title compound as the free base. MS(ES): m/z=488 [M+H].

Preparation 71

1-(5-tert-Butyl-2-p-tolyl-2H-pyrazol-3-yl)-3-[2-(piperidin-4-yloxy)-pyridin-4-yl]-urea

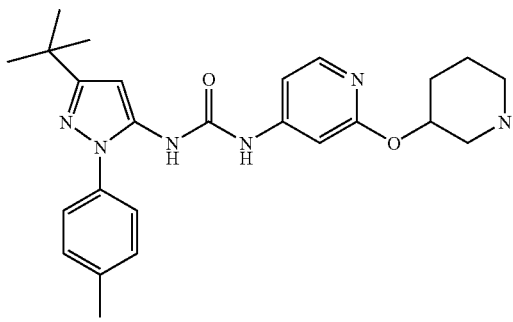

Heat a solution of 4-(4-amino-pyridin-2-yloxy)-piperidine-1-carboxylic acid tert-butyl ester (Preparation 20, 1 g, 3.41 mmol), (5-tert-butyl-2-p-tolyl-2H-pyrazol-3-yl)-carbamic acid 2,2,2-trichloro-ethyl ester (Preparation 38, 1.38 g, 3.41 mmol), and diisopropylethylamine (1.2 mL, 6.82 mmol) in DMSO (15 mL) at 60° C. for 5 d. Cool the resulting mixture to room temperature and partition between water and ethyl acetate using saturated aq. sodium chloride solution to aid phase separation. Extract the aqueous layer with ethyl acetate, wash the combined organic layers twice with water, dry over sodium sulfate and concentrate under reduced pressure. Subject residue to silica gel chromatography eluting with a gradient of ethyl acetate in dichloromethane to give 877 mg (43% yield) of 4-{4-[3-(5-tert-butyl-2-p-tolyl-2H-pyrazol-3-yl)-ureido]-pyridin-2-yloxy}-piperidine-1-carboxylic acid tert-butyl ester. LCMS ES+(m/z) 549 [M+H].

Treat a solution of 4-{4-[3-(5-tert-butyl-2-p-tolyl-2H-pyrazol-3-yl)-ureido]-pyridin-2-yloxy}-piperidine-1-carboxylic acid tert-butyl ester (877 mg, 1.6 mmol) in 1:1 EtOAc:DCM (100 mL) with a bubbling stream of HCl (g) for 3 min. Allow the resulting mixture to stand for 30 min, then concentrate under reduced pressure. Dissolve the residue in MeOH and load onto a 20 g Varian SCX column, rinsing well with MeOH. Elute the free base with 1:1 DCM:2 M ammonia in MeOH. Concentrate the solution under reduced pressure to give the title compound in quantitative yield. LCMS ES+(m/z) 449 [M+H].

Prepare the following compound using a procedure substantially analogous to that described above.

TABLE

| Preparation | Compound | MS(ES+): m/z [M + H] |
|---|---|---|
| Preparation 72 | 1-[5-(1-Methyl-cyclopropyl)-2-p-tolyl-2H-pyrazol-3-yl]-3-[2-(piperidin-4-yloxy)-pyridin-4-yl]-urea | 447 |

EXAMPLE 1

1-{6-[4-(2,2-Dimethyl-pentanoyl)-piperazin-1-yl]-piperidin-3-yl}-3-[5-(1-methyl-cyclopropyl)-2-p-tolyl-2H-pyrazol-3-yl]-urea

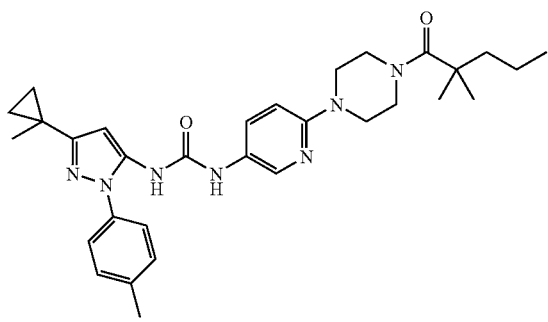

Treat a solution or slurry of the 1-[5-(1-methyl-cyclopropyl)-2-p-tolyl-2H-pyrazol-3-yl]-3-(6-piperazin-1-yl-pyridin-3-yl)-urea (Preparation 5, 1 equiv., 0.1510 g), 2,2-dimethyl pentanoic acid (1.15 equiv., 0.0521 g) and catalytic DMAP (ca. 0.1 equiv., 0.049 g) in dichloromethane (ca. 0.1 M, 5 mL) with N-(3-dimethylaminopropyl)-N'-ethylcarbodiimide hydrochloride (EDC 1.15 equiv., 0.0767 g). Agitate the resulting mixture at ambient temperature for 48 hours then wash with saturated aq. sodium bicarbonate solution. Dry the organic layer over sodium sulfate and concentrate under reduced pressure. Purification A: Purify on silica gel using a gradient 2 M ammonia-methanol in dichloromethane, a gradient of ethyl acetate in dichloromethane or hexanes. Purification B: Purify by reverse phase on an Xterra 30×75 mm 5 micron MS C18 column using a gradient of aqueous 10 mM ammonium bicarbonate in acetonitrile affords the title compound. LCMS(ES+): m/z=544. [M+H].

Prepare the following compounds using procedures substantially analogous to those described above.

TABLE

| EXAMPLE | Compound | MS(ES+): (m/z) [M + H] |
|---|---|---|
| 2 | 1-{6-[4-(1-Methyl-cyclohexanecarbonyl)-piperazin-1-yl]-pyridin-3-yl}-3-[5-(1-methyl-cyclopropyl)-2-p-tolyl-2H-pyrazol-3-yl]-urea | 556 |
| 3 | 1-{6-[4-(2,6-Difluoro-benzoyl)-piperazin-1-yl]-pyridin-3-yl}-3-[5-(1-methyl-cyclopropyl)-2-p-tolyl-2H-pyrazol-3-yl]-urea | 572 |

EXAMPLE 4

1-(5-tert-Butyl-2-p-tolyl-2H-pyrazol-3-yl)-3-{6-[4-(2,2-dimethyl-propionyl)-piperazin-1-yl]-2-methyl-pyridin-3-yl}-urea methanesulfonate

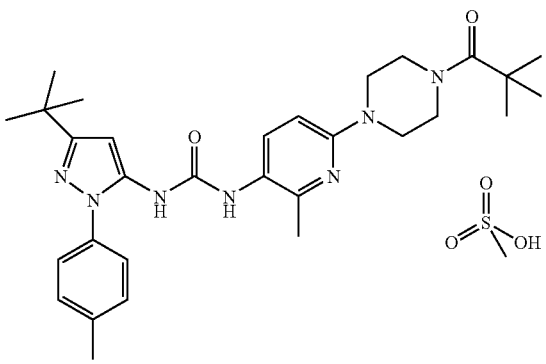

Treat a mixture of 1-(5-tert-butyl-2-p-tolyl-2H-pyrazol-3-yl)-3-(2-methyl-6-piperazin-1-yl-pyridin-3-yl)-urea (Preparation 56, 157 mg, 0.35 mmol), trimethylacetic acid (54 mg, 0.53 mmol) and catalytic DMAP (4 mg) in dichloromethane (3.5 ml) with N-(3-dimethylaminopropyl)-N'-ethylcarbodiimide hydrochloride (EDCI; 101 mg, 0.53 mmol). Stir the resulting mixture at room temperature overnight then wash with saturated aq. sodium bicarbonate solution. Dry the organic layer over sodium sulfate and concentrate under reduced pressure. Subject residue to silica gel chromatography eluting with a gradient 2 M ammonia-methanol in dichloromethane to afford the title compound as the free base. LCMS(ES+): m/z=532 [M+H].

Treat a solution or slurry of the free amine in dichloromethane (5 mL) with 2 M methane sulfonic acid in dichloromethane (1 equiv.; 0.155 mL). Stir the resulting mixture, concentrate under a stream of nitrogen and dry under reduced pressure to afford the salt.

Prepare the following compounds using procedures substantially analogous to those described above.

| EXAMPLE | Compound | LCMS (ES+): m/z [M + H] |
|---|---|---|
| 5 | 1-(5-tert-Butyl-2-p-tolyl-2H-pyrazol-3-yl)-3-{6-[4-(2,6-difluoro-benzoyl)-piperazin-1-yl]-2-methyl-pyridin-3-yl}-urea methanesulfonate | 588 |
| 6 | 1-(5-tert-Butyl-2-p-tolyl-2H-pyrazol-3-yl)-3-{2-methyl-6-[4-(1-methyl-cyclopropanecarbonyl)-piperazin-1-yl]-pyridin-3-yl}-urea methanesulfonate | 530 |
| 7 | 1-(5-tert-Butyl-2-p-tolyl-2H-pyrazol-3-yl)-3-{6-[4-(2,5-difluoro-benzoyl)-piperazin-1-yl]-2-methyl-pyridin-3-yl}-urea methanesulfonate | 588 |
| 8 | 1-(5-tert-Butyl-2-p-tolyl-2H-pyrazol-3-yl)-3-{6-[4-(2,4-difluoro-benzoyl)-piperazin-1-yl]-2-methyl-pyridin-3-yl}-urea methanesulfonate | 588 |
| 9 | 1-(5-tert-Butyl-2-p-tolyl-2H-pyrazol-3-yl)-3-{6-[4-(2,3-difluoro-benzoyl)-piperazin-1-yl]-2-methyl-pyridin-3-yl}-urea methanesulfonate | 588 |
| 10 | 1-(5-tert-Butyl-2-p-tolyl-2H-pyrazol-3-yl)-3-{6-[4-(3,4-difluoro-benzoyl)-piperazin-1-yl]-2-methyl-pyridin-3-yl}-urea methanesulfonate | 588 |
| 11 | 1-(5-tert-Butyl-2-p-tolyl-2H-pyrazol-3-yl)-3-{6-[4-(3,5-difluoro-benzoyl)-piperazin-1-yl]-2-methyl-pyridin-3-yl}-urea methanesulfonate | 588 |
| 12 | 1-(5-tert-Butyl-2-p-tolyl-2H-pyrazol-3-yl)-3-{6-[4-(2,6-dimethyl-benzoyl)-piperazin-1-yl]-2-methyl-pyridin-3-yl}-urea methanesulfonate | 580 |
| 13 | 1-(5-tert-Butyl-2-p-tolyl-2H-pyrazol-3-yl)-3-{6-[4-(2-fluoro-6-methoxy-benzoyl)-piperazin-1-yl]-2-methyl-pyridin-3-yl}-urea methanesulfonate | 600 |
| 14 | 1-(5-tert-Butyl-2-p-tolyl-2H-pyrazol-3-yl)-3-{6-[4-(2-chloro-6-fluoro-benzoyl)-piperazin-1-yl]-2-methyl-pyridin-3-yl}-urea methanesulfonate | 604 |
| 15 | 1-[6-(4-Benzoyl-piperazin-1-yl)-2-methyl-pyridin-3-yl]-3-(5-tert-butyl-2-p-tolyl-2H-pyrazol-3-yl)-urea methanesulfonate | 552 |
| 16 | 1-(5-tert-Butyl-2-p-tolyl-2H-pyrazol-3-yl)-3-{6-[4-(2-fluoro-benzoyl)-piperazin-1-yl]-2-methyl-pyridin-3-yl}-urea methanesulfonate | 570 |
| 17 | 1-(5-tert-Butyl-2-p-tolyl-2H-pyrazol-3-yl)-3-{6-[4-(2-methyl-benzoyl)-piperazin-1-yl]-2-methyl-pyridin-3-yl}-urea methanesulfonate | 566 |
| 18 | 1-(5-tert-Butyl-2-p-tolyl-2H-pyrazol-3-yl)-3-{6-[4-(2-cyano-benzoyl)-piperazin-1-yl]-2-methyl-pyridin-3-yl}-urea methanesulfonate | 577 |
| 19 | 1-(5-tert-Butyl-2-p-tolyl-2H-pyrazol-3-yl)-3-{6-[4-(2-methoxy-benzoyl)-piperazin-1-yl]-2-methyl-pyridin-3-yl}-urea methanesulfonate | 582 |
| 20 | 1-(5-tert-Butyl-2-p-tolyl-2H-pyrazol-3-yl)-3-{6-[4-(2-chloro-benzoyl)-piperazin-1-yl]-2-methyl-pyridin-3-yl}-urea methanesulfonate | 586 |
| 21 | 1-(5-tert-Butyl-2-p-tolyl-2H-pyrazol-3-yl)-3-{6-[4-(2-trifluoromethyl-benzoyl)-piperazin-1-yl]-2-methyl-pyridin-3-yl}-urea methanesulfonate | 620 |
| 22 | 1-(5-tert-Butyl-2-p-tolyl-2H-pyrazol-3-yl)-3-{6-[4-(3-fluoro-benzoyl)-piperazin-1-yl]-2-methyl-pyridin-3-yl}-urea methanesulfonate | 570 |
| 23 | 1-(5-tert-Butyl-2-p-tolyl-2H-pyrazol-3-yl)-3-{6-[4-(3-methyl-benzoyl)-piperazin-1-yl]-2-methyl-pyridin-3-yl}-urea methanesulfonate | 566 |
| 24 | 1-(5-tert-Butyl-2-p-tolyl-2H-pyrazol-3-yl)-3-{6-[4-(3-cyano-benzoyl)-piperazin-1-yl]-2-methyl-pyridin-3-yl}-urea methanesulfonate | 577 |
| 25 | 1-(5-tert-Butyl-2-p-tolyl-2H-pyrazol-3-yl)-3-{6-[4-(3-methoxy-benzoyl)-piperazin-1-yl]-2-methyl-pyridin-3-yl}-urea methanesulfonate | 582 |
| 26 | 1-(5-tert-Butyl-2-p-tolyl-2H-pyrazol-3-yl)-3-{6-[4-(3-chloro-benzoyl)-piperazin-1-yl]-2-methyl-pyridin-3-yl}-urea methanesulfonate | 586 |
| 27 | 1-(5-tert-Butyl-2-p-tolyl-2H-pyrazol-3-yl)-3-{6-[4-(3-trifluoromethyl-benzoyl)-piperazin-1-yl]-2-methyl-pyridin-3-yl}-urea methanesulfonate | 620 |
| 28 | 1-(5-tert-Butyl-2-p-tolyl-2H-pyrazol-3-yl)-3-{6-[4-(4-fluoro-benzoyl)-piperazin-1-yl]-2-methyl-pyridin-3-yl}-urea methanesulfonate | 570 |
| 29 | 1-(5-tert-Butyl-2-p-tolyl-2H-pyrazol-3-yl)-3-{6-[4-(4-methyl-benzoyl)-piperazin-1-yl]-2-methyl-pyridin-3-yl}-urea methanesulfonate | 566 |

TABLE-continued

| EXAMPLE | Compound | LCMS (ES+): m/z [M + H] |
|---|---|---|
| 30 | 1-(5-tert-Butyl-2-p-tolyl-2H-pyrazol-3-yl)-3-{6-[4-(4-methoxy-benzoyl)-piperazin-1-yl]-2-methyl-pyridin-3-yl}-urea methanesulfonate | 582 |
| 31 | 1-(5-tert-Butyl-2-p-tolyl-2H-pyrazol-3-yl)-3-{2-methyl-6-[4-(thiophene-3-carbonyl)-piperazin-1-yl]-pyridin-3-yl}-urea methanesulfonate | 558 |
| 32 | 1-(5-tert-Butyl-2-p-tolyl-2H-pyrazol-3-yl)-3-{2-methyl-6-[4-(thiophene-2-carbonyl)-piperazin-1-yl]-pyridin-3-yl}-urea methanesulfonate | 558 |
| 33 | 1-(5-tert-Butyl-2-p-tolyl-2H-pyrazol-3-yl)-3-{2-methyl-6-[4-(3-methyl-thiophene-2-carbonyl)-piperazin-1-yl]-pyridin-3-yl}-urea methanesulfonate | 572 |
| 34 | 1-(5-tert-Butyl-2-p-tolyl-2H-pyrazol-3-yl)-3-{2-methyl-6-[4-(pyridine-2-carbonyl)-piperazin-1-yl]-pyridin-3-yl}-urea methanesulfonate | 553 |
| 35 | 1-{6-[4-(2-Fluoro-benzoyl)-piperazin-1-yl]-2-methyl-pyridin-3-yl}-3-[5-(1-methyl-cyclopropyl)-2-p-tolyl-2H-pyrazol-3-yl]-urea methanesulfonate | 568 |
| 36 | 1-{6-[4-(2,6-Difluoro-benzoyl)-piperazin-1-yl]-2-methyl-pyridin-3-yl}-3-[5-(1-methyl-cyclopropyl)-2-p-tolyl-2H-pyrazol-3-yl]-urea methanesulfonate | 586 |
| 37 | 1-[5-(1-Methyl-cyclopropyl)-2-p-tolyl-2H-pyrazol-3-yl]-3-{2-methyl-6-[4-(3-methyl-thiophene-2-carbonyl)-piperazin-1-yl]-pyridin-3-yl}-urea methanesulfonate | 570 |
| 38 | 1-{6-[4-(2,2-Dimethyl-propionyl)-piperazin-1-yl]-5-methyl-pyridin-3-yl}-3-[5-(1-methyl-cyclopropyl)-2-p-tolyl-2H-pyrazol-3-yl]-urea methanesulfonate | 530 |
| 39 | 1-{6-[4-(2,6-Difluoro-benzoyl)-piperazin-1-yl]-5-methyl-pyridin-3-yl}-3-[5-(1-methyl-cyclopropyl)-2-p-tolyl-2H-pyrazol-3-yl]-urea methanesulfonate | 586 |
| 40 | 1-{6-[4-(2-Fluoro-benzoyl)-piperazin-1-yl]-5-methyl-pyridin-3-yl}-3-[5-(1-methyl-cyclopropyl)-2-p-tolyl-2H-pyrazol-3-yl]-urea methanesulfonate | 568 |
| 41 | 1-[5-(1-Methyl-cyclopropyl)-2-p-tolyl-2H-pyrazol-3-yl]-3-{5-methyl-6-[4-(1-methyl-cyclopropanecarbonyl)-piperazin-1-yl]-pyridin-3-yl}-urea methanesulfonate | 528 |
| 42 | 1-[5-(1-Methyl-cyclopropyl)-2-p-tolyl-2H-pyrazol-3-yl]-3-{5-methyl-6-[4-(3-methyl-thiophene-2-carbonyl)-piperazin-1-yl]-pyridin-3-yl}-urea methanesulfonate | 570 |
| 43 | 1-{6-[4-(2,2-Dimethyl-propionyl)-piperazin-1-yl]-5-methyl-pyridin-3-yl}-3-[5-(1-methyl-cyclohexyl)-2-p-tolyl-2H-pyrazol-3-yl]-urea methanesulfonate | 572 |
| 44 | 1-{6-[4-(2,6-Difluoro-benzoyl)-piperazin-1-yl]-5-methyl-pyridin-3-yl}-3-[5-(1-methyl-cyclohexyl)-2-p-tolyl-2H-pyrazol-3-yl]-urea methanesulfonate | 628 |
| 45 | 1-(5-tert-Butyl-2-p-tolyl-2H-pyrazol-3-yl)-3-{6-[4-(2,6-dichloro-benzoyl)-piperazin-1-yl]-2-methyl-pyridin-3-yl}-urea methanesulfonate (rxn time = 5 d, HOBt (0.59 mmol) in place of DMAP) | 620 |

EXAMPLE 46

1-(5-tert-butyl-2-p-tolyl-2H-pyrazole-3-yl)-3-{6-[4-(2,6-difluoro-benzoyl)-piperazin-1-yl]pyridin-3-yl}-urea Place 1-(5-tert-butyl-2-p-tolyl-2H-pyrazol-3-yl)-3-(6-piperazin-1-yl-pyridin-3-yl)-urea (48 mg, 0.111 mmol), 2,6-difluorobenzoic acid (21 mg, 0.133 mmol), and 4-N,N-dimethylaminopyridine (3 mg, 0.022 mmol) in acetonitrile (5 mL). Add O-(7-azabenzotriazole-1-yl)-N,N,N',N'-tetramethyluronium hexafluorophosphate (HATU) (50 mg, 0.133 mmol) and heat to 70° C. for 19 hours. Cool to room temperature and add $CH_2Cl_2$ and water. Separate organic layer and extract aqueous with $CH_2Cl_2$ (2×25 mL). Combine organics, dry over $Mg_2SO_4$, filter, and concentrate under reduced pressure. Subject residue to silica gel chromatography eluting with 0-60% EtOAc:hexane to yield the title compound. LCMS(ES): m/z=574.2 [M+H].

Prepare the following compounds using procedures substantially analogous to those described above.

TABLE

| EXAMPLE | Compound | MS (ES+): m/z [M + H] |
|---|---|---|
| 47 | 1-(5-tert-Butyl-2-p-tolyl-2H-pyrazol-3-yl)-3-{6-[4-(2,6-dichloro-benzoyl)-piperazin-1-yl]-pyridin-3-yl}-urea | 608 |
| 48 | 1-(5-tert-Butyl-2-p-tolyl-2H-pyrazol-3-yl)-3-[6-(4-cyclopropanecarbonyl-piperazin-1-yl)-pyridin-3-yl]-urea | 502.2 |
| 49 | 1-(5-tert-Butyl-2-p-tolyl-2H-pyrazol-3-yl)-3-{6-[4-(3-methyl-thiophene-2-carbonyl)-piperazin-1-yl]-pyridin-3-yl}-urea | 558.3 |

EXAMPLE 50

1-(5-tert-butyl-2-p-tolyl-2H-pyrazol-3-yl-3-{6-[4-(2,2-dimethyl-propionyl)-piperazin-1-yl]-pyridin-3-yl}-urea Place 1-(5-tert-butyl-2-p-tolyl-2H-pyrazol-3-yl)-3-(6-piperazin-1-yl-pyridin-3-yl)-urea (200 mg, 0.461 mmol), triethylamine (0.071 mL, 0.507 mmol), and 4-N,N-dimethylaminopyridine (6 mg, 0.051 mmol) in $CH_2Cl_2$ (10 mL). Add 2,2-dimethyl-propionyl chloride (0.062 mL, 0.507 mmol) and stir at room temperature for 17 h. Subject residue to silica gel chromatography eluting with 0-100% EtOAc:hexane to yield 175 mg (73%) of the title compound. MS(ES+): m/z=518.2 [M+H].

Prepare the following compounds using a procedure substantially analogous to that described above.

EXAMPLE 53

1-(5-tert-Butyl-2-p-tolyl-2H-pyrazol-3-yl)-3-{6-[4-(3-methyl-pentanoyl)-piperazin-1-yl]-pyridin-3-yl}-urea React 1-(5-tert-butyl-2-p-tolyl-2H-pyrazol-3-yl)-3-(6-piperazin-1-yl-pyridin-3-yl)-urea (0.20 g, 0.46 mmol) with 3-methyl-pentanoic acid (0.059 g, 0.51 mmol), 1-hydroxybenzotriazole hydrate (0.06 g, 0.46 mmol) and polymer supported carbodiimide (0.83 g, 1.0 mmol), suspended in a mixture $CH_2Cl_2$/DMF (18/1, mL). Stir the mixture at room temperature overnight and then filter and wash the resin with $CH_2Cl_2$. Concentrate and purify the residue with a SCX cartridge eluting with $NH_4OH/CH_3OH$ 2N to yield 135 mg (55%) of the title compound as a pale pink solid. MS(ES+): m/z=532 [M+H].

Prepare the following compounds using a procedure substantially analogous to that described above.

TABLE

| EXAMPLE | Compound | MS (ES+): m/z [M + H] |
|---|---|---|
| 51 | 1-(5-tert-butyl-2-p-tolyl-2H-pyrazol-3-yl)-3-{6-[4-(2,2-dimethyl-propionyl)-piperazin-1-yl]-5-methyl-pyridin-3-yl}-urea | 532.3 |
| 52 | 1-(5-tert-butyl-2-p-tolyl-2H-pyrazol-3-yl)-3-{5-chloro-6-[4-(2,2-dimethyl-propionyl)-piperazin-1-yl]-pyridin-3-yl}-urea | 552.2 |

TABLE

| EXAMPLE | Compound | MS(ES+): m/z [M + H] |
|---|---|---|
| 54 | 1-(5-tert-Butyl-2-p-tolyl-2H-pyrazol-3-yl)-3-{6-[4-(2-cyclopentyl-acetyl)-piperazin-1-yl]-pyridin-3-yl}-urea | 544 |
| 55 | 1-(5-tert-Butyl-2-p-tolyl-2H-pyrazol-3-yl)-3-{6-[4-(2,2,3,3-tetramethyl-cyclopropanecarbonyl)-piperazin-1-yl]-pyridin-3-yl}-urea | 558 |
| 56 | 1-(5-tert-Butyl-2-p-tolyl-2H-pyrazol-3-yl)-3-{6-[4-(1-methyl-cyclopropanecarbonyl)-piperazin-1-yl]-pyridin-3-yl}-urea | 516 |
| 57 | 1-(5-tert-Butyl-2-p-tolyl-2H-pyrazol-3-yl)-3-[6-(4-cyclobutanecarbonyl-piperazin-1-yl)-pyridin-3-yl]-urea | 516 |
| 58 | 1-(5-tert-Butyl-2-p-tolyl-2H-pyrazol-3-yl)-3-{6-[4-(1-methyl-cyclohexanecarbonyl)-piperazin-1-yl]-pyridin-3-yl}-urea | 558 |
| 59 | 1-(5-tert-Butyl-2-p-tolyl-2H-pyrazol-3-yl)-3-{6-[4-(2,2-dimethyl-pentanoyl)-piperazin-1-yl]-pyridin-3-yl}-urea | 546 |
| 60 | 1-(5-tert-Butyl-2-p-tolyl-2H-pyrazol-3-yl)-3-{6-[4-(2-methyl-cyclopropanecarbonyl)-piperazin-1-yl]-pyridin-3-yl}-urea | 516 |

EXAMPLE 61

1-(5-tert-Butyl-2-p-tolyl-2H-pyrazol-3-yl)-3-{6-[4-(2,6-difluoro-benzoyl)-piperazin-1-yl]-5-methyl-pyridin-3-yl}-urea Place 1-(5-tert-butyl-2-p-tolyl-2H-pyrazol-3-yl)-3-(5-methyl-6-piperazin-1-yl-pyridin-3-yl)-urea (300 mg, 0.670 mmol), N-(3-dimethylaminopropyl)-N'-ethylcarbodiimide hydrochloride (154 mg, 0.804 mmol), 2,6-difluorobenzoic acid (127 mg, 0.804 mmol), and 4-N,N-dimethylaminopyridine (15 mg, 0.134 mmol) in acetonitrile (10 mL). Heat the reaction to 60° C. for 18 hours. Cool reaction to room temperature and add $CH_2Cl_2$ and water. Separate organic layer and extract aqueous layer with $CH_2Cl_2$ (2×20 mL). Combine organic layers, dry over $Mg_2SO_4$, filter, and concentrate under reduced pressure. Subject residue to silica gel chromatography eluting with 10-70% EtOAc:hexane to yield the title compound. MS(ES+): m/z=588.3 [M+H].

Prepare the following compounds using a procedure substantially analogous to that described above.

TABLE

| EXAMPLE | Name | MS(ES+): m/z [M + H] |
|---|---|---|
| 62 | 1-(5-tert-Butyl-2-p-tolyl-2H-pyrazol-3-yl)-3-[6-(4-cyclopropanecarbonyl-piperazin-1-yl)-5-methyl-pyridin-3-yl]-urea | 516.3 |
| 63 | 1-(5-tert-Butyl-2-p-tolyl-2H-pyrazol-3-yl)-3-{5-methyl-6-[4-(3-methyl-thiophene-2-carbonyl)-piperazin-1-yl]-pyridin-3-yl}-urea | 572.3 |
| 64 | 1-(5-tert-butyl-2-p-tolyl-2H-pyrazol-3-yl)-3-{5-chloro-6-[4-(2,6-difluoro-benzoyl)-piperazin-1-yl]-pyridin-3-yl}-urea | 608.0 |
| 65 | 1-(5-tert-Butyl-2-p-tolyl-2H-pyrazol-3-yl)-3-[5-chloro-6-(4-cyclopropanecarbonyl-piperazin-1-yl)-pyridin-3-yl]-urea | 536.2 |
| 66 | 1-(5-tert-Butyl-2-p-tolyl-2H-pyrazol-3-yl)-3-{5-chloro-6-[4-(3-methyl-thiophene-2-carbonyl)-piperazin-1-yl]-pyridin-3-yl}-urea | 592.0 |
| 67 | 1-{6-[4-(2,6-difluoro-benzoyl)-piperazin-1-yl]-pyridin-3-yl}-3-(2-p-tolyl-5-trimethylsilanyl-2H-pyrazol-3-yl)-urea | 590.2 |

EXAMPLE 68

1-(5-tert-Butyl-2-p-tolyl-2H-pyrazol-3-yl)-3-{6-[4-(2,6-difluoro-benzoyl)-piperazin-1-yl]-2-methyl-pyridin-3-yl}-urea monomethanesulfonate

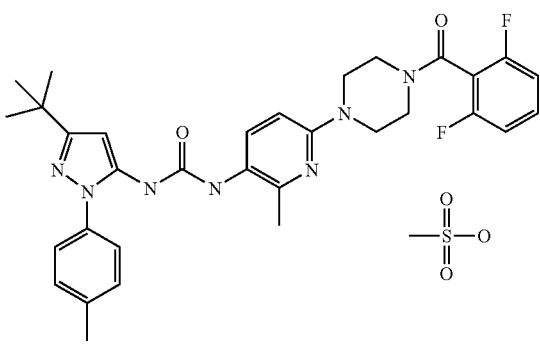

Add [4-(5-amino-6-methyl-pyridin-2-yl)-piperazin-1-yl]-(2,6-difluoro-phenyl)-methanone (1.00 equiv, 601.77 mmol, 200.00 g), 5-tert-butyl-2-p-tolyl-2H-pyrazol-3-yl)-carbamic acid, 2,2,2-trichloro-ethyl ester (1.00 equiv, 602.88 mmol, 244.00 g), N,N-dimethylaminopyridine (60.47 mmol, 7.50 g), diisopropylethylamine (229.36 mmol, 40.00 mL, 29.64 g), DMSO (1.00 L) to two 5 L three neck flask with overhead stirring. Heat slowly and maintain at 60~65° C. Add DMSO (250 mL) and continue stirring at ~65° C. for 1 hour. Add MTBE then maintain at ~60° C. for 0.5 hour. Cool to room temperature. Collect solids by filtration and combine. Rinse cake with MTBE and allow to dry under reduced pressure overnight. Dissolve the material in 9 L of methanol, then treat with activated carbon (65 g) at reflux for 1 hour. Filter the mixture was through Celite®. Concentrate the filtrate, then solvent exchange into ethyl acetate. Filter, rinse with ethyl acetate, heptanes, and dry at 40° C. under reduced pressure to afford 1-(5-tert-butyl-2-p-tolyl-2H-pyrazol-3-yl)-3-{6-[4-(2,6-difluoro-benzoyl)-piperazin-1-yl]-2-methyl-pyridin-3-yl}-urea (490 g).

Charge 1-(5-tert-butyl-2-p-tolyl-2H-pyrazol-3-yl)-3-{6-[4-(2,6-difluoro-benzoyl)-piperazin-1-yl]-2-methyl-pyridin-3-yl}-urea (1.00 equiv, 600.67 mmol, 353.00 g), and methanol (3.50 L) to a 5 L flask. Heat the mixture was to 50-60° C. Add methanesulfonic acid (1.00 equiv, 603.49 mmol, 39.56 mL, 58.00 g) in 250 mL of ethyl acetate drop wise. Stir the solution for 0.5 hour at ~50° C., then remove heating source. Stir for 5 hours, then filter. Concentrate filtrate under reduced pressure. Add ethyl acetate (300 mL) and concentrate under reduced pressure. Add an additional 300 mL of ethyl acetate was added concentrate under reduced pressure. Add 2 L of diethyl ether then stir for 15 minutes. Allow to stand overnight. Stir for 3 hours then filter. Rinse diethyl ether and heptane, then dry under reduced pressure at ~40° C. to afford the title compound (391.4 g).

EXAMPLE 69

1-(5-tert-Butyl-2-p-tolyl-2H-pyrazol-3-yl)-3-[6-((trans)-4-cyclopropanecarbonyl-2,5-dimethyl-piperazin-1-yl)-5-methyl-pyridin-3-yl]-urea

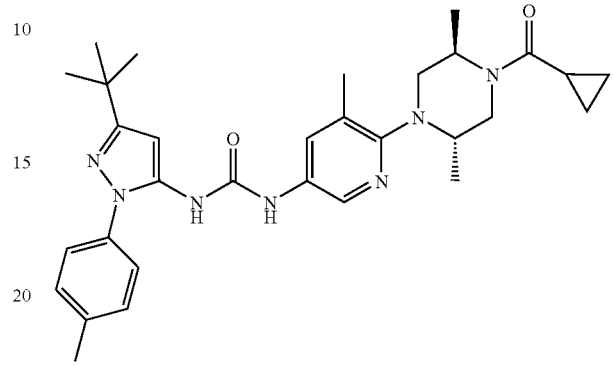

Dissolve compound of rac-[(trans)-4-(5-amino-3-methyl-pyridin-2-yl)-2,5-dimethyl-piperazin-1-yl]-cyclopropyl-methanone, (Preparation 9, 0.1 g, 0.35 mmol) and 5-tert-butyl-2-p-tolyl-2H-pyrazol-3-yl)-carbamic acid, 2,2,2-trichloro-ethyl ester (0.283 g, 0.7 mmol) in DMSO (3 mL) and DIEA (0.12 mL, 0.7 mmol). Heat in a sealed tube at 80° C. for 15 hours. Allow to cool down and pour into ice water. Extract with AcOEt several times. Join organics and wash with saturated aq. sodium chloride solution, dry over $Na_2SO_4$ to give a residue. Subject residue to silica gel chromatography eluting with AcOEt in hexane 50-90% to give 0.09 g of rac-1-(5-tert-butyl-2-p-tolyl-2H-pyrazol-3-yl)-3-[6-((trans)-4-cyclopropanecarbonyl-2,5-dimethyl-piperazin-1-yl)-5-methyl-pyridin-3-yl]-urea (47% yield) as a solid. MS(ES+): m/z=544.5 [M+H].

Subject crude to chiral chromatography resolution using column Chirapack AS eluting with hexane-DMEA 0.2%: EtOH 25%. t 3.78 min. MS(ES+): m/z=544.5 [M+H].

EXAMPLE 70

1-(5-tert-Butyl-2-p-tolyl-2H-pyrazol-3-yl)-3-{6-[4-(2,2-dimethyl-propionyl)piperazin-1-yl]-4-methyl-pyridin-3-yl}-urea Add (5-tert-butyl-2-p-tolyl-2H-pyrazol-3-yl)-carbamic acid, 2,2,2-trichloro-ethyl ester (Preparation 38, 0.32 mmol, 0.1 r) over a solution of 1-[4-(5-amino-4-methyl-pyridin-2-yl)-piperazin-1-yl]-2,2-dimethyl-propan-1-one (0.3 mmol, 0.08 g) and potassium carbonate (0.3 mmol, 0.05 g) in acetonitrile (3 mL), and stir the solution for 4 hours at 80° C. Add water and extract with $CH_2Cl_2$. Combine the organic layers and wash with saturated aq. sodium chloride. Dry over sodium sulfate, filter, and concentrate under reduced pressure to give a residue. Subject residue to silica gel chromatography eluting with hexanes/ethyl acetate in gradient (from 20% to 80%). MS(ES+): m/z=532 [M+H].

Prepare the following compounds using a procedure substantially analogous to that described above.

TABLE

| EXAMPLE | Compound | MS(ES+): m/z [M + H] |
|---|---|---|
| 71 | 1-(5-tert-Butyl-2-p-tolyl-2H-pyrazol-3-yl)-3-{4-methyl-6-[4-(1-methyl-cyclopropanecarbonyl)-piperazin-1-yl]-pyridin-3-yl}-urea | 530 |
| 72 | 1-(5-tert-Butyl-2-p-tolyl-2H-pyrazol-3-yl)-3-{4-chloro-6-[4-(2,2-dimethyl-propionyl)-piperazin-1-yl]-pyridin-3-yl}-urea | 552 |
| 73 | 1-(5-tert-Butyl-2-p-tolyl-2H-pyrazol-3-yl)-3-{6-[4-(2,2-dimethyl-propionyl)-piperazin-1-yl]-5-trifluoromethyl-pyridin-3-yl}-urea | 586.4 |

EXAMPLE 74

1-(5-tert-Butyl-2-p-tolyl-2H-pyrazol-3-yl)-3-{5-chloro-6-[4-(1-methyl-cyclopropanecarbonyl)-piperazin-1-yl]-pyridin-3-yl}-urea Over a solution of 1-(5-tert-butyl-2-p-tolyl-2H-pyrazol-3-yl)-3-(5-chloro-6-piperazin-1-yl-pyridin-3-yl)-urea hydrochloride (1.6 mmol, 0.7 g), in 5 mL of $CH_2Cl_2$ add 1-methyl-cyclopropanecarboxylic acid (1.6 mmol, 0.2 g), 1-hydroxy-1H-benzotriazol hydrate (1.8 mmol, 0.2 g), N-ethyl-N'-(3-domethylaminopropyl) carbodiimide hydrochloride (1.8 mmol, 0.3 g) and triethylamine (4.8 mmol, 0.7 mL). Stir the solution for 24 hours at room temperature. Add water and extract with $CH_2Cl_2$. Combine the organic layers and wash with saturated aq. sodium chloride solution, dry over sodium sulfate, filter, and concentrate under reduced pressure to give a residue. Subject residue to silica gel chromatography eluting with hexanes/ethyl acetate in gradient (from 20% to 80%). MS(ES+): m/z=550 [M+H].

Prepare the following compound using a procedure substantially analogous to that described above.

TABLE

| EXAMPLE | Name | LCMS ES+ (m/z) [M + H] |
|---|---|---|
| 75 | 1-(5-tert-Butyl-2-p-tolyl-2H-pyrazol-3-yl)-3-{5-methyl-6-[4-(1-methyl-cyclopropanecarbonyl)-piperazin-1-yl]-pyridin-3-yl}-urea | 530 |

EXAMPLE 76

1-(5-tert-Butyl-2-p-tolyl-2H-pyrazol-3-yl)-3-{6-[4-(2,6-difluoro-benzoyl)-piperidin-4-ylamino]-pyridin-3-yl}-urea

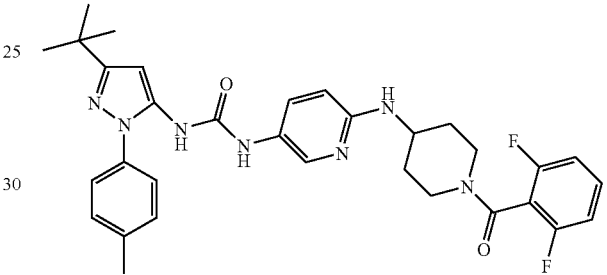

Stir 11-(5-tert-butyl-2-p-tolyl-2H-pyrazol-3-yl)-3-[6-(piperidin-4-ylamino)-pyridin-3-yl]-urea (0.22 mmol, 0.1 g), 2,6-difluoro-benzoyl chloride (0.2 mmol, 0.03 mL), and triethylamine (0.2 mmol, 0.03 mL) in 3 mL of acetonitrile overnight at room temperature. Add $CH_2Cl_2$ and wash with saturated aq. sodium chloride and water. Dry over sodium sulfate, filter, and concentrate under reduced pressure. Subject residue to silica gel chromatography eluting with $CH_2Cl_2$:MeOH in gradient (from 0.5 to 10%). MS(ES+): m/z=588 [M+H].

EXAMPLE 77

1-(5-tert-Butyl-2-p-tolyl-2H-pyrazol-3-yl)-3-{2-methyl-6-[1-(1-methyl-cyclopropanecarbonyl)-piperidin-4-yloxy]-pyridin-3-yl}-urea

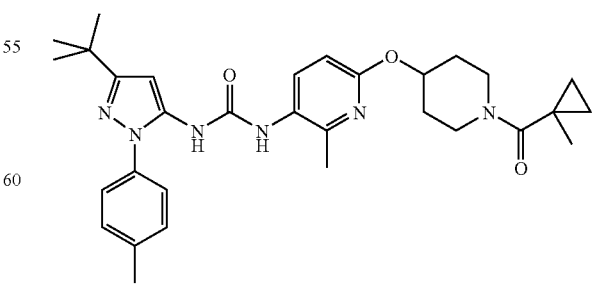

Stir a reaction mixture of 4-{5-[3-(5-tert-butyl-2-p-tolyl-2H-pyrazol-3-yl)-ureido]-6-methyl-pyridin-2-yloxy}-piperidine (93 mg, 0.2 mmol), 1-methyl cyclopropyl1-carboxylic acid (40 mg, 0.4 mmol), HOBt (30 mg, 0.25 mmol), and DCC (80 mg, 0.4 mmol) in dichloromethane (2 mL) at 22° C. for 18 hours. Filter, then subject to silica gel chromatography eluting with hexanes and ethyl acetate to provide a white solid (111 mg, 100% yield). MS(ES+): m/z=545.3[M+H].

Prepare the following compounds using a procedure substantially analogous to that described above.

TABLE

| EXAMPLE | Compound | MS(ES+): m/z [M + H] |
|---|---|---|
| 78 | 1-(5-tert-Butyl-2-p-tolyl-2H-pyrazol-3-yl)-3-{6-[1-(2-fluoro-benzoyl)-piperidin-4-yloxy]-2-methyl-pyridin-3-yl}-urea | 585.3 |
| 79 | 1-(5-tert-Butyl-2-p-tolyl-2H-pyrazol-3-yl)-3-{6-[1-(2,6-difluoro-benzoyl)-piperidin-4-yloxy]-2-methyl-pyridin-3-yl}-urea | 603.3 |
| 80 | 1-(5-tert-Butyl-2-p-tolyl-2H-pyrazol-3-yl)-3-{6-[1-(2,4-difluoro-benzoyl)-piperidin-4-yloxy]-2-methyl-pyridin-3-yl}-urea | 603.3 |
| 81 | 1-[5-tert-Butyl-2-(6-methyl-pyridin-3-yl)-2H-pyrazol-3-yl]-3-{2-methyl-6-[4-(3-methyl-thiophene-2-carbonyl)-piperazin-1-yl]-pyridin-3-yl}-urea | 573.3 |
| 82 | 1-[5-tert-Butyl-2-(6-methyl-pyridin-3-yl)-2H-pyrazol-3-yl]-3-{6-[4-(2-chloro-benzoyl)-piperazin-1-yl]-2-methyl-pyridin-3-yl}-urea | 587.3 |
| 83 | 1-[5-tert-Butyl-2-(6-methyl-pyridin-3-yl)-2H-pyrazol-3-yl]-3-{6-[4-(2-fluoro-benzoyl)-piperazin-1-yl]-2-methyl-pyridin-3-yl}-urea | 571.2 |
| 84 | 1-{2-Methyl-6-[4-(3-methyl-thiophene-2-carbonyl)-piperazin-1-yl]-pyridin-3-yl}-3-[2-(6-methyl-pyridin-3-yl)-5-(1-trifluoromethyl-cyclopropyl)-2H-pyrazol-3-yl]-urea | 625.3 |
| 85 | 1-{6-[4-(2-Chloro-benzoyl)-piperazin-1-yl]-2-methyl-pyridin-3-yl}-3-[2-(6-methyl-pyridin-3-yl)-5-(1-trifluoromethyl-cyclopropyl)-2H-pyrazol-3-yl]-urea | 639.3 |
| 86 | 1-{6-[4-(2-Fluoro-benzoyl)-piperazin-1-yl]-2-methyl-pyridin-3-yl}-3-[2-(6-methyl-pyridin-3-yl)-5-(1-trifluoromethyl-cyclopropyl)-2H-pyrazol-3-yl]-urea | 623.3 |
| 87 | 1-{6-[4-(2,6-Difluoro-benzoyl)-piperazin-1-yl]-2-methyl-pyridin-3-yl}-3-[2-(6-methyl-pyridin-3-yl)-5-(1-trifluoromethyl-cyclopropyl)-2H-pyrazol-3-yl]-urea | 641.3 |
| 88 | 1-(5-tert-Butyl-2-p-tolyl-2H-pyrazol-3-yl)-3-{6-[1-(2-fluoro-benzoyl)-piperidin-4-yloxy]-pyridin-3-yl}-urea | 571.3 |
| 89 | 1-(5-tert-Butyl-2-p-tolyl-2H-pyrazol-3-yl)-3-{6-[1-(2,6-difluoro-benzoyl)-piperidin-4-yloxy]-pyridin-3-yl}-urea | 589.3 |
| 90 | 1-(5-tert-Butyl-2-p-tolyl-2H-pyrazol-3-yl)-3-{6-[1-(2,4-difluoro-benzoyl)-piperidin-4-yloxy]-pyridin-3-yl}-urea | 589.3 |
| 91 | 1-(5-tert-Butyl-2-p-tolyl-2H-pyrazol-3-yl)-3-{6-[1-(3-methyl-thiophene-2-carbonyl)-piperidin-4-yloxy]-pyridin-3-yl}-urea | 573.3 |
| 92 | 1-(5-tert-Butyl-2-p-tolyl-2H-pyrazol-3-yl)-3-{6-[1-(5-chloro-thiophene-2-carbonyl)-piperidin-4-yloxy]-pyridin-3-yl}-urea | 593.0 |
| 93 | 1-(5-tert-Butyl-2-p-tolyl-2H-pyrazol-3-yl)-3-[6-(1-cyclopropanecarbonyl-piperidin-4-yloxy)-5-methyl-pyridin-3-yl]-urea | 531.2 |
| 94 | 1-(5-tert-Butyl-2-p-tolyl-2H-pyrazol-3-yl)-3-{6-[1-(2,4-difluoro-benzoyl)-piperidin-4-yloxy]-5-methyl-pyridin-3-yl}-urea | 603.3 |
| 95 | 1-(5-tert-Butyl-2-p-tolyl-2H-pyrazol-3-yl)-3-{5-methyl-6-[1-(3-methyl-thiophene-2-carbonyl)-piperidin-4-yloxy]-pyridin-3-yl}-urea | 587.3 |
| 96 | 1-(5-tert-Butyl-2-p-tolyl-2H-pyrazol-3-yl)-3-{6-[1-(5-chloro-thiophene-2-carbonyl)-piperidin-4-yloxy]-5-methyl-pyridin-3-yl}-urea | 607.0 |
| 97 | 1-(5-tert-Butyl-2-p-tolyl-2H-pyrazol-3-yl)-3-{6-[1-(2,5-dichloro-thiophene-3-carbonyl)-piperidin-4-yloxy]-5-methyl-pyridin-3-yl}-urea | 641.0 |
| 98 | 1-(5-tert-Butyl-2-p-tolyl-2H-pyrazol-3-yl)-3-{6-[4-(2,4-difluoro-benzoyl)-piperazin-1-yl]-pyridin-3-yl}-urea | 574.0 |

EXAMPLE 99

1-(5-tert-Butyl-2-p-tolyl-2H-pyrazol-3-yl)-3-{5-chloro-6-[1-(2-fluoro-benzoyl)-piperidin-4-yloxy]oxy-pyridin-3-yl}-urea mesylate

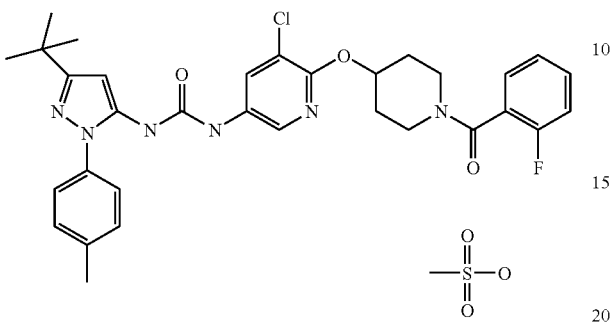

Prepare the free base using a procedure substantially analogous to the procedure above. Convert to the mesylate salt by treating a solution or slurry of the free amine in dichloromethane (1 mL) and MeOH (5 mL) with methane sulfonic acid (1 equiv., 17.66 mg 0.183 mL). Agitate the resulting mixture, concentrate and dry under reduced pressure to afford the salt. MS(ES+): m/z=605.0 [M+H] (as free base).

Prepare the following mesylate salts using a procedure substantially analogous to that described above.

TABLE

| EXAMPLE | Name | MS(ES+): m/z [M + H] |
|---|---|---|
| 100 | 1-(5-tert-Butyl-2-p-tolyl-2H-pyrazol-3-yl)-3-{5-chloro-6-[1-(3-methyl-thiophene-2-carbonyl)-piperidin-4-yloxy]-pyridin-3-yl}-urea mesylate | 607.0 |
| 101 | 1-(5-tert-Butyl-2-p-tolyl-2H-pyrazol-3-yl)-3-[5-chloro-6-(1-cyclopropanecarbonyl-piperidin-4-yloxy)-pyridin-3-yl]-urea mesylate | 551.2 |
| 102 | 1-{6-[4-(2,6-Difluoro-benzoyl)-piperazin-1-yl]-2-methyl-pyridin-3-yl}-3-(5-pentafluoroethyl-2-p-tolyl-2H-pyrazol-3-yl)-urea mesylate | 650.0 |
| 103 | 1-{6-[4-(2-Fluoro-benzoyl)-piperazin-1-yl]-2-methyl-pyridin-3-yl}-3-[2-p-tolyl-5-(1-trifluoromethyl-cyclopropyl)-2H-pyrazol-3-yl]-urea mesylate | 622.2 |
| 104 | 1-{6-[4-(2,6-Difluoro-benzoyl)-piperazin-1-yl]-2-methyl-pyridin-3-yl}-3-[2-p-tolyl-5-(1-trifluoromethyl-cyclopropyl)-2H-pyrazol-3-yl]-urea mesylate | 640.0 |
| 105 | 1-{6-[1-(2-Fluoro-benzoyl)-piperidin-4-yloxy]-5-methyl-pyridin-3-yl}-3-[2-p-tolyl-5-(2,2,2-trifluoro-1-methyl-1-trifluoromethyl-ethyl)-2H-pyrazol-3-yl]-urea mesylate | 693.0 |
| 106 | 1-[5-tert-Butyl-2-(6-methyl-pyridin-3-yl)-2H-pyrazol-3-yl]-3-{6-[4-(2,6-difluoro-benzoyl)-piperazin-1-yl]-2-methyl-pyridin-3-yl}-urea mesylate | 589.3 |
| 107 | 1-(5-tert-Butyl-2-p-tolyl-2H-pyrazol-3-yl)-3-{6-[1-(2-fluoro-benzoyl)-piperidin-4-yloxy]-2-methyl-pyridin-3-yl}-urea mesylate | 585.3 |
| 108 | 1-(5-tert-Butyl-2-p-tolyl-2H-pyrazol-3-yl)-3-{6-[1-(2,6-difluoro-benzoyl)-piperidin-4-yloxy]-2-methyl-pyridin-3-yl}-urea mesylate | 603.3 |
| 109 | 1-(5-tert-Butyl-2-p-tolyl-2H-pyrazol-3-yl)-3-{6-[1-(2,4-difluoro-benzoyl)-piperidin-4-yloxy]-2-methyl-pyridin-3-yl}-urea mesylate | 603.3 |
| 110 | 1-[5-tert-Butyl-2-(6-methyl-pyridin-3-yl)-2H-pyrazol-3-yl]-3-{2-methyl-6-[4-(3-methyl-thiophene-2-carbonyl)-piperazin-1-yl]-pyridin-3-yl}-urea mesylate | 573.3 |
| 111 | 1-[5-tert-Butyl-2-(6-methyl-pyridin-3-yl)-2H-pyrazol-3-yl]-3-{6-[4-(2-chloro-benzoyl)-piperazin-1-yl]-2-methyl-pyridin-3-yl}-urea mesylate | 587.3 |
| 112 | 1-[5-tert-Butyl-2-(6-methyl-pyridin-3-yl)-2H-pyrazol-3-yl]-3-{6-[4-(2-fluoro-benzoyl)-piperazin-1-yl]-2-methyl-pyridin-3-yl}-urea mesylate | 571.2 |
| 113 | 1-{2-Methyl-6-[4-(3-methyl-thiophene-2-carbonyl)-piperazin-1-yl]-pyridin-3-yl}-3-[2-(6-methyl-pyridin-3-yl)-5-(1-trifluoromethyl-cyclopropyl)-2H-pyrazol-3-yl]-urea mesylate | 625.3 |
| 114 | 1-{6-[4-(2-Chloro-benzoyl)-piperazin-1-yl]-2-methyl-pyridin-3-yl}-3-[2-(6-methyl-pyridin-3-yl)-5-(1-trifluoromethyl-cyclopropyl)-2H-pyrazol-3-yl]-urea mesylate | 639.3 |

TABLE-continued

| EXAMPLE | Name | MS(ES+): m/z [M + H] |
|---|---|---|
| 115 | 1-{6-[4-(2-Fluoro-benzoyl)-piperazin-1-yl]-2-methyl-pyridin-3-yl}-3-[2-(6-methyl-pyridin-3-yl)-5-(1-trifluoromethyl-cyclopropyl)-2H-pyrazol-3-yl]-urea mesylate | 623.3 |
| 116 | 1-{6-[4-(2,6-Difluoro-benzoyl)-piperazin-1-yl]-2-methyl-pyridin-3-yl}-3-[2-(6-methyl-pyridin-3-yl)-5-(1-trifluoromethyl-cyclopropyl)-2H-pyrazol-3-yl]-urea mesylate | 641.3 |

EXAMPLE 117

1-{6-[1-(2-Fluoro-benzoyl)-piperidin-4-yloxy]-5-methyl-pyridin-3-yl}-3-[2-p-tolyl-5-(2,2,2-trifluoro-1-methyl-1-trifluoromethyl-ethyl)-2H-pyrazol-3-yl]-urea

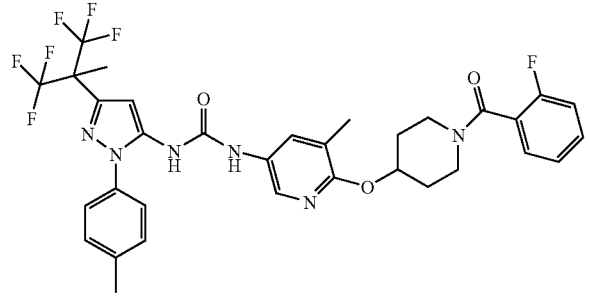

Bubble nitrogen gas through a solution of [2-p-tolyl-5-(2,2,2-trifluoro-1-methyl-1-trifluoromethyl-ethyl)-2H-pyrazol-3-yl]-carbamic acid 2,2,2-trichloro-ethyl ester (Preparation 37, 95 mg, 0.185 mmol) and [4-(5-Amimo-3-methyl-pyridin-2-yloxy)-piperidin-1-yl]-(2-fluoro-phenyl)-methanone (Preparation 19, 61 mg, 0.185 mmol) in DMSO (3 mL) for 5 min. Next, add N,N-diisopropylethylamine (0.08 mL, 0.463 mmol). Stir at 70° C. overnight, then pour into CH$_2$Cl$_2$ (75 mL) and wash over a 10 g SCX MegaBond Elute column. Wash column with CH$_2$Cl$_2$ (3×35 mL), MeOH (2×50 mL) and 2 M NH$_3$ in MeOH (3×50 mL). Combine desired fractions and concentrate. Subject residue to silica gel chromatography eluting with CH$_2$Cl$_2$ and a 10% MeOH 90% CH$_2$Cl$_2$ solution to give the title compound as a white solid (69 mg, 54% yield). MS(ES+): m/z=693.5 [M+H].

EXAMPLE 118

1-{6-[4-(2,6-Difluoro-benzoyl)-piperazin-1-yl]-2-methyl-pyridin-3-yl}-3-[5-(2-fluoro-1-fluoromethyl-1-methyl-ethyl)-2-p-tolyl-2H-pyrazol-3-yl]-urea Stir 1-[5-(2-Fluoro-1-fluoromethyl-1-methyl-ethyl)-2-p-tolyl-2H-pyrazol-3-yl]-3-(2-methyl-6-piperazin-1-yl-pyridin-3-yl)-urea hydrochloride (0.85 mmol, 0.5 g), 2,6-difluorobenzoyl chloride (0.85 mmol, 0.1 mL) and triethylamine (2.6 mmol, 0.4 mL) in 5 mL of CH$_2$Cl$_2$ at room temperature overnight. Add water and extract in CH$_2$Cl$_2$. Wash organic layer with saturated aq. sodium chloride solution. Dry over anhydrous sodium sulfate and concentrate under reduced pressure. Subject residue to silica gel chromatography eluting with using hexanes/ethyl acetate (20%-70%). MS(ES): m/z=624 [M+H].

Prepare the following compounds using a procedure substantially analogous to that described above.

TABLE

| EX-AMPLE | Compound | MS(ES+): m/z [M + H] |
|---|---|---|
| 119 | 1-[5-(2-Fluoro-1-fluoromethyl-1-methyl-ethyl)-2-p-tolyl-2H-pyrazol-3-yl]-3-{2-methyl-6-[4-(2-methyl-benzoyl)-piperazin-1-yl]-pyridin-3-yl}-urea | 602 |
| 120 | 1-{6-[4-(2,6-Difluoro-benzoyl)-piperazin-1-yl]-2-methyl-pyridin-3-yl}-3-[5-(2-fluoro-1,1-dimethyl-ethyl)-2-p-tolyl-2H-pyrazol-3-yl]-urea | 606 |

EXAMPLE 121

1-(5-tert-Butyl-2-p-tolyl-2H-pyrazol-3-yl)-3-{6-[4-(2-cyclopentyl-acetyl)-piperazin-1-yl]-pyridin-3-yl}-urea methanesulfonate

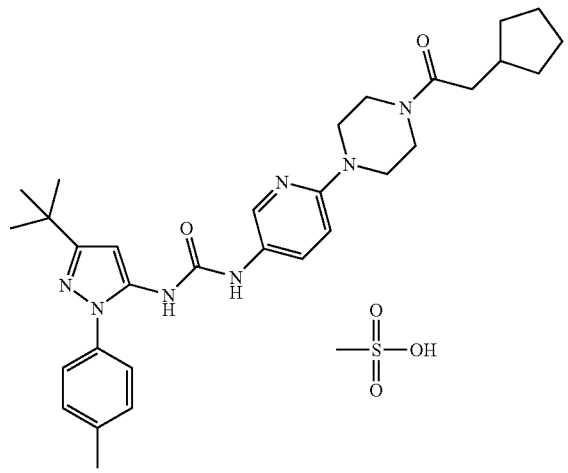

Add 0.10 mL of 1N solution of methanesulfonic acid in CH$_2$Cl$_2$/MeOH (95/5) to a stirred solution of 1-(5-tert-butyl-2-p-tolyl-2H-pyrazol-3-yl)-3-{6-[4-(2-cyclopentyl-acetyl)-piperazin-1-yl]-pyridin-3-yl}-urea in 2 mL of CH$_2$Cl$_2$/MeOH (95/5). Stir the mixture at room temperature for 20 minutes, and then evaporate solvents by N₂ flushing. Triturate the salt with Et₂O, filter and dry to give the title compound. MS(ES+): m/z=544 [M+H].

Prepare the following compounds using a procedure substantially analogous to that described above.

TABLE

| EXAMPLE | Compound | MS(ES+): m/z [M + H] |
|---|---|---|
| 122 | 1-(5-tert-Butyl-2-p-tolyl-2H-pyrazol-3-yl)-3-[6-(4-cyclobutanecarbonyl-piperazin-1-yl)-pyridin-3-yl]-urea methanesulfonate | 516 |
| 123 | 1-(5-tert-Butyl-2-p-tolyl-2H-pyrazol-3-yl)-3-{6-[4-(3-methyl-pentanoyl)-piperazin-1-yl]-pyridin-3-yl}-urea methanesulfonate | 532 |
| 124 | 1-(5-tert-Butyl-2-p-tolyl-2H-pyrazol-3-yl)-3-{6-[4-(1-methyl-cyclohexanecarbonyl)-piperazin-1-yl]-pyridin-3-yl}-urea methanesulfonate | 558 |
| 125 | 1-(5-tert-Butyl-2-p-tolyl-2H-pyrazol-3-yl)-3-{6-[4-(2,2-dimethyl-pentanoyl)-piperazin-1-yl]-pyridin-3-yl}-urea mesylate | 546 |
| 126 | 1-(5-tert-Butyl-2-p-tolyl-2H-pyrazol-3-yl)-3-{6-[4-(2,2-dimethyl-propionyl)-piperazin-1-yl]-5-trifluoromethyl-pyridin-3-yl}-urea mesylate | 586 |
| 127 | 1-(5-tert-Butyl-2-p-tolyl-2H-pyrazol-3-yl)-3-{6-[4-(2,2-dimethyl-propionyl) piperazin-1-yl]-4-methyl-pyridin-3-yl}-urea mesylate. | 532 |
| 128 | 1-(5-tert-Butyl-2-p-tolyl-2H-pyrazol-3-yl)-3-{4-methyl-6-[4-(1-methyl-cyclopropanecarbonyl)-piperazin-1-yl]-pyridin-3-yl}-urea mesylate | 530 |
| 129 | 1-(5-tert-Butyl-2-p-tolyl-2H-pyrazol-3-yl)-3-{4-chloro-6-[4-(2,2-dimethyl-propionyl)-piperazin-1-yl]-pyridin-3-yl}-urea mesylate salt | 552 |
| 130 | 1-(5-tert-Butyl-2-p-tolyl-2H-pyrazol-3-yl)-3-{5-chloro-6-[4-(1-methyl-cyclopropanecarbonyl)-piperazin-1-yl]-pyridin-3-yl}-urea mesylate | 550 |
| 131 | 1-(5-tert-Butyl-2-p-tolyl-2H-pyrazol-3-yl)-3-{5-methyl-6-[4-(1-methyl-cyclopropanecarbonyl)-piperazin-1-yl]-pyridin-3-yl}-urea mesylate | 530 |
| 132 | 1-(5-tert-Butyl-2-p-tolyl-2H-pyrazo-l-3-yl)-3-{5-methyl-6-[4-(1-methyl-cyclopropanecarbonyl)-piperazin-1-yl]-pyridin-3-yl}-urea mesylate | 624 |
| 133 | 1-{6-[4-(2,6-Difluoro-benzoyl)-piperazin-1-yl]-2-methyl-pyridin-3-yl}-3-[5-(2-fluoro-1,1-dimethyl-ethyl)-2-p-tolyl-2H-pyrazol-3-yl]-urea | 606 |

EXAMPLE 134

1-(5-tert-Butyl-2-p-tolyl-2H-pyrazol-3-yl)-3-{2-[1-(2,6-difluoro-benzoyl)-piperidin-4-yloxy]-pyridin-4-yl}-urea methanesulfonate

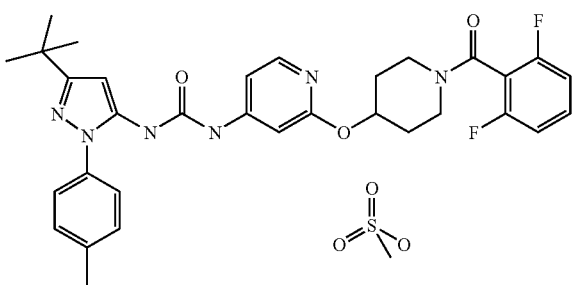

Treat a solution of 1-(5-tert-butyl-2-p-tolyl-2H-pyrazol-3-yl)-3-[2-(piperidin-4-yloxy)-pyridin-4-yl]-urea (Preparation 71; 179 mg, 400 mmol), 2,6-difluorobenzoic acid (76 mg, 0.48 mmol) and catalytic DMAP (5 mg) in dichloromethane (4 ml) with EDCI (92 mg, 0.48 mmol). Stir the resulting mixture overnight at ambient temperature then wash with saturated aqueous sodium bicarbonate solution. Dry the organic layer over sodium sulfate and concentrate under a stream of nitrogen. Tritrate the residue with a few milliliters DCM. After sonication, filter the white solid and dry under reduced pressure to give 162 mg of the title compound as the free base (69% yield).

Treat a suspension of the free amine in 3:2 DCM:MeOH (5 mL) with 2 M methane sulfonic acid in dichloromethane (1 equiv.; 0.138 mL). Stir the resulting mixture until the solution clears then concentrate under a stream of nitrogen and dry under reduced pressure to afford the title salt. (LCMS ES+ (m/z) 589 [M+H]).

Prepare the following compound using procedures substantially analogous to those described above.

TABLE

| EXAMPLE | Compound | MS(ES+): m/z [M + H] |
|---|---|---|
| 135 | 1-{2-[1-(2,6-Difluoro-benzoyl)-piperidin-4-yloxy]-pyridin-4-yl}-3-[5-(1-methyl-cyclopropyl)-2-p-tolyl-2H-pyrazol-3-yl]-urea methanesulfonate. | 587 |

EXAMPLE 136

1-{2-[1-(2,6-Difluoro-benzoyl)-piperidin-4-yloxy]-4-yl}-3-[5-(2-fluoro-1-fluoromethyl-1-methyl-ethyl)-2-p-tolyl-2H-pyrazol-3-yl]-urea

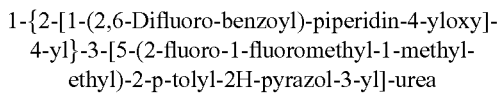

Heat a solution of [4-(4-amino-pyridin-2-yloxy)-piperidin-1-yl]-(2,6-difluoro-phenyl)-methanone (265 mg, 0.80 mmol), 5-(1-fluoromethyl-cyclopropyl)-2-p-tolyl-2H-pyrazol-3-yl]-carbamic acid 2,2,2-trichloro-ethyl ester (350 mg, 0.80 mmol) and diisopropylethylamine (700 mL) in 4 mL of DMSO at 60° C. for 16 hours. Cool the resulting mixture to ambient temperature and add water. Filter the precipitate, rinse with water, then pentane, and vacuum oven dry at 60° C. Subject residue to silica gel chromatography eluting with a gradient of 2M ammonia-methanol in dichloromethane (0 to 2%) to give 85 mg of product.

Prepare the following compounds using procedures substantially analogous to those described above.

TABLE

| EXAMPLE | Compound | MS(ES+): m/z [M + H] |
|---|---|---|
| 137 | 1-{2-[1-(2,6-Difluoro-benzoyl)-piperidin-4-yloxy]-pyridin-4-yl}-3-[5-(2-fluoro-1,1-dimethyl-ethyl)-2-p-tolyl-2H-pyrazol-3-yl]-urea | 607 |
| 138 | 1-{2-[1-(2,6-Difluoro-benzoyl)-piperidin-4-yloxy]-pyridin-4-yl}-3-[5-(1-fluoromethyl-cyclopropyl)-2-p-tolyl-2H-pyrazol-3-yl]-urea | 605 |

EXAMPLE 139

1-{2-[1-(2,6-Difluoro-benzoyl)-piperidin-4-yloxy]-pyridin-4-yl}-3-[5-(2-fluoro-1-fluoromethyl-1-methyl-ethyl)-2-p-tolyl-2H-pyrazol-3-yl]-urea mesylate Add 0.114 mL (0.114 mmol) of a freshly prepared 1 M solution of MeSO$_3$H in DCM/MeOH (95:5) to a solution of 71 mg (0.114 mmol) of 1-{2-[1-(2,6-Difluoro-benzoyl)-piperidin-4-yloxy]-pyridin-4-yl}-3-[5-(2-fluoro-1-fluoromethyl-1-methyl-ethyl)-2-p-tolyl-2H-pyrazol-3-yl]-urea in 2 mL of a 95:5 DCM/MeOH mixture. Stir the mixture for 20 min at room temperature, then evaporate the solvents under N$_2$ stream. Titurate the residue with Et$_2$O to afforded the title compound (76 mg, 93% yield) (100% purity). ES+(m/z)=625 [M+H].

Prepare the following compound using procedures substantially analogous to those described above.

TABLE

| EXAMPLE | Compound | MS(ES+): m/z [M + H] |
|---|---|---|
| 140 | 1-{2-[1-(2,6-Difluoro-benzoyl)-piperidin-4-yloxy]-pyridin-4-yl}-3-[5-(2-fluoro-1,1-dimethyl-ethyl)-2-p-tolyl-2H-pyrazol-3-yl]-urea mesylate | 607 |

EXAMPLE 141

1-{6-[4-(2,6-Difluoro-benzoyl)-piperazin-1-yl]-5-methyl-pyridin-3-yl}-3-[5-(2-fluoro-1,1-dimethyl-ethyl)-2-p-tolyl-2H-pyrazol-3-yl]-urea methanesulfonate

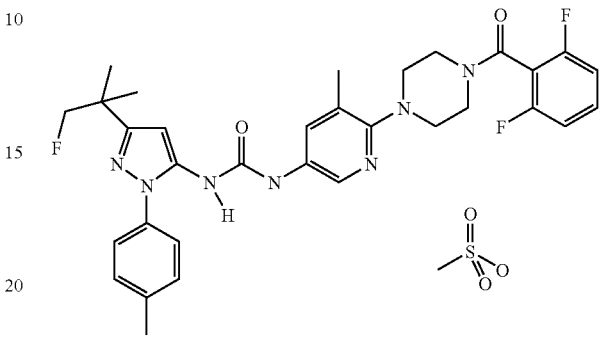

Add DIEA (2 equiv.) to a solution of [4-(5-amino-3-methyl-pyridin-2-yl)-piperazin-1-yl]-(2,6-difluoro-phenyl)-methanone (400 mg, 1.205 mmol) and [5-(2-fluoro-1,1-dimethyl-ethyl)-2-p-tolyl-2H-pyrazol-3-yl]-carbamic acid 2,2,2-trichloro-ethyl ester (1 equiv) in acetonitrile (12 mL). Stir the mixture at 80° C. in a sealed tube. After 4 days, remove solvent. Dilute crude with DCM, extract with water, and dry over Na$_2$SO$_4$. Filter and remove solvent under reduced pressure. Subject solid to silica gel chromatography, eluting with hexane/acetone 3:1 to obtain 352 mg of 1-{6-[4-(2,6-difluoro-benzoyl)-piperazin-1-yl]-5-methyl-pyridin-3-yl}-3-[5-(2-fluoro-1,1-dimethyl-ethyl)-2-p-tolyl-2H-pyrazol-3-yl]-urea as a white solid (48% yield). ES+(m/z): 606 [M+1]

Dissolve 50 mg (0.083 mmol) of the free base 1-{6-[4-(2,6-difluoro-benzoyl)-piperazin-1-yl]-5-methyl-pyridin-3-yl}-3-[5-(2-fluoro-1,1-dimethyl-ethyl)-2-p-tolyl-2H-pyrazol-3-yl]-urea in DCM (0.5 mL). Add 1 equiv of trifluoromethanesulfonic acid in DCM (1 N). After 30 min, remove solvent to afford a white solid. After several washings with ether/DCM, dry the solid under reduced pressure to obtain 55 mg of the title compound (95% yield). ES+(m/z): 606 [M+1].

Inhibition of p38 Kinase

Standard Solution Preparations

The kinase buffer solution is prepared by combining 2.5 mL 1M Tris-HCl (pH 7.5), 0.1 mL 1M dithiothreitol, 1.0 mL 1M magnesium chloride, and 300 µL 1% Triton X-100 and diluting to 100 mL with water. 84 mL of this kinase buffer solution is combined with 16 mL DMSO to prepare the 16% DMSO solution.

The 200 µM ATP solution is prepared by adding 102.6 µL 10 mM aqueous ATP, 25 µL $^{33}$P-ATP, and 163.5 µL of 4 mM aqueous Epidermal Growth Factor Peptide 661-681 (Biomol, Catalog #P-121) in 5 mL kinase buffer solution.

The p38 kinase enzyme solution is prepared by dissolving 9.5 µL concentrated enzyme solution (250 ng p38 enzyme/µL kinase buffer solution) in 1536 µL kinase buffer solution.

Sample Preparation

An 80 µM solution of each test compound and control compound are prepared by dissolving 2 µL of a 10 mM stock solution of the respective compounds in dimethylsulfoxide in 248 μL of the 16% DMSO solution in a Costar 96-well microtiter plate. The plate is placed onto the Tecan Genesis automated liquid handler for 1:3 serial dilutions.

Assay

10 μL of serially diluted compound is placed with a Beckman Multimek 96-well automated liquid handler to the assay plate. 20 μL of 200 μM ATP solution is added with a Titertek Multidrop 8-channel liquid handler. 10 μL of p38 kinase enzyme solution is transferred to the assay plate using the Multimek. The mixture is allowed to react for 40 minutes at 30° C. and then the reaction is stopped by adding 60 mL of freshly prepared 5% glacial AcOH with Multidrop. 80 μL of this solution is transferred to an "MAPH" plate using the Multimek. The plates are allowed to set for 30 minutes at room temperature and then washed/aspirated on the Titertek MAP extractor with freshly prepared 0.5% glacial AcOH (1×300 μL, 2×200 mL). The plates are blotted and 100 μL MicroScint-20 scintillation fluid (Packard Bioscience) is added with the Multidrop. The plates are allowed to sit for 30 min and counted on a PE/Wallac Microbeta Trilux scintillation counter for $^{33}$P-isotope.

The compound exemplified in Example 5 is initially tested at 10 concentrations (20 μM-1 nM using 1:3 serial dilutions). Compounds with $IC_{50}$ values less than 25 nM are re-tested at a starting concentration of 2 μM to 0.1 nM (1:3 serial dilutions). $IC_{50}$ values are calculated (IDBS ActivityBase software) for each compound using non-linear regression. Example 5 is tested essentially as described above and is found to inhibit the p38 kinase enzyme with an $IC_{50}$ of 22 nM.

Inhibition of p-MAPKAPK2 In Vitro

RAW 264.7 cells (a murine monocytic/macrophage line ATCC) are seeded at a density of 50,000 cells/well in 96-well plates with RPMI-1640 medium plus 10% fetal bovine serum (FBS) and allowed to settle and adhere to the bottom of the well for 48 hours. After reaching confluence, cells are treated for 2 hours with 10 serial dilutions of different compounds. A control compound is always included. After 2 hours, anisomicin (100 ug/ml) is added and cells are incubated for 30 minutes at 37° C. under a 5% $CO_2$ atmosphere. Then, cells are fixed and treated with hydrogen peroxide in order to remove endogenous peroxidase. Finally, plates are blocked with FBS, washed, and an ELISA assay is carried out by using an antiphospho-MAPKAPK (Thr 334, Cell Signalling, Cat # 3041) antibody and ahP-Conjugated Secondary Antibody. This reaction is detected by using FEMTO (Pierce) which is an enhanced chemiluminiscent substrate ahP that results in rapid kinetic light output and high signal intensity.

The exemplified compounds were tested essentially as described above and were found to have $IC_{50}$ values less than or equal to 300 nM. Compounds prepared in Examples 111, 113, 114, 115, 119 were tested in the presence of 100% serum, essentially as described above, and were found to have $IC_{50}$ values less than or equal to 500 nM. The following compounds were tested essentially as described above and were found to have the following activity:

| EXAMPLE | $IC_{50}$ (nM) |
|---|---|
| 45 | 6.7 |
| 5 | 4.5 |
| 92 | 16 |
| 77 | 176 |
| 128 | 286 |

Inhibition of TNFα In Vitro

Mouse Peritoneal Macrophages 1 mL thioglycolate broth (5.0 g yeast extract, 15.0 g casitone or trypticase, 5.0 g dextrose, 2.5 g sodium chloride, 0.75 g L-cystine, 0.5 g sodium thioglycolate, 1.0 mg resazurin, and 0.75 g agar in 1.0 L distilled water) are injected into the peritoneal cavity of Balb/C female mice. At day 4 or 5 post-injection the mice are sacrificed and then injected i.p. with 4 mL RPMI-1640 medium (BioWhittaker) and the peritoneal macrophages are withdrawn by syringe.

Cytokine Production

Mouse peritoneal macrophages are counted with a hemocytometer and adjusted to $5 \times 10^5$ cells/well in 96-well plates in RPMI-1640 medium with 10% fetal bovine serum. 200 μL/well is plated in 96-well plates and the cells allowed to settle and adhere to the bottom of the well for at least 3 hours. The test compound or standard p38 kinase inhibitor is pre-treated using a series of 8 concentrations for 1 hour at 37° C. (20 μL/well). The cells are treated with a mixture of 50 ng/mL lipopolysaccharide (LPS) and 10 U/mL interferon-γ for 18 hours at 37° C. (20 μL/well). The conditioned media is harvested and assayed for TNFα production using the Luminex detection procedure.

TNFα/Luminex Detection Assay (Bio-Rad Bio-Plex Kit—Catalog #171-G12221)

The lyophilized premixed TNFα standard (1 standard tube/two 96-well plates) is reconstituted with 50 μL sterile water (500,000 pg/mL). The samples are vortexed for 5 seconds, incubated on ice for 30 minutes, and vortexed for 5 seconds before use. A set of twelve 1.5 mL tubes are labeled with #1-thru #12 and then the amounts of cell media shown below added to the appropriate tubes (standard concentrations are as follows: 50,000; 25,000; 12,500; 6,250; 3,125; 1,562.5; 781.3; 390.6; 195.3; 97.7; 48.8; and 24.4 pg/mL). The premixed anti-cytokine conjugated beads are vortexed (25×) vigorously for 30 seconds. The anti-cytokine conjugated beads are diluted to a 1× concentration using 1× Bio-Plex Assay Buffer. For every plate, 240 μL of the pre-mixed beads is added to 5760 μL of Bio-Plex Assay Buffer. A Millipore 96-well filter plate is blocked with 100 μL/well of blocking buffer. The blocking buffer is filtered through using a Millipore filtration system and then toweled dry. 2 washes are performed on the filter plate with 100 μl/well of Bio-Plex Assay Buffer and toweled dry. The 1× anti-cytokine conjugated beads are vortexed for 15 seconds and added 50 μL to each well. This is filtered through and toweled dry. 2 washes are performed on plates with 100 μl/well of Bio-Plex Wash Buffer. Again, it is filtered through and toweled dry. 50 μL of sample or standard is added to each sample well. This is incubated for 60 seconds at room temperature on a shaker protected from light at setting 6 and then for 30 min at setting 3 and then placed in the refrigerator overnight. 3 washes are performed with Bio-Plex Wash Buffer. Filter through and towel dry. The cytokine detection antibody is prepared (~10 min prior to use) for every plate and 60 μL of the premixed cytokine detection antibody stock is added to 5940 μL of Bio-Plex Detection Antibody Diluent.

50 μL of cytokine detection antibody is added and incubated for 60 seconds at room temperature on a shaker protected from light at setting 6 and then for 30 minutes at setting 3.3 washes are performed with the Bio-Plex Wash Buffer. This is filtered through and toweled dry. Strept-PE (~10 minutes prior to use) is prepared for every plate and 60 μL to 5940

μL of Bio-Plex Assay Buffer added. 50 μL of Streptavidin-PE is added to each well and incubated for 60 seconds at room temperature on a shaker protected from light at setting 6 and then for 10 minutes at setting 3. 3 washes are performed with Bio-Plex Wash Buffer. This is filtered through. The beads are re-suspended in 100 μL/well of Bio-Plex Assay Buffer. Standards and samples are read on a Luminex machine. These intensity readings are then converted to picogram/milliliter units based on a 12-point standard curve created in duplicate using a four-parameter logistic regression method (Bio-Plex Manager 2.0, Bio-Rad), and the $IC_{50}$ calculated.

The compound exemplified in Example 5 is tested essentially as described above and suppressed TNFα in vitro with an $IC_{50}$ of 18 nM.

Inhibition of TNFα In Vivo

Compounds are administered p.o. (30, 10, 3 and 1 mg/kg) to female Balb/c mice (6 mice/dose). 1 hour following compound administration at 4 doses (P.O. at volume of 0.1 mL/mouse; vehicle: 1% NaCMC/0.25% Tween-80 in water); mice are given an IP-injection of LPS at 400 μg/kg. 1.5 hours after LPS challenging, mice are anesthetized with isoflurane and blood is taken via cardiac puncture. TNFα-levels in the plasma are determined using ELISA kit from R&D Systems and dose response ED50 is determined.

The compound exemplified in Example 5 is tested essentially as described above and suppressed TNFα in vivo with an TMED50 of 2.24 mg/kg. The Threshold Minimum Effective Dose (TMED) 50 is the dose at which greater than or equal to 50% inhibition was achieved and statistically different from control/placebo.

Oral Exposure

Compounds are screened for oral exposure in male Fischer 344 rats. Animals are fasted overnight and administered test compounds prepared as suspensions in sodium carboxymethylcellulose (1% w/v) containing Tween 80 (0.25% v/v) and antifoam (0.1% w/v). Dose suspensions are prepared at 1 mg/mL and administered at 1 mL/kg by gavage. Blood samples are taken between 0.5 h and 7 h after dose administration and plasma are prepared by centrifugation. Plasma samples are analyzed using online solid phase extraction and LC/MS/MS.

The compound exemplified in Example 5 is tested essentially as described above and the Cmax is 9390 ng/mL with an AUC(0-7h) of 36800 ng·h/mL.

Effect on Intra-Articular LPS Induced TNFα

Intra-articular injection of LPS into rat ankles induces the synthesis of TNFα, which can be measured in synovial lavage fluid. High levels of TNFα are detectable within 2 hours. Since the joint is the site where arthritis develops, this model can rapidly determine whether an orally administered compound has an effect on an inflammatory response in the synovium.

Six female Lewis rats (150-200 g) are place in each treatment group. The animals are given vehicle (1% NaCarboxymethylcellulose-0.25% Tween 80) or test compound (1 mg/kg, 3 mg/kg, 10 mg/kg, and 30 mg/kg) orally. One hour later, 10 μl LPS (10 μg) is administered intra-articularly into the right ankle of each rat, while the left ankle receives 10 μL of saline. After two hours, each ankle is lavaged with 100 μL of saline. The lavage is collected and stored at −80° C.

Group #1: Vehicle (1% NaCMC-0.25% Tween 80, 1 mL, PO)
Group #2: Test compound (1 mg/kg, 1 mL, PO)
Group #3: Test compound (3 mg/kg, 1 mL, PO)
Group #4: Test compound (10 mg/kg, 1 mL, PO)
Group #5: Test compound (30 mg/kg, 1 mL, PO)

TNFα is measured with a commercially available ELISA kit (R&D, RTA00). Treatment with the compound exemplified in Example 5 produces a dose response inhibition of TNFα synthesis, as measured in the synovial lavage fluid with a TMED50=3.57 mg/kg.

Anisomycin-Stimulated Mice Ex-Vivo Phospho-MAP-KAPK2 Inhibition Assay by Flow Cytometry Female Balb/c mice with 8-10 week-old age are purchased from Taconic Inc. and dosed po with 0.2 mL volume of compounds at the concentrations of 30, 10, 3, 1 mg/kg. Blood is obtained from cardiac puncture after 2 hours or other indicated time periods and collected in EDTA-containing tubes. 100 μL of blood is incubated at 37° C. for 10 minutes. Whole blood is then mixed with FITC-conjugated rat anti-mouse Ly-6G mAb (1:250) and APC-conjugated rat anti-mouse CD11b mAb (1:100) and stimulated with 10 μg/ml anisomycin. Both cell surface antigen staining and anisomycin stimulation is conducted at 37° C. for 15 min and followed up with Lyse/Fix buffer (BD Biosciences, Cat#558049) for 10 min at room temperature. Lysed blood samples are spun down at 600×g for 8 minutes at room temperature with additional wash once by 4 mL PBS. 200 μL of diluted anti-Phospho-MAPKAPK-2 (Thr334) antibody (1:100 dilution) (Cell Signaling, Cat#3041) and mouse BD Fc Block (1:100 dilution) (BD Biosciences, 553141) in permeabilization Medium B (Caltag, Catg GAS002S-5) are added into blood cells and incubate at room temperature for 30 minutes. After the incubation, 3 mL of stain/wash buffer is added and cells are spanned down as described above with additional wash with 3 ml stain/wash buffer. Cells are then subjected to flowcytometry assay using Beckman Coulter F500. Mean fluorescence of phosphono-MapKap-K2 staining is measured on gated CD11b+Ly6G-cells. Data analysis is performed by JMP program. Treatment with the compound exemplified in Example 5 produces a dose response inhibition of p-MAP-KAPK synthesis with TMED50=2.28 mg/kg Rat Collagen Induced Arthritis Efficacy Model Female Lewis rats (≈190 g, Charles River Labs) are immunized with Bovine type II collagen (2 mg/mL) emulsified with an equal volume of adjuvant (aluminum hydroxide). are used. The rats are immunized with approximately 0.3 mg of the emulsion intradermally on the back near the base of the tail. All animals are re-immunized 7 days later according to the same protocol. The rats begin to develop arthritis (characterized by swelling and redness of one or both ankles) from 12 to 14 days after the first immunization. The rats are equally distributed into five treatment groups at the first signs of arthritis and treatment is initiated with each rat dosed bid for 14 days.

Treatment Groups:

Group 1 Vehicle (1% NaCarboxymethylcellulose+0.25% Tween 80) 1 mL, PO,
   Bid×14 days
Group 2 Test compound, 5 mg/kg, 1 mL, PO, Bid×14
Group 3 Test compound, 15 mg/kg, 1 mL, PO, Bid×14
Group 4 Test compound, 30 mg/kg, 1 mL, PO, Bid×14
Group 5 Prednisolone 10 mg/kg, 1 mL, PO, qd×14

Ankle diameter is measured with calipers 5 days a week and recorded. Data is expressed as the area under the curve (AUC) generated from the composite inflammation scores and statistical analysis performed. The compound exemplified in Example 5 exhibited a histology TMED 50=5 mg/kg bid.

Oral administration of the compound of the present invention is preferred. However, oral administration is not the only route or even the only preferred route. For example, transdermal administration may be very desirable for patients who are forgetful or petulant about taking oral medicine, and the intravenous route may be preferred as a matter of convenience or to avoid potential complications related to oral administration. Compounds of Formula I may also be administered by the percutaneous, intramuscular, intranasal or intrarectal route in particular circumstances. The route of administration may be varied in any way, limited by the physical properties of the drugs, the convenience of the patient and the caregiver, and other relevant circumstances (*Remington's Pharmaceutical Sciences*, 18th Edition, Mack Publishing Co. (1990)).

The pharmaceutical compositions are prepared in a manner well known in the pharmaceutical art. The carrier or excipient may be a solid, semi-solid, or liquid material that can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

The compound of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations of the present invention may be determined by methods well known to the skilled artisan.

The tablets, pills, capsules, troches, and the like may also contain one or more of the following adjuvants: binders such as povidone, hydroxypropyl cellulose, microcrystalline cellulose, or gelatin; excipients or diluents such as: starch, lactose, microcrystalline cellulose or dicalcium phosphate, disintegrating agents such as: croscarmellose, crospovidone, sodium starch glycolate, corn starch and the like; lubricants such as: magnesium stearate, stearic acid, talc or hydrogenated vegetable oil; glidants such as colloidal silicon dioxide; wetting agents such as: sodium lauryl sulfate and polysorbate 80; and sweetening agents such as: sucrose, aspartame or saccharin may be added or a flavoring agent such as: peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, as coatings. Thus, tablets or pills may be coated with sugar, hydroxypropyl methylcellulose, polymethacrylates, or other coating agents. Syrups may contain, in addition to the present compounds, sucrose as a sweetening agent and certain preservatives, dyes and colorings and flavors. Materials used in preparing these various compositions should be pharmaceutically pure and non-toxic in the amounts used. A preferred formulation is prepared by adding 1% NaCarboxymethylcellulose-0.25% Tween to the desired dose of a compound of Formula I.

The compounds of Formula I are generally effective over a wide dosage range. For example, dosages per day normally fall within the range of about 0.0001 to about 30 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

We claim:

1. A compound of Formula I:

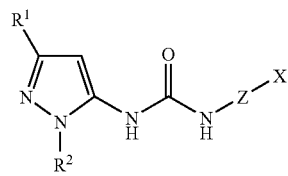

where:

Z is selected from the group consisting of

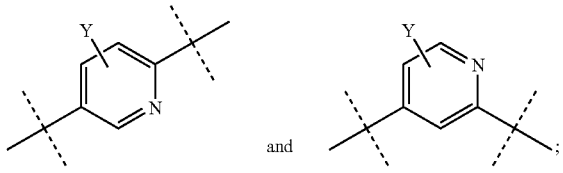

and

X is selected from the group consisting of (i)

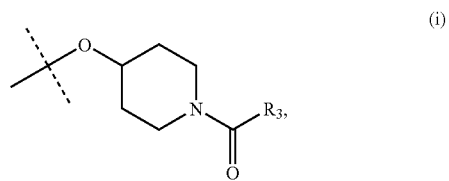

(ii)

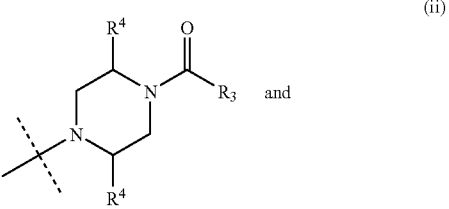

and (iii)

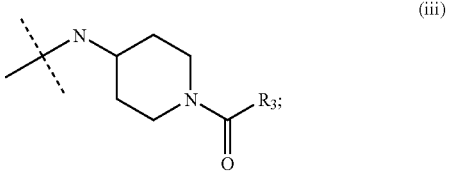

$R^1$ is $C_1$-$C_7$ alkyl optionally substituted with one to six substituents selected from the group consisting of halo and $C_1$-$C_4$ alkylhalo; $C_3$-$C_6$ cycloalkyl optionally substituted with one or two substituents selected from the group consisting of $C_1$-$C_4$ alkyl and trifluoromethyl; or trimethylsilyl;

$R^2$ is phenyl optionally substituted with $C_1$-$C_4$ alkyl, or pyridinyl optionally substituted with $C_1$-$C_4$ alkyl;

Y is hydrogen, $C_1$-$C_4$ alkyl, halo, or $C_1$-$C_4$ alkylhalo;

$R^3$ is $C_1$-$C_7$alkyl optionally substituted with $C_3$-$C_6$ cycloalkyl; $C_1$-$C_4$ alkoxy; $C_1$-$C_4$ alkylhalo; $C_3$-$C_6$ cycloalkyl optionally substituted with one to four substituents selected from the group of $C_1$-$C_4$ alkyl and trifluoromethyl; or pyridyl, phenyl or thienyl each optionally substituted with a first substituent selected from the group consisting of: halo, cyano, $C_1$-$C_4$ alkyl, $C_1$-$C_4$ alkylhalo and $C_1$-$C_4$ alkoxy, and optionally further substituted with a second substituent selected from the group of $C_1$-$C_4$ alkyl and halo;

$R^4$ is hydrogen or $C_1$-$C_4$ alkyl; or a pharmaceutically acceptable salt thereof.

2. A compound of claim 1 where X is

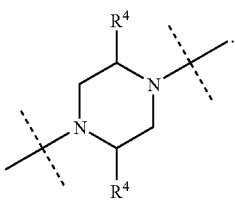

(ii)

3. A compound of claim 1 wherein $R^4$ is hydrogen.

4. A compound of claim 1 where $R^2$ is 4-tolyl.

5. A compound of claim 1 where $R^1$ is $C_1$-$C_7$ alkyl.

6. A compound of claim 1 where $R^1$ is tert-butyl.

7. A compound of claim 1 where $R^3$ is 2,6-difluorophenyl.

8. A compound of the formula:

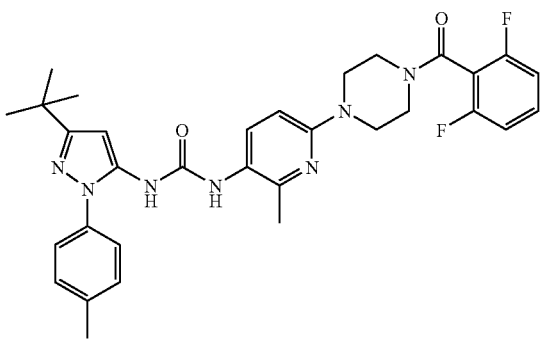

1-(5-tert-Butyl-2-p-tolyl-2H-pyrazol-3-yl)-3-{6-[4-(2,6-difluoro-benzoyl)-piperazin-1-yl]-2-methyl-pyridin-3-yl}urea or a pharmaceutically acceptable salt thereof.

9. A pharmaceutical formulation comprising a compound of claim 1 in combination with a pharmaceutically acceptable excipient, carrier, or diluent.

* * * * *

UNITED STATES PATENT AND TRADEMARK OFFICE
CERTIFICATE OF CORRECTION

PATENT NO.         : 7,652,015 B2
APPLICATION NO.    : 12/088526
DATED              : January 26, 2010
INVENTOR(S)        : Jolie Anne Bastian et al.

It is certified that error appears in the above-identified patent and that said Letters Patent is hereby corrected as shown below:

On the Title page:
Insert -- [60] Related U.S. Application Data
Provisional application No. 60/821,963 filed Aug. 10, 2006, and
Provisional application No. 60/731,604 filed Oct. 28, 2005. --

On the first page of the specification, insert the following
cross-reference after the title:
-- This is the national phase application, under 35 USC 371,
for PCT/US2006/041644, filed October 25, 2006, which claims
the benefit, under 35 USC 119(e), of US provisional application
60/731,604 filed October 28, 2005, EP 06380151.8 filed June 2,
2006, and US provisional application 60/821,963, filed August
10, 2006. --

Signed and Sealed this

Twenty-third Day of November, 2010

David J. Kappos
*Director of the United States Patent and Trademark Office*

UNITED STATES PATENT AND TRADEMARK OFFICE
CERTIFICATE OF CORRECTION

PATENT NO.        : 7,652,015 B2
APPLICATION NO.   : 12/088526
DATED             : January 26, 2010
INVENTOR(S)       : Jolie Anne Bastian et al.

It is certified that error appears in the above-identified patent and that said Letters Patent is hereby corrected as shown below:

In the issued patent, please note the following corrections:

Col. 69, Claim 1, line 10 delete "$C_1$-$C_7$alkyl" and insert -- $C_1$-$C_7$ alkyl --.

Col. 69, Claim 2, delete " 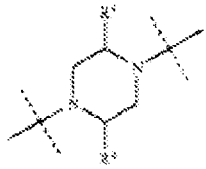 " and insert -- 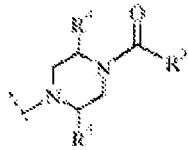 --.

Col. 70, Claim 7, line 7 delete "2,6-difluorophenzyl" and insert -- 2,6-difluorophenyl --.

Col. 70, Claim 8, line 26 delete "3-yl}urea" and insert "3-yl}-urea".

Signed and Sealed this
Twenty-seventh Day of September, 2011

David J. Kappos
*Director of the United States Patent and Trademark Office*